US010894966B2

(12) United States Patent
Moss et al.

(10) Patent No.: US 10,894,966 B2
(45) Date of Patent: Jan. 19, 2021

(54) VIRUS-BASED EXPRESSION VECTORS AND USES THEREOF

(71) Applicant: The USA, as represented by the Secretary, Department of Health and Human Services, Bethesda, MD (US)

(72) Inventors: Bernard Moss, Bethesda, MD (US); Linda S. Wyatt, Rockville, MD (US)

(73) Assignee: The United States of America, as Represented By The Secretary, Department of Health and Human Services, Rockville, MD (US)

( * ) Notice: Subject to any disclaimer, the term of this patent is extended or adjusted under 35 U.S.C. 154(b) by 720 days.

(21) Appl. No.: 15/514,119

(22) PCT Filed: Sep. 25, 2015

(86) PCT No.: PCT/US2015/052295

§ 371 (c)(1),
(2) Date: Mar. 24, 2017

(87) PCT Pub. No.: WO2016/049492

PCT Pub. Date: Mar. 31, 2016

(65) Prior Publication Data

US 2017/0298387 A1 Oct. 19, 2017

Related U.S. Application Data

(60) Provisional application No. 62/055,989, filed on Sep. 26, 2014.

(51) Int. Cl.

| | |
|---|---|
| ***C12N 15/86*** | (2006.01) |
| ***A61K 35/76*** | (2015.01) |
| ***A61K 39/145*** | (2006.01) |
| ***A61K 48/00*** | (2006.01) |
| ***C12N 9/12*** | (2006.01) |
| *A61K 39/00* | (2006.01) |

(52) U.S. Cl.

CPC .............. *C12N 15/86* (2013.01); *A61K 35/76* (2013.01); *A61K 39/145* (2013.01); *A61K 48/0066* (2013.01); *C12N 9/1247* (2013.01); *C12Y 207/07006* (2013.01); *A61K 2039/5256* (2013.01); *C12N 2710/24122* (2013.01); *C12N 2710/24143* (2013.01); *C12N 2710/24151* (2013.01); *C12N 2710/24171* (2013.01); *C12N 2760/16134* (2013.01); *C12N 2760/16171* (2013.01); *C12N 2799/023* (2013.01); *C12N 2830/00* (2013.01); *C12N 2830/001* (2013.01); *C12N 2830/002* (2013.01); *C12N 2830/005* (2013.01); *C12N 2830/55* (2013.01); *C12N 2830/60* (2013.01)

(58) Field of Classification Search

CPC .. A61K 39/145; A61K 48/0066; A61K 35/76; C12N 15/86; C12N 9/1247

See application file for complete search history.

(56) References Cited

FOREIGN PATENT DOCUMENTS

WO WO 95/30018 A2 11/1995

OTHER PUBLICATIONS

Upton et al. "Poxvirus Orthologous Clusters: toward Defining the Minimum Essential Poxvirus Genome," Journal of Virology, Jul. 2003, vol. 77, No. 13, pp. 7590-7600.

International Preliminary Report on Patentability for International (PCT) Patent Application No. PCT/US2015/052295, dated Apr. 6, 2017 8 pages.

Official Action for Australia Patent Application No. 2015320409, dated Apr. 13, 2018 3 pages.

Official Action for Canada Patent Application No. 2,962,100, dated Feb. 5, 2018 4 pages.

Official Action for European Patent Application No. 15775581.0, dated Oct. 31, 2018 4 pages.

International Search Report and Written Opinion prepare by the European Patent Office dated Nov. 20, 2015, for International Application No. PCT/US2015/052295.

Garcia A D et al: "Repression of Vaccinia Virus Holliday Junction Resolvase Inhibits Processing of Viral DNA into Unit-Length Genomes", Journal of Virology, vol. 75, No. 14, Jul. 15, 2001 (Jul. 15, 2001), pp. 6460-6471.

Sanz P et al: "Identification of a transcription factor, encoded by two vaccinia virus early genes, that regulates the intermediate stage of viral gene expression", Proceedings of the National Academy of Sciences, vol. 96, No. 6, Mar. 16, 1999 (Mar. 16, 1999), pp. 2692-2697.

Himly M et al: "Defective Vaccinia Virus as a Biologically Safe Tool for the Overproduction of Recombinant Human Secretory Proteins", Protein Expression and Purification, Academic Press, San Diego, CA, vol. 14, No. 3, Dec. 1, 1998 (Jan. 12, 1998), pp. 317-326.

Official Action for Australia Patent Application No. 2015320409, dated Nov. 26, 2018 3 pages.

Notice of Acceptance for Australia Patent Application No. 2015320409, dated Mar. 13, 2019 3 pages.

Official Action for Canada Patent Application No. 2,962,100, dated Nov. 27, 2018 4 pages.

Intention to Grant for European Patent Application No. 15775581.0, dated Apr. 15, 2019 7 pages.

*Primary Examiner* — Antonio Galisteo Gonzalez

(74) *Attorney, Agent, or Firm* — Sughrue Mion, PLLC

(57) ABSTRACT

Expression vectors ideal for use in vaccinating individuals against disease based on vaccinia virus and other chordopoxviruses having high expression of recombinant genes and low expression of vector genes in target animals, and low expression of recombinant genes and high expression of vector genes in cells used for propagation.

33 Claims, 23 Drawing Sheets

Specification includes a Sequence Listing.

T7LacILucΔA23 only forms plaques in complementing RK/A8A23 cells

- WRvFire expresses luciferase at equivalent high level in all cells
- T7LacILuc expresses luciferase at equivalent low level in all cells
- T7LacILucΔA23 expresses luciferase at lower level in RK/A8A23 cells and high level in non-complementing cells PCR product for insertion of P11 promoter and dsRed to knock out the A23 gene -PCR from Warren ΔA23 virus

SEQUENCE LISTING

```
<160> NUMBER OF SEQ ID NOS: 205

<210> SEQ ID NO 1
<211> LENGTH: 15
<212> TYPE: DNA
<213> ORGANISM: Vaccinia virus

<400> SEQUENCE: 1

aaagtagaaa atata                                                      15


<210> SEQ ID NO 2
<211> LENGTH: 15
<212> TYPE: DNA
<213> ORGANISM: Vaccinia virus

<400> SEQUENCE: 2

tatccggaga cgtca                                                      15


<210> SEQ ID NO 3
<211> LENGTH: 15
<212> TYPE: DNA
<213> ORGANISM: Vaccinia virus
```

<400> SEQUENCE: 3
attactgaat taata 15

<210> SEQ ID NO 4
<211> LENGTH: 15
<212> TYPE: DNA
<213> ORGANISM: Vaccinia virus

<400> SEQUENCE: 4
gcaacgtaaa acaca 15

<210> SEQ ID NO 5
<211> LENGTH: 15
<212> TYPE: DNA
<213> ORGANISM: Vaccinia virus

<400> SEQUENCE: 5
aaaaaataaa aaaaa 15

<210> SEQ ID NO 6
<211> LENGTH: 15
<212> TYPE: DNA
<213> ORGANISM: Vaccinia virus

<400> SEQUENCE: 6
agtaaagaaa aagaa 15

<210> SEQ ID NO 7
<211> LENGTH: 15
<212> TYPE: DNA
<213> ORGANISM: Vaccinia virus

<400> SEQUENCE: 7
aaaattgata aataa 15

<210> SEQ ID NO 8
<211> LENGTH: 15
<212> TYPE: DNA
<213> ORGANISM: Vaccinia virus

<400> SEQUENCE: 8
aaattagaca tttga 15

<210> SEQ ID NO 9
<211> LENGTH: 15
<212> TYPE: DNA
<213> ORGANISM: Vaccinia virus

<400> SEQUENCE: 9
ataactgaaa tgaaa 15

<210> SEQ ID NO 10
<211> LENGTH: 15
<212> TYPE: DNA
<213> ORGANISM: Vaccinia virus

<400> SEQUENCE: 10
aaagatgaaa aagta 15

<210> SEQ ID NO 11
<211> LENGTH: 15
<212> TYPE: DNA

<213> ORGANISM: Vaccinia virus

<400> SEQUENCE: 11
attaatgaaa taata 15

<210> SEQ ID NO 12
<211> LENGTH: 15
<212> TYPE: DNA
<213> ORGANISM: Vaccinia virus

<400> SEQUENCE: 12
aaaaatgaaa atgga 15

<210> SEQ ID NO 13
<211> LENGTH: 15
<212> TYPE: DNA
<213> ORGANISM: Vaccinia virus

<400> SEQUENCE: 13
aaaacataaa aatta 15

<210> SEQ ID NO 14
<211> LENGTH: 15
<212> TYPE: DNA
<213> ORGANISM: Vaccinia virus

<400> SEQUENCE: 14
ataacataaa aataa 15

<210> SEQ ID NO 15
<211> LENGTH: 15
<212> TYPE: DNA
<213> ORGANISM: Vaccinia virus

<400> SEQUENCE: 15
aagatagatt tccta 15

<210> SEQ ID NO 16
<211> LENGTH: 15
<212> TYPE: DNA
<213> ORGANISM: Vaccinia virus

<400> SEQUENCE: 16
aaaaatgaaa aaata 15

<210> SEQ ID NO 17
<211> LENGTH: 15
<212> TYPE: DNA
<213> ORGANISM: Vaccinia virus

<400> SEQUENCE: 17
gaaaaagaaa ttcct 15

<210> SEQ ID NO 18
<211> LENGTH: 15
<212> TYPE: DNA
<213> ORGANISM: Vaccinia virus

<400> SEQUENCE: 18
aatggtgaaa aaatg 15

<210> SEQ ID NO 19
<211> LENGTH: 15

-continued

<212> TYPE: DNA
<213> ORGANISM: Vaccinia virus

<400> SEQUENCE: 19
aaaacataaa aataa 15

<210> SEQ ID NO 20
<211> LENGTH: 15
<212> TYPE: DNA
<213> ORGANISM: Vaccinia virus

<400> SEQUENCE: 20
ataattgtaa aaaca 15

<210> SEQ ID NO 21
<211> LENGTH: 15
<212> TYPE: DNA
<213> ORGANISM: Vaccinia virus

<400> SEQUENCE: 21
ataattgaaa atgga 15

<210> SEQ ID NO 22
<211> LENGTH: 15
<212> TYPE: DNA
<213> ORGANISM: Vaccinia virus

<400> SEQUENCE: 22
aaaaatttaa ttaca 15

<210> SEQ ID NO 23
<211> LENGTH: 15
<212> TYPE: DNA
<213> ORGANISM: Vaccinia virus

<400> SEQUENCE: 23
aaaagtgaaa aacaa 15

<210> SEQ ID NO 24
<211> LENGTH: 15
<212> TYPE: DNA
<213> ORGANISM: Vaccinia virus

<400> SEQUENCE: 24
aaaaaagaaa ataga 15

<210> SEQ ID NO 25
<211> LENGTH: 15
<212> TYPE: DNA
<213> ORGANISM: Vaccinia virus

<400> SEQUENCE: 25
gtagaagaaa ataat 15

<210> SEQ ID NO 26
<211> LENGTH: 15
<212> TYPE: DNA
<213> ORGANISM: Vaccinia virus

<400> SEQUENCE: 26
aaaaatgaaa cgtaa 15

<210> SEQ ID NO 27

-continued

<211> LENGTH: 15
<212> TYPE: DNA
<213> ORGANISM: Vaccinia virus

<400> SEQUENCE: 27
aaaaaacaaa atgaa 15

<210> SEQ ID NO 28
<211> LENGTH: 15
<212> TYPE: DNA
<213> ORGANISM: Vaccinia virus

<400> SEQUENCE: 28
gagacagtag tttta 15

<210> SEQ ID NO 29
<211> LENGTH: 15
<212> TYPE: DNA
<213> ORGANISM: Vaccinia virus

<400> SEQUENCE: 29
aaaaatgata aaata 15

<210> SEQ ID NO 30
<211> LENGTH: 15
<212> TYPE: DNA
<213> ORGANISM: Vaccinia virus

<400> SEQUENCE: 30
aataatgaaa aaata 15

<210> SEQ ID NO 31
<211> LENGTH: 15
<212> TYPE: DNA
<213> ORGANISM: Vaccinia virus

<400> SEQUENCE: 31
acaaaagtga atata 15

<210> SEQ ID NO 32
<211> LENGTH: 15
<212> TYPE: DNA
<213> ORGANISM: Vaccinia virus

<400> SEQUENCE: 32
ttaaatgaaa atata 15

<210> SEQ ID NO 33
<211> LENGTH: 15
<212> TYPE: DNA
<213> ORGANISM: Vaccinia virus

<400> SEQUENCE: 33
aataatgaaa aaaca 15

<210> SEQ ID NO 34
<211> LENGTH: 15
<212> TYPE: DNA
<213> ORGANISM: Vaccinia virus

<400> SEQUENCE: 34
taaagtgaaa atata 15

<210> SEQ ID NO 35
<211> LENGTH: 15
<212> TYPE: DNA
<213> ORGANISM: Vaccinia virus

<400> SEQUENCE: 35
attaatgaaa agtta 15

<210> SEQ ID NO 36
<211> LENGTH: 15
<212> TYPE: DNA
<213> ORGANISM: Vaccinia virus

<400> SEQUENCE: 36
ataacaaaaa taaaa 15

<210> SEQ ID NO 37
<211> LENGTH: 15
<212> TYPE: DNA
<213> ORGANISM: Vaccinia virus

<400> SEQUENCE: 37
aaaaatgata agata 15

<210> SEQ ID NO 38
<211> LENGTH: 15
<212> TYPE: DNA
<213> ORGANISM: Vaccinia virus

<400> SEQUENCE: 38
aaaactgtaa cacga 15

<210> SEQ ID NO 39
<211> LENGTH: 15
<212> TYPE: DNA
<213> ORGANISM: Vaccinia virus

<400> SEQUENCE: 39
aaaactgaaa atata 15

<210> SEQ ID NO 40
<211> LENGTH: 15
<212> TYPE: DNA
<213> ORGANISM: Vaccinia virus

<400> SEQUENCE: 40
taaagtgaac aataa 15

<210> SEQ ID NO 41
<211> LENGTH: 15
<212> TYPE: DNA
<213> ORGANISM: Vaccinia virus

<400> SEQUENCE: 41
aaaagggaaa tttga 15

<210> SEQ ID NO 42
<211> LENGTH: 15
<212> TYPE: DNA
<213> ORGANISM: Vaccinia virus

<400> SEQUENCE: 42
agaattgaaa acgaa 15

-continued

<210> SEQ ID NO 43
<211> LENGTH: 15
<212> TYPE: DNA
<213> ORGANISM: Vaccinia virus

<400> SEQUENCE: 43
aaaaatgaaa ataaa 15

<210> SEQ ID NO 44
<211> LENGTH: 15
<212> TYPE: DNA
<213> ORGANISM: Vaccinia virus

<400> SEQUENCE: 44
gtaaatgaaa aaaaa 15

<210> SEQ ID NO 45
<211> LENGTH: 15
<212> TYPE: DNA
<213> ORGANISM: Vaccinia virus

<400> SEQUENCE: 45
gaaaatgaaa aggta 15

<210> SEQ ID NO 46
<211> LENGTH: 15
<212> TYPE: DNA
<213> ORGANISM: Vaccinia virus

<400> SEQUENCE: 46
aaaactgatg aaata 15

<210> SEQ ID NO 47
<211> LENGTH: 15
<212> TYPE: DNA
<213> ORGANISM: Vaccinia virus

<400> SEQUENCE: 47
aaaaatgaaa tgata 15

<210> SEQ ID NO 48
<211> LENGTH: 15
<212> TYPE: DNA
<213> ORGANISM: Vaccinia virus

<400> SEQUENCE: 48
aataatgaaa acaaa 15

<210> SEQ ID NO 49
<211> LENGTH: 15
<212> TYPE: DNA
<213> ORGANISM: Vaccinia virus

<400> SEQUENCE: 49
aattctgaaa ctaga 15

<210> SEQ ID NO 50
<211> LENGTH: 15
<212> TYPE: DNA
<213> ORGANISM: Vaccinia virus

<400> SEQUENCE: 50
aaaattgaat tgcga 15

<210> SEQ ID NO 51
<211> LENGTH: 15
<212> TYPE: DNA
<213> ORGANISM: Vaccinia virus

<400> SEQUENCE: 51
taaagtgaaa atcta 15

<210> SEQ ID NO 52
<211> LENGTH: 15
<212> TYPE: DNA
<213> ORGANISM: Vaccinia virus

<400> SEQUENCE: 52
gcaatagaaa agatg 15

<210> SEQ ID NO 53
<211> LENGTH: 15
<212> TYPE: DNA
<213> ORGANISM: Vaccinia virus

<400> SEQUENCE: 53
aagaatgaaa taaca 15

<210> SEQ ID NO 54
<211> LENGTH: 15
<212> TYPE: DNA
<213> ORGANISM: Vaccinia virus

<400> SEQUENCE: 54
aaaaatgtaa taacg 15

<210> SEQ ID NO 55
<211> LENGTH: 15
<212> TYPE: DNA
<213> ORGANISM: Vaccinia virus

<400> SEQUENCE: 55
aaagtcgaaa aagaa 15

<210> SEQ ID NO 56
<211> LENGTH: 15
<212> TYPE: DNA
<213> ORGANISM: Vaccinia virus

<400> SEQUENCE: 56
aaaacataaa tataa 15

<210> SEQ ID NO 57
<211> LENGTH: 15
<212> TYPE: DNA
<213> ORGANISM: Vaccinia virus

<400> SEQUENCE: 57
aatatggaaa actaa 15

<210> SEQ ID NO 58
<211> LENGTH: 15
<212> TYPE: DNA
<213> ORGANISM: Vaccinia virus

<400> SEQUENCE: 58
aaaaatgaat taata 15

<210> SEQ ID NO 59
<211> LENGTH: 15
<212> TYPE: DNA
<213> ORGANISM: Vaccinia virus

<400> SEQUENCE: 59
aaaattgaag taata 15

<210> SEQ ID NO 60
<211> LENGTH: 15
<212> TYPE: DNA
<213> ORGANISM: Vaccinia virus

<400> SEQUENCE: 60
aatacttaaa atgta 15

<210> SEQ ID NO 61
<211> LENGTH: 15
<212> TYPE: DNA
<213> ORGANISM: Vaccinia virus

<400> SEQUENCE: 61
aaaatataaa ataaa 15

<210> SEQ ID NO 62
<211> LENGTH: 15
<212> TYPE: DNA
<213> ORGANISM: Vaccinia virus

<400> SEQUENCE: 62
aaaaatgaac tctta 15

<210> SEQ ID NO 63
<211> LENGTH: 15
<212> TYPE: DNA
<213> ORGANISM: Vaccinia virus

<400> SEQUENCE: 63
aaaatagaat aagta 15

<210> SEQ ID NO 64
<211> LENGTH: 15
<212> TYPE: DNA
<213> ORGANISM: Vaccinia virus

<400> SEQUENCE: 64
ataaatgaaa agata 15

<210> SEQ ID NO 65
<211> LENGTH: 15
<212> TYPE: DNA
<213> ORGANISM: Vaccinia virus

<400> SEQUENCE: 65
aaaactgaaa ataaa 15

<210> SEQ ID NO 66
<211> LENGTH: 15
<212> TYPE: DNA
<213> ORGANISM: Vaccinia virus

<400> SEQUENCE: 66
aaattgtaaa aaata 15

<210> SEQ ID NO 67
<211> LENGTH: 15
<212> TYPE: DNA
<213> ORGANISM: Vaccinia virus

<400> SEQUENCE: 67
aaatattaaa aaaaa 15

<210> SEQ ID NO 68
<211> LENGTH: 15
<212> TYPE: DNA
<213> ORGANISM: Vaccinia virus

<400> SEQUENCE: 68
gaaataaaaa acata 15

<210> SEQ ID NO 69
<211> LENGTH: 15
<212> TYPE: DNA
<213> ORGANISM: Vaccinia virus

<400> SEQUENCE: 69
aaaaataaaa atata 15

<210> SEQ ID NO 70
<211> LENGTH: 15
<212> TYPE: DNA
<213> ORGANISM: Vaccinia virus

<400> SEQUENCE: 70
aattttgtaa aaata 15

<210> SEQ ID NO 71
<211> LENGTH: 15
<212> TYPE: DNA
<213> ORGANISM: Vaccinia virus

<400> SEQUENCE: 71
attacatatt atata 15

<210> SEQ ID NO 72
<211> LENGTH: 15
<212> TYPE: DNA
<213> ORGANISM: Vaccinia virus

<400> SEQUENCE: 72
aaaacttaaa attta 15

<210> SEQ ID NO 73
<211> LENGTH: 15
<212> TYPE: DNA
<213> ORGANISM: Vaccinia virus

<400> SEQUENCE: 73
ataaaaatta aaaaa 15

<210> SEQ ID NO 74
<211> LENGTH: 15
<212> TYPE: DNA
<213> ORGANISM: Vaccinia virus

<400> SEQUENCE: 74
atatctaaaa atctt 15

<210> SEQ ID NO 75
<211> LENGTH: 15
<212> TYPE: DNA
<213> ORGANISM: Vaccinia virus

<400> SEQUENCE: 75
aaaaataatg accaa 15

<210> SEQ ID NO 76
<211> LENGTH: 15
<212> TYPE: DNA
<213> ORGANISM: Vaccinia virus

<400> SEQUENCE: 76
attattcaaa atatg 15

<210> SEQ ID NO 77
<211> LENGTH: 15
<212> TYPE: DNA
<213> ORGANISM: Vaccinia virus

<400> SEQUENCE: 77
gaaaatgaaa atata 15

<210> SEQ ID NO 78
<211> LENGTH: 15
<212> TYPE: DNA
<213> ORGANISM: Vaccinia virus

<400> SEQUENCE: 78
aaaacataaa aaaca 15

<210> SEQ ID NO 79
<211> LENGTH: 15
<212> TYPE: DNA
<213> ORGANISM: Vaccinia virus

<400> SEQUENCE: 79
aagattgaaa ttata 15

<210> SEQ ID NO 80
<211> LENGTH: 15
<212> TYPE: DNA
<213> ORGANISM: Vaccinia virus

<400> SEQUENCE: 80
aaatatgtaa atatg 15

<210> SEQ ID NO 81
<211> LENGTH: 15
<212> TYPE: DNA
<213> ORGANISM: Vaccinia virus

<400> SEQUENCE: 81
aaaactgata ttata 15

<210> SEQ ID NO 82
<211> LENGTH: 15
<212> TYPE: DNA
<213> ORGANISM: Vaccinia virus

<400> SEQUENCE: 82
ataaatgtag actct 15

<210> SEQ ID NO 83
<211> LENGTH: 15
<212> TYPE: DNA
<213> ORGANISM: Vaccinia virus

<400> SEQUENCE: 83
taaactgaag tttaa 15

<210> SEQ ID NO 84
<211> LENGTH: 53
<212> TYPE: DNA
<213> ORGANISM: Vaccinia virus

<400> SEQUENCE: 84
atttttatac cgaacataaa aataaggtta attattaata ccataaaatc atg 53

<210> SEQ ID NO 85
<211> LENGTH: 53
<212> TYPE: DNA
<213> ORGANISM: Vaccinia virus

<400> SEQUENCE: 85
ggatttttaa tagagtgaag tgatatagga ttattctttt aacaaataaa atg 53

<210> SEQ ID NO 86
<211> LENGTH: 53
<212> TYPE: DNA
<213> ORGANISM: Vaccinia virus

<400> SEQUENCE: 86
attctagaat cgttgataga acaggatgta taagttttta tgttaactaa atg 53

<210> SEQ ID NO 87
<211> LENGTH: 53
<212> TYPE: DNA
<213> ORGANISM: Vaccinia virus

<400> SEQUENCE: 87
tttgtatcat ttgtccatca acgtcatttc aataatattg gatgatataa atg 53

<210> SEQ ID NO 88
<211> LENGTH: 53
<212> TYPE: DNA
<213> ORGANISM: Vaccinia virus

<400> SEQUENCE: 88
actaaagagt taaataagtc gagatagttt tatatcactt aaatattaaa atg 53

<210> SEQ ID NO 89
<211> LENGTH: 53
<212> TYPE: DNA
<213> ORGANISM: Vaccinia virus

<400> SEQUENCE: 89
gtgcctaata ttactatatc aagtaatgct gaataaaaat atttataaat atg 53

<210> SEQ ID NO 90
<211> LENGTH: 53
<212> TYPE: DNA

<213> ORGANISM: Vaccinia virus

<400> SEQUENCE: 90
ttctactact attgatatat ttgtatttaa aagttgtttg gtgaacttaa atg 53

<210> SEQ ID NO 91
<211> LENGTH: 53
<212> TYPE: DNA
<213> ORGANISM: Vaccinia virus

<400> SEQUENCE: 91
atacaactag gactttgtca catattcttt gatctaattt ttagatataa atg 53

<210> SEQ ID NO 92
<211> LENGTH: 53
<212> TYPE: DNA
<213> ORGANISM: Vaccinia virus

<400> SEQUENCE: 92
tgtgatatgt gataaattaa ctacaaaatt aaatagaata gtaaacgacg atg 53

<210> SEQ ID NO 93
<211> LENGTH: 53
<212> TYPE: DNA
<213> ORGANISM: Vaccinia virus

<400> SEQUENCE: 93
cagtgattta ttttccagca gtaacgattt taagtttttg atacccataa atg 53

<210> SEQ ID NO 94
<211> LENGTH: 53
<212> TYPE: DNA
<213> ORGANISM: Vaccinia virus

<400> SEQUENCE: 94
aattacacgc gtttaccgat aaagtagttt tatccatttg tacgttataa atg 53

<210> SEQ ID NO 95
<211> LENGTH: 53
<212> TYPE: DNA
<213> ORGANISM: Vaccinia virus

<400> SEQUENCE: 95
aaaatataac tcgtattaaa gagttgtata tgattaattt caataactaa atg 53

<210> SEQ ID NO 96
<211> LENGTH: 53
<212> TYPE: DNA
<213> ORGANISM: Vaccinia virus

<400> SEQUENCE: 96
aattcccata ctaagagcta tttttaaaca gttatcattt catttttact atg 53

<210> SEQ ID NO 97
<211> LENGTH: 53
<212> TYPE: DNA
<213> ORGANISM: Vaccinia virus

<400> SEQUENCE: 97
taaactactg ctgtgatttt taaaacatag ttattactta tcactcataa atg 53

<210> SEQ ID NO 98
<211> LENGTH: 53

<212> TYPE: DNA
<213> ORGANISM: Vaccinia virus

<400> SEQUENCE: 98
gatatttctc tacggagttt attgtaagct ttttccattt taaatagaaa atg 53

<210> SEQ ID NO 99
<211> LENGTH: 53
<212> TYPE: DNA
<213> ORGANISM: Vaccinia virus

<400> SEQUENCE: 99
aggttttcta cttgctcatt agaagtataa aaaaatagtt ccgtaattaa atg 53

<210> SEQ ID NO 100
<211> LENGTH: 53
<212> TYPE: DNA
<213> ORGANISM: Vaccinia virus

<400> SEQUENCE: 100
aaaatgtttt tatataaaat attggacgac gagatacgta gagtgttaac atg 53

<210> SEQ ID NO 101
<211> LENGTH: 53
<212> TYPE: DNA
<213> ORGANISM: Vaccinia virus

<400> SEQUENCE: 101
agattggata ttaaaatcac gctttcgagt aaaaactacg aatataaata atg 53

<210> SEQ ID NO 102
<211> LENGTH: 53
<212> TYPE: DNA
<213> ORGANISM: Vaccinia virus

<400> SEQUENCE: 102
aactctggaa gagcacaaat aaattaaaca actaaatctg taaataaata atg 53

<210> SEQ ID NO 103
<211> LENGTH: 53
<212> TYPE: DNA
<213> ORGANISM: Vaccinia virus

<400> SEQUENCE: 103
tataatctag ttaaatcttc tgtataaata aaaatatttt tagcttctaa atg 53

<210> SEQ ID NO 104
<211> LENGTH: 53
<212> TYPE: DNA
<213> ORGANISM: Vaccinia virus

<400> SEQUENCE: 104
ctattttata tctatttatt cgcgtcctaa aattaaaaca aatgatataa atg 53

<210> SEQ ID NO 105
<211> LENGTH: 53
<212> TYPE: DNA
<213> ORGANISM: Vaccinia virus

<400> SEQUENCE: 105
gatgttgata taccaacatt taacagttta aatactgacg attattaaga atg 53

<210> SEQ ID NO 106

-continued

<211> LENGTH: 53
<212> TYPE: DNA
<213> ORGANISM: Vaccinia virus

<400> SEQUENCE: 106
ttgcacgatc gtgttatagg gcatattctg acttattttt tactacctaa atg      53

<210> SEQ ID NO 107
<211> LENGTH: 53
<212> TYPE: DNA
<213> ORGANISM: Vaccinia virus

<400> SEQUENCE: 107
aattcgaaag aaaaagaatc acagtcctaa aagctgaact tcggaaatct atg      53

<210> SEQ ID NO 108
<211> LENGTH: 53
<212> TYPE: DNA
<213> ORGANISM: Vaccinia virus

<400> SEQUENCE: 108
atctagaata tcagatcttg aaagacagtt gaacgactgt agacgtaata atg      53

<210> SEQ ID NO 109
<211> LENGTH: 53
<212> TYPE: DNA
<213> ORGANISM: Vaccinia virus

<400> SEQUENCE: 109
ttataattac ccgattgtag ttaagttttg aataaaattt tttataataa atg      53

<210> SEQ ID NO 110
<211> LENGTH: 53
<212> TYPE: DNA
<213> ORGANISM: Vaccinia virus

<400> SEQUENCE: 110
taccaaatat aaataacgca gagtgtcagt ttctaaaatc tgtactttaa atg      53

<210> SEQ ID NO 111
<211> LENGTH: 53
<212> TYPE: DNA
<213> ORGANISM: Vaccinia virus

<400> SEQUENCE: 111
tccataaaag acgaataaga tacaaacaca aatgtttata taatatttaa atg      53

<210> SEQ ID NO 112
<211> LENGTH: 53
<212> TYPE: DNA
<213> ORGANISM: Vaccinia virus

<400> SEQUENCE: 112
atgttttttc caaaaaccta agtgtattta aaatagatgc catgttaaaa atg      53

<210> SEQ ID NO 113
<211> LENGTH: 53
<212> TYPE: DNA
<213> ORGANISM: Vaccinia virus

<400> SEQUENCE: 113
tccatatttt gatttattat caaattaatt tagtaactgt aaatataatt atg      53

<210> SEQ ID NO 114
<211> LENGTH: 53
<212> TYPE: DNA
<213> ORGANISM: Vaccinia virus

<400> SEQUENCE: 114
caaaatagaa taaaataaat aacaaaggta tcattttaaa taaataaaaa atg 53

<210> SEQ ID NO 115
<211> LENGTH: 53
<212> TYPE: DNA
<213> ORGANISM: Vaccinia virus

<400> SEQUENCE: 115
gatatccatg gtatagacca aacaataacg atatatatca taaataaata atg 53

<210> SEQ ID NO 116
<211> LENGTH: 53
<212> TYPE: DNA
<213> ORGANISM: Vaccinia virus

<400> SEQUENCE: 116
taattattag aataagagtg tagtatcata gataactctc ttctataaaa atg 53

<210> SEQ ID NO 117
<211> LENGTH: 53
<212> TYPE: DNA
<213> ORGANISM: Vaccinia virus

<400> SEQUENCE: 117
tatacataga tataattatc acatattaaa aattcacaca tttttgataa atg 53

<210> SEQ ID NO 118
<211> LENGTH: 53
<212> TYPE: DNA
<213> ORGANISM: Vaccinia virus

<400> SEQUENCE: 118
acataaaaac tcattacata gttgataaaa agcggtagga tataaatatt atg 53

<210> SEQ ID NO 119
<211> LENGTH: 53
<212> TYPE: DNA
<213> ORGANISM: Vaccinia virus

<400> SEQUENCE: 119
tagttctggt attttactaa ttactaaatc tgtatatctt tccatttatc atg 53

<210> SEQ ID NO 120
<211> LENGTH: 53
<212> TYPE: DNA
<213> ORGANISM: Vaccinia virus

<400> SEQUENCE: 120
cgacgctgtt ctgcagccat ttaactttaa ataatttaca aaaatttaaa atg 53

<210> SEQ ID NO 121
<211> LENGTH: 53
<212> TYPE: DNA
<213> ORGANISM: Vaccinia virus

<400> SEQUENCE: 121
tttgtaacat cggtacgggt attcatttat cacaaaaaaa acttctctaa atg 53

<210> SEQ ID NO 122
<211> LENGTH: 53
<212> TYPE: DNA
<213> ORGANISM: Vaccinia virus

<400> SEQUENCE: 122
tagtaaaccg atagtgtata aagattgtgc aaagcttttg cgatcaataa atg 53

<210> SEQ ID NO 123
<211> LENGTH: 53
<212> TYPE: DNA
<213> ORGANISM: Vaccinia virus

<400> SEQUENCE: 123
ctacggatgg atgatataga tctttacaca aataattaca aaaccgataa atg 53

<210> SEQ ID NO 124
<211> LENGTH: 53
<212> TYPE: DNA
<213> ORGANISM: Vaccinia virus

<400> SEQUENCE: 124
atctccgtaa atatatgctc atatatttat agaagatatc acatatctaa atg 53

<210> SEQ ID NO 125
<211> LENGTH: 53
<212> TYPE: DNA
<213> ORGANISM: Vaccinia virus

<400> SEQUENCE: 125
gataaatacg aatatctgtc ttatatttat aatatgctag ttaatagtaa atg 53

<210> SEQ ID NO 126
<211> LENGTH: 53
<212> TYPE: DNA
<213> ORGANISM: Vaccinia virus

<400> SEQUENCE: 126
caatattgaa aatactaatt gtttaaataa cccgagtatt gaaactatat atg 53

<210> SEQ ID NO 127
<211> LENGTH: 53
<212> TYPE: DNA
<213> ORGANISM: Vaccinia virus

<400> SEQUENCE: 127
tatttttgtg ttaaaacaat gaactaatat ttattttgt acattaataa atg 53

<210> SEQ ID NO 128
<211> LENGTH: 53
<212> TYPE: DNA
<213> ORGANISM: Vaccinia virus

<400> SEQUENCE: 128
gatacgatac tatatgtatt cttcgatagt ccgcattatg tacctattct atg 53

<210> SEQ ID NO 129
<211> LENGTH: 53
<212> TYPE: DNA
<213> ORGANISM: Vaccinia virus

<400> SEQUENCE: 129
caagtttatt ccaatagatg tcttattaaa aacatatata ataaataaca atg 53

<210> SEQ ID NO 130
<211> LENGTH: 53
<212> TYPE: DNA
<213> ORGANISM: Vaccinia virus

<400> SEQUENCE: 130
aactggtaat taaaataaaa agtaatattc atatgtagtg tcaattttaa atg 53

<210> SEQ ID NO 131
<211> LENGTH: 53
<212> TYPE: DNA
<213> ORGANISM: Vaccinia virus

<400> SEQUENCE: 131
tttttgatgg tggtttaacg ttttaaaaaa agattttgtt attgtagtat atg 53

<210> SEQ ID NO 132
<211> LENGTH: 53
<212> TYPE: DNA
<213> ORGANISM: Vaccinia virus

<400> SEQUENCE: 132
taacattgtt aattgaaaag ggataacatg ttacagaata taaattatat atg 53

<210> SEQ ID NO 133
<211> LENGTH: 53
<212> TYPE: DNA
<213> ORGANISM: Vaccinia virus

<400> SEQUENCE: 133
tgcatattat acactggtta acgcccttat aggctctaac cattttcaag atg 53

<210> SEQ ID NO 134
<211> LENGTH: 53
<212> TYPE: DNA
<213> ORGANISM: Vaccinia virus

<400> SEQUENCE: 134
ttgcagtgtt catctcccaa ctgcaagtga aggattgata actgaaggca atg 53

<210> SEQ ID NO 135
<211> LENGTH: 53
<212> TYPE: DNA
<213> ORGANISM: Vaccinia virus

<400> SEQUENCE: 135
ctcttctccc tttcccagaa acaaactttt tttacccact ataaaataaa atg 53

<210> SEQ ID NO 136
<211> LENGTH: 53
<212> TYPE: DNA
<213> ORGANISM: Vaccinia virus

<400> SEQUENCE: 136
aatagtataa actaaaaatt aaacaaatcg ttattataag taatatcaaa atg 53

<210> SEQ ID NO 137
<211> LENGTH: 53
<212> TYPE: DNA
<213> ORGANISM: Vaccinia virus

<400> SEQUENCE: 137
ttctgttttt ctttcacatc tttaattatg aaaaagtaaa tcattatgag atg 53

<210> SEQ ID NO 138
<211> LENGTH: 53
<212> TYPE: DNA
<213> ORGANISM: Vaccinia virus

<400> SEQUENCE: 138
cacttactaa atagccaagg tgattattcg tattttttta aggagtaacc atg 53

<210> SEQ ID NO 139
<211> LENGTH: 53
<212> TYPE: DNA
<213> ORGANISM: Vaccinia virus

<400> SEQUENCE: 139
ttttattatt tgtacgatgt ccaggataac atttttacgg ataaataaat atg 53

<210> SEQ ID NO 140
<211> LENGTH: 53
<212> TYPE: DNA
<213> ORGANISM: Vaccinia virus

<400> SEQUENCE: 140
tagtttcttg gaaaaattta ttatgagaga cattttctca gactggataa atg 53

<210> SEQ ID NO 141
<211> LENGTH: 53
<212> TYPE: DNA
<213> ORGANISM: Vaccinia virus

<400> SEQUENCE: 141
tctatcaaac ctggactttc gtttgtaaat tggggctttt tgtacaataa atg 53

<210> SEQ ID NO 142
<211> LENGTH: 53
<212> TYPE: DNA
<213> ORGANISM: Vaccinia virus

<400> SEQUENCE: 142
atgaatatga tgaagatagc gataaagaaa agccaatatt caatgtataa atg 53

<210> SEQ ID NO 143
<211> LENGTH: 53
<212> TYPE: DNA
<213> ORGANISM: Vaccinia virus

<400> SEQUENCE: 143
aacgcagttt ggaaaaaaga agatatctgg taaattcttt tccatgataa atg 53

<210> SEQ ID NO 144
<211> LENGTH: 53
<212> TYPE: DNA
<213> ORGANISM: Vaccinia virus

<400> SEQUENCE: 144
tacgatgata acgacatacg aacattactt cctattttac tccttagtaa atg 53

<210> SEQ ID NO 145
<211> LENGTH: 53
<212> TYPE: DNA
<213> ORGANISM: Vaccinia virus

<400> SEQUENCE: 145
atcttctgta agtaggaatt tggacaagtt gaacaaaatt agatctctaa atg 53

<210> SEQ ID NO 146
<211> LENGTH: 53
<212> TYPE: DNA
<213> ORGANISM: Vaccinia virus

<400> SEQUENCE: 146
atttttatac ggatgctcat tttaaatttt tgtaaattat ttaaagttaa atg 53

<210> SEQ ID NO 147
<211> LENGTH: 53
<212> TYPE: DNA
<213> ORGANISM: Vaccinia virus

<400> SEQUENCE: 147
atgaggtttt ctagcagtag actcatttag agaagttttt tttgtgataa atg 53

<210> SEQ ID NO 148
<211> LENGTH: 53
<212> TYPE: DNA
<213> ORGANISM: Vaccinia virus

<400> SEQUENCE: 148
ttattacaac tataaaaata atagttatat ttacacttta aatttttatc atg 53

<210> SEQ ID NO 149
<211> LENGTH: 53
<212> TYPE: DNA
<213> ORGANISM: Vaccinia virus

<400> SEQUENCE: 149
taaaaaaatt atacatcata aaccaatttc ctagttgttt gtaactttaa atg 53

<210> SEQ ID NO 150
<211> LENGTH: 53
<212> TYPE: DNA
<213> ORGANISM: Vaccinia virus

<400> SEQUENCE: 150
cgttatcgtc gttatctact ttgggatact tattatcctt aactataaaa atg 53

<210> SEQ ID NO 151
<211> LENGTH: 53
<212> TYPE: DNA
<213> ORGANISM: Vaccinia virus

<400> SEQUENCE: 151
tatattagcg ctagacatat tacagaacta ttttagatta tgatatttaa atg 53

<210> SEQ ID NO 152
<211> LENGTH: 53
<212> TYPE: DNA
<213> ORGANISM: Vaccinia virus

<400> SEQUENCE: 152
aagacttaca tcatcggtag tagattttca ctttacccca cgatataaat atg 53

<210> SEQ ID NO 153
<211> LENGTH: 53
<212> TYPE: DNA
<213> ORGANISM: Vaccinia virus

<400> SEQUENCE: 153
aaaatctaaa tatgacagat ggtgactctg tctcttttga tgatgaataa atg 53

<210> SEQ ID NO 154
<211> LENGTH: 53
<212> TYPE: DNA
<213> ORGANISM: Vaccinia virus

<400> SEQUENCE: 154
atcgttttgt atatccgtca ctggtacggt cgtcatttaa tactaaataa atg 53

<210> SEQ ID NO 155
<211> LENGTH: 53
<212> TYPE: DNA
<213> ORGANISM: Vaccinia virus

<400> SEQUENCE: 155
aaaagatgat atattgcata cttgatcaat agtgaagtta ttgtcaataa atg 53

<210> SEQ ID NO 156
<211> LENGTH: 53
<212> TYPE: DNA
<213> ORGANISM: Vaccinia virus

<400> SEQUENCE: 156
gtttatattc cactttgttc attcggcgat ttaaaatttt tattagttaa atg 53

<210> SEQ ID NO 157
<211> LENGTH: 53
<212> TYPE: DNA
<213> ORGANISM: Vaccinia virus

<400> SEQUENCE: 157
attcgtatta tttgagcaag aaaatatccc accacctttt cgtctagtaa atg 53

<210> SEQ ID NO 158
<211> LENGTH: 53
<212> TYPE: DNA
<213> ORGANISM: Vaccinia virus

<400> SEQUENCE: 158
ggcataaaga ttatactcca tctttaatag tgacattttt taatatataa atg 53

<210> SEQ ID NO 159
<211> LENGTH: 53
<212> TYPE: DNA
<213> ORGANISM: Vaccinia virus

<400> SEQUENCE: 159
tgtacagact aagtaattct tttaagttag ttaaatcagc gctagaagtc atg 53

<210> SEQ ID NO 160
<211> LENGTH: 53
<212> TYPE: DNA
<213> ORGANISM: Vaccinia virus

<400> SEQUENCE: 160
acttaactct tttgttaatt aaaagtatat tcaaaaaatg agttatataa atg 53

<210> SEQ ID NO 161
<211> LENGTH: 53
<212> TYPE: DNA
<213> ORGANISM: Vaccinia virus

<400> SEQUENCE: 161
cattgtctga tgcgtgtaaa aaaattttgt cagcttctaa tagattataa atg 53

<210> SEQ ID NO 162
<211> LENGTH: 53
<212> TYPE: DNA
<213> ORGANISM: Vaccinia virus

<400> SEQUENCE: 162
tgtatgtaaa aatatagtag aatttcattt tgtttttttc tatgctataa atg 53

<210> SEQ ID NO 163
<211> LENGTH: 53
<212> TYPE: DNA
<213> ORGANISM: Vaccinia virus

<400> SEQUENCE: 163
taatgcaccg aacatccatt tatagaattt agaaatatat tttcatttaa atg 53

<210> SEQ ID NO 164
<211> LENGTH: 53
<212> TYPE: DNA
<213> ORGANISM: Vaccinia virus

<400> SEQUENCE: 164
agaacctcaa cgtaacttaa cagtgcaacc tctattggat ataaactaat atg 53

<210> SEQ ID NO 165
<211> LENGTH: 53
<212> TYPE: DNA
<213> ORGANISM: Vaccinia virus

<400> SEQUENCE: 165
gatcaacatc tttatggcgt ttttagatta atactttcaa tgagataaat atg 53

<210> SEQ ID NO 166
<211> LENGTH: 53
<212> TYPE: DNA
<213> ORGANISM: Vaccinia virus

<400> SEQUENCE: 166
tcagtttatt atctctcttg gtaatatgga tactaattgt agctatttaa atg 53

<210> SEQ ID NO 167
<211> LENGTH: 53
<212> TYPE: DNA
<213> ORGANISM: Vaccinia virus

<400> SEQUENCE: 167
aaaagaatat tcctctaaca gatattccga caaaggattg attactataa atg 53

<210> SEQ ID NO 168
<211> LENGTH: 53
<212> TYPE: DNA
<213> ORGANISM: Vaccinia virus

<400> SEQUENCE: 168
gtagtagtaa gtatttatac aaacttttct tatccattta taacgtacaa atg 53

<210> SEQ ID NO 169
<211> LENGTH: 53
<212> TYPE: DNA

<213> ORGANISM: Vaccinia virus

<400> SEQUENCE: 169
agggaaaatc taaagttgtt cgtaaaaaag ttaaaacttg taagaagtaa atg 53

<210> SEQ ID NO 170
<211> LENGTH: 53
<212> TYPE: DNA
<213> ORGANISM: Vaccinia virus

<400> SEQUENCE: 170
ataaaatact actgttgagt aaatcagtta ttttttttat atcgatattg atg 53

<210> SEQ ID NO 171
<211> LENGTH: 53
<212> TYPE: DNA
<213> ORGANISM: Vaccinia virus

<400> SEQUENCE: 171
ttgatcaaga gtaactattg acttaatagg catcatttat ttagtattaa atg 53

<210> SEQ ID NO 172
<211> LENGTH: 53
<212> TYPE: DNA
<213> ORGANISM: Vaccinia virus

<400> SEQUENCE: 172
ccaatttcca tctaatatac tttgtcggat tatctatagt acacggaata atg 53

<210> SEQ ID NO 173
<211> LENGTH: 53
<212> TYPE: DNA
<213> ORGANISM: Vaccinia virus

<400> SEQUENCE: 173
ccattgctgc cactcataat atcagactac ttattctatt ttactaaata atg 53

<210> SEQ ID NO 174
<211> LENGTH: 53
<212> TYPE: DNA
<213> ORGANISM: Vaccinia virus

<400> SEQUENCE: 174
tttgtataaa taattatttc aatatactag ttaaaatttt aagattttaa atg 53

<210> SEQ ID NO 175
<211> LENGTH: 53
<212> TYPE: DNA
<213> ORGANISM: Vaccinia virus

<400> SEQUENCE: 175
tccatccaca gacgttaccg aaccgattag tgatgtgaca ccatcggtgg atg 53

<210> SEQ ID NO 176
<211> LENGTH: 53
<212> TYPE: DNA
<213> ORGANISM: Vaccinia virus

<400> SEQUENCE: 176
atacgaggac gtgtatagag taagtaaaga aaaagaatgt ggaatttgct atg 53

<210> SEQ ID NO 177
<211> LENGTH: 2652

<212> TYPE: DNA
<213> ORGANISM: Bacteriophage T7

<400> SEQUENCE: 177

```
atgaacacga ttaacatcgc taagaacgac ttctctgaca tcgaactggc tgctatcccg     60
ttcaacactc tggctgacca ttacggtgag cgtttagctc gcgaacagtt ggcccttgag    120
catgagtctt acgagatggg tgaagcacgc ttccgcaaga tgtttgagcg tcaacttaaa    180
gctggtgagg ttgcggataa cgctgccgcc aagcctctca tcactaccct actccctaag    240
atgattgcac gcatcaacga ctggtttgag gaagtgaaag ctaagcgcgg caagcgcccg    300
acagccttcc agttcctgca agaaatcaag ccggaagccg tagcgtacat caccattaag    360
accactctgg cttgcctaac cagtgctgac aatacaaccg ttcaggctgt agcaagcgca    420
atcggtcggg ccattgagga cgaggctcgc ttcggtcgta tccgtgacct tgaagctaag    480
cacttcaaga aaaacgttga ggaacaactc aacaagcgcg tagggcacgt ctacaagaaa    540
gcatttatgc aagttgtcga ggctgacatg ctctctaagg gtctactcgg tggcgaggcg    600
tggtcttcgt ggcataagga agactctatt catgtaggag tacgctgcat cgagatgctc    660
attgagtcaa ccggaatggt tagcttacac cgccaaaatg ctggcgtagt aggtcaagac    720
tctgagacta tcgaactcgc acctgaatac gctgaggcta tcgcaacccg tgcaggtgcg    780
ctggctggca tctctccgat gttccaacct tgcgtagttc ctcctaagcc gtggactggc    840
attactggtg gtggctattg ggctaacggt cgtcgtcctc tggcgctggt gcgtactcac    900
agtaagaaag cactgatgcg ctacgaagac gtttacatgc ctgaggtgta caaagcgatt    960
aacattgcgc aaaacaccgc atggaaaatc aacaagaaag tcctagcggt cgccaacgta   1020
atcaccaagt ggaagcattg tccggtcgag gacatccctg cgattgagcg tgaagaactc   1080
ccgatgaaac cggaagacat cgacatgaat cctgaggctc tcaccgcgtg gaaacgtgct   1140
gccgctgctg tgtaccgcaa ggacaaggct cgcaagtctc gccgtatcag ccttgagttc   1200
atgcttgagc aagccaataa gtttgctaac cataaggcca tctggttccc ttacaacatg   1260
gactggcgcg gtcgtgttta cgctgtgtca atgttcaacc cgcaaggtaa cgatatgacc   1320
aaaggactgc ttacgctggc gaaaggtaaa ccaatcggta aggaaggtta ctactggctg   1380
aaaatccacg gtgcaaactg tgcgggtgtc gataaggttc cgttccctga gcgcatcaag   1440
ttcattgagg aaaaccacga gaacatcatg gcttgcgcta agtctccact ggagaacact   1500
tggtgggctg agcaagattc tccgttctgc ttccttgcgt tctgctttga gtacgctggg   1560
gtacagcacc acggcctgag ctataactgc tcccttccgc tggcgtttga cgggtcttgc   1620
tctggcatcc agcacttctc cgcgatgctc cgagatgagg taggtggtcg cgcggttaac   1680
ttgcttccta gtgaaaccgt tcaggacatc tacgggattg ttgctaagaa agtcaacgag   1740
attctacaag cagacgcaat caatgggacc gataacgaag tagttaccgt gaccgatgag   1800
aacactggtg aaatctctga gaaagtcaag ctgggcacta aggcactggc tggtcaatgg   1860
ctggcttacg gtgttactcg cagtgtgact aagcgttcag tcatgacgct ggcttacggg   1920
tccaaagagt tcggcttccg tcaacaagtg ctggaagata ccattcagcc agctattgat   1980
tccggcaagg gtctgatgtt cactcagccg aatcaggctg ctggatacat ggctaagctg   2040
atttgggaat ctgtgagcgt gacggtggta gctgcggttg aagcaatgaa ctggcttaag   2100
tctgctgcta agctgctggc tgctgaggtc aaagataaga agactggaga gattcttcgc   2160
aagcgttgcg ctgtgcattg ggtaactcct gatggtttcc ctgtgtggca ggaatacaag   2220
```

```
aagcctattc agacgcgctt gaacctgatg ttcctcggtc agttccgctt acagcctacc   2280

attaacacca acaaagatag cgagattgat gcacacaaac aggagtctgg tatcgctcct   2340

aactttgtac acagccaaga cggtagccac cttcgtaaga ctgtagtgtg ggcacacgag   2400

aagtacggaa tcgaatcttt tgcactgatt cacgactcct tcggtaccat tccggctgac   2460

gctgcgaacc tgttcaaagc agtgcgcgaa actatggttg acacatatga gtcttgtgat   2520

gtactggctg atttctacga ccagttcgct gaccagttgc acgagtctca attggacaaa   2580

atgccagcac ttccggctaa aggtaacttg aacctccgtg acatcttaga gtcggacttc   2640

gcgttcgcgt aa                                                       2652


<210> SEQ ID NO 178
<211> LENGTH: 883
<212> TYPE: PRT
<213> ORGANISM: Bacteriophage T7

<400> SEQUENCE: 178

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
```

-continued

```
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
        355                 360                 365

Met Asn Pro Glu Ala Leu Thr Ala Trp Lys Arg Ala Ala Ala Ala Val
    370                 375                 380

Tyr Arg Lys Asp Arg Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
        435                 440                 445

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala His Gly
    610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Pro Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Ala Ala Lys
    690                 695                 700

Leu Leu Ala Ala Glu Val Lys Asp Lys Lys Thr Gly Glu Ile Leu Arg
705                 710                 715                 720
```

-continued

```
Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala


<210> SEQ ID NO 179
<211> LENGTH: 2622
<212> TYPE: DNA
<213> ORGANISM: Bacteriophage SP6

<400> SEQUENCE: 179

atgcaagatt tacacgctat ccagcttcaa ttagaagaag agatgtttaa tggtggcatt      60

cgtcgcttcg aagcagatca acaacgccag attgcagcag gtagcgagag cgacacagca     120

tggaaccgcc gcctgttgtc agaacttatt gcacctatgg ctgaaggcat tcaggcttat     180

aaagaagagt acgaaggtaa gaaaggtcgt gcacctcgcg cattggcttt cttacaatgt     240

gtagaaaatg aagttgcagc atacatcact atgaaagttg ttatggatat gctgaatacg     300

gatgctaccc ttcaggctat tgcaatgagt gtagcagaac gcattgaaga ccaagtgcgc     360

ttttctaagc tagaaggtca cgccgctaaa tactttgaga aggttaagaa gtcactcaag     420

gctagccgta ctaagtcata tcgtcacgct cataacgtag ctgtagttgc tgaaaaatca     480

gttgcagaaa aggacgcgga ctttgaccgt tgggaggcgt ggccaaaaga aactcaattg     540

cagattggta ctaccttgct tgaaatctta gaaggtagcg ttttctataa tggtgaacct     600

gtatttatgc gtgctatgcg cacttatggc ggaaagacta tttactactt acaaacttct     660

gaaagtgtag gccagtggat tagcgcattc aaagagcacg tagcgcaatt aagcccagct     720

tatgcccctt gcgtaatccc tcctcgtcct tggagaactc catttaatgg agggttccat     780

actgagaagg tagctagccg tatccgtctt gtaaaaggta accgtgagca tgtacgcaag     840

ttgactcaaa agcaaatgcc aaaggtttat aaggctatca acgcattaca aaatacacaa     900

tggcaaatca acaaggatgt attagcagtt attgaagaag taatccgctt agaccttggt     960

tatggtgtac cttccttcaa gccactgatt gacaaggaga acaagccagc taacccggta    1020

cctgttgaat tccaacacct gcgcggtcgt gaactgaaag agatgctatc acctgagcag    1080

tggcaacaat tcattaactg gaaaggcgaa tgcgcgcgcc tatataccgc agaaactaag    1140
```

cgcggttcaa agtccgccgc cgttgttcgc atggtaggac aggcccgtaa atatagcgcc 1200
tttgaatcca tttacttcgt gtacgcaatg gatagccgca gccgtgtcta tgtgcaatct 1260
agcacgctct ctccgcagtc taacgactta ggtaaggcat tactccgctt taccgaggga 1320
cgccctgtga atggcgtaga agcgcttaaa tggttctgca tcaatggtgc taacctttgg 1380
ggatgggaca agaaaacttt tgatgtgcgc gtgtctaacg tattagatga ggaattccaa 1440
gatatgtgtc gagacatcgc cgcagaccct ctcacattca cccaatgggc taaagctgat 1500
gcaccttatg aattcctcgc ttggtgcttt gagtatgctc aataccttga tttggtggat 1560
gaaggaaggg ccgacgaatt ccgcactcac ctaccagtac atcaggacgg gtcttgttca 1620
ggcattcagc actatagtgc tatgcttcgc gacgaagtag gggccaaagc tgttaacctg 1680
aaaccctccg atgcaccgca ggatatctat ggggcggtgg cgcaagtggt tatcaagaag 1740
aatgcgctat atatggatgc ggacgatgca accacgttta cttctggtag cgtcacgctg 1800
tccggtacag aactgcgagc aatggctagc gcatgggata gtattggtat tacccgtagc 1860
ttaaccaaaa agcccgtgat gaccttgcca tatggttcta ctcgcttaac ttgccgtgaa 1920
tctgtgattg attacatcgt agacttagag gaaaaagagg cgcagaaggc agtagcagaa 1980
gggcggacgg caaacaaggt acatcctttt gaagacgatc gtcaagatta cttgactccg 2040
ggcgcagctt acaactacat gacggcacta atctggcctt ctatttctga agtagttaag 2100
gcaccgatag tagctatgaa gatgatacgc cagcttgcac gctttgcagc gaaacgtaat 2160
gaaggcctga tgtacaccct gcctactggc ttcatcttag aacagaagat catggcaacc 2220
gagatgctac gcgtgcgtac ctgtctgatg ggtgatatca agatgtccct tcaggttgaa 2280
acggatatcg tagatgaagc cgctatgatg ggagcagcag cacctaattt cgtacacggt 2340
catgacgcaa gtcaccttat ccttaccgta tgtgaattgg tagacaaggg cgtaactagt 2400
atcgctgtaa tccacgactc ttttggtact catgcagaca acaccctcac tcttagagtg 2460
gcacttaaag ggcagatggt tgcaatgtat attgatggta atgcgcttca gaaactactg 2520
gaggagcatg aagtgcgctg gatggttgat acaggtatcg aagtacctga gcaaggggag 2580
ttcgacctta acgaaatcat ggattctgaa tacgtatttg cc 2622

<210> SEQ ID NO 180
<211> LENGTH: 874
<212> TYPE: PRT
<213> ORGANISM: Bacteriophage SP6

<400> SEQUENCE: 180

Met Gln Asp Leu His Ala Ile Gln Leu Gln Leu Glu Glu Glu Met Phe
1               5                   10                  15

Asn Gly Gly Ile Arg Arg Phe Glu Ala Asp Gln Gln Arg Gln Ile Ala
            20                  25                  30

Ala Gly Ser Glu Ser Asp Thr Ala Trp Asn Arg Arg Leu Leu Ser Glu
        35                  40                  45

Leu Ile Ala Pro Met Ala Glu Gly Ile Gln Ala Tyr Lys Glu Glu Tyr
    50                  55                  60

Glu Gly Lys Lys Gly Arg Ala Pro Arg Ala Leu Ala Phe Leu Gln Cys
65                  70                  75                  80

Val Glu Asn Glu Val Ala Ala Tyr Ile Thr Met Lys Val Val Met Asp
                85                  90                  95

Met Leu Asn Thr Asp Ala Thr Leu Gln Ala Ile Ala Met Ser Val Ala
            100                 105                 110

-continued

```
Glu Arg Ile Glu Asp Gln Val Arg Phe Ser Lys Leu Glu Gly His Ala
        115                 120                 125

Ala Lys Tyr Phe Glu Lys Val Lys Lys Ser Leu Lys Ala Ser Arg Thr
    130                 135                 140

Lys Ser Tyr Arg His Ala His Asn Val Ala Val Val Ala Glu Lys Ser
145                 150                 155                 160

Val Ala Glu Lys Asp Ala Asp Phe Asp Arg Trp Glu Ala Trp Pro Lys
                165                 170                 175

Glu Thr Gln Leu Gln Ile Gly Thr Thr Leu Leu Glu Ile Leu Glu Gly
            180                 185                 190

Ser Val Phe Tyr Asn Gly Glu Pro Val Phe Met Arg Ala Met Arg Thr
        195                 200                 205

Tyr Gly Gly Lys Thr Ile Tyr Tyr Leu Gln Thr Ser Glu Ser Val Gly
    210                 215                 220

Gln Trp Ile Ser Ala Phe Lys Glu His Val Ala Gln Leu Ser Pro Ala
225                 230                 235                 240

Tyr Ala Pro Cys Val Ile Pro Pro Arg Pro Trp Arg Thr Pro Phe Asn
                245                 250                 255

Gly Gly Phe His Thr Glu Lys Val Ala Ser Arg Ile Arg Leu Val Lys
            260                 265                 270

Gly Asn Arg Glu His Val Arg Lys Leu Thr Gln Lys Gln Met Pro Lys
        275                 280                 285

Val Tyr Lys Ala Ile Asn Ala Leu Gln Asn Thr Gln Trp Gln Ile Asn
    290                 295                 300

Lys Asp Val Leu Ala Val Ile Glu Glu Val Ile Arg Leu Asp Leu Gly
305                 310                 315                 320

Tyr Gly Val Pro Ser Phe Lys Pro Leu Ile Asp Lys Glu Asn Lys Pro
                325                 330                 335

Ala Asn Pro Val Pro Val Glu Phe Gln His Leu Arg Gly Arg Glu Leu
            340                 345                 350

Lys Glu Met Leu Ser Pro Glu Gln Trp Gln Gln Phe Ile Asn Trp Lys
        355                 360                 365

Gly Glu Cys Ala Arg Leu Tyr Thr Ala Glu Thr Lys Arg Gly Ser Lys
    370                 375                 380

Ser Ala Ala Val Val Arg Met Val Gly Gln Ala Arg Lys Tyr Ser Ala
385                 390                 395                 400

Phe Glu Ser Ile Tyr Phe Val Tyr Ala Met Asp Ser Arg Ser Arg Val
                405                 410                 415

Tyr Val Gln Ser Ser Thr Leu Ser Pro Gln Ser Asn Asp Leu Gly Lys
            420                 425                 430

Ala Leu Leu Arg Phe Thr Glu Gly Arg Pro Val Asn Gly Val Glu Ala
        435                 440                 445

Leu Lys Trp Phe Cys Ile Asn Gly Ala Asn Leu Trp Gly Trp Asp Lys
    450                 455                 460

Lys Thr Phe Asp Val Arg Val Ser Asn Val Leu Asp Glu Glu Phe Gln
465                 470                 475                 480

Asp Met Cys Arg Asp Ile Ala Ala Asp Pro Leu Thr Phe Thr Gln Trp
                485                 490                 495

Ala Lys Ala Asp Ala Pro Tyr Glu Phe Leu Ala Trp Cys Phe Glu Tyr
            500                 505                 510

Ala Gln Tyr Leu Asp Leu Val Asp Glu Gly Arg Ala Asp Glu Phe Arg
        515                 520                 525

Thr His Leu Pro Val His Gln Asp Gly Ser Cys Ser Gly Ile Gln His
```

-continued

```
    530                 535                 540

Tyr Ser Ala Met Leu Arg Asp Glu Val Gly Ala Lys Ala Val Asn Leu
545                 550                 555                 560

Lys Pro Ser Asp Ala Pro Gln Asp Ile Tyr Gly Ala Val Ala Gln Val
                565                 570                 575

Val Ile Lys Lys Asn Ala Leu Tyr Met Asp Ala Asp Asp Ala Thr Thr
            580                 585                 590

Phe Thr Ser Gly Ser Val Thr Leu Ser Gly Thr Glu Leu Arg Ala Met
        595                 600                 605

Ala Ser Ala Trp Asp Ser Ile Gly Ile Thr Arg Ser Leu Thr Lys Lys
    610                 615                 620

Pro Val Met Thr Leu Pro Tyr Gly Ser Thr Arg Leu Thr Cys Arg Glu
625                 630                 635                 640

Ser Val Ile Asp Tyr Ile Val Asp Leu Glu Glu Lys Glu Ala Gln Lys
                645                 650                 655

Ala Val Ala Glu Gly Arg Thr Ala Asn Lys Val His Pro Phe Glu Asp
            660                 665                 670

Asp Arg Gln Asp Tyr Leu Thr Pro Gly Ala Ala Tyr Asn Tyr Met Thr
        675                 680                 685

Ala Leu Ile Trp Pro Ser Ile Ser Glu Val Val Lys Ala Pro Ile Val
    690                 695                 700

Ala Met Lys Met Ile Arg Gln Leu Ala Arg Phe Ala Ala Lys Arg Asn
705                 710                 715                 720

Glu Gly Leu Met Tyr Thr Leu Pro Thr Gly Phe Ile Leu Glu Gln Lys
                725                 730                 735

Ile Met Ala Thr Glu Met Leu Arg Val Arg Thr Cys Leu Met Gly Asp
            740                 745                 750

Ile Lys Met Ser Leu Gln Val Glu Thr Asp Ile Val Asp Glu Ala Ala
        755                 760                 765

Met Met Gly Ala Ala Ala Pro Asn Phe Val His Gly His Asp Ala Ser
    770                 775                 780

His Leu Ile Leu Thr Val Cys Glu Leu Val Asp Lys Gly Val Thr Ser
785                 790                 795                 800

Ile Ala Val Ile His Asp Ser Phe Gly Thr His Ala Asp Asn Thr Leu
                805                 810                 815

Thr Leu Arg Val Ala Leu Lys Gly Gln Met Val Ala Met Tyr Ile Asp
            820                 825                 830

Gly Asn Ala Leu Gln Lys Leu Leu Glu Glu His Glu Val Arg Trp Met
        835                 840                 845

Val Asp Thr Gly Ile Glu Val Pro Glu Gln Gly Glu Phe Asp Leu Asn
    850                 855                 860

Glu Ile Met Asp Ser Glu Tyr Val Phe Ala
865                 870


<210> SEQ ID NO 181
<211> LENGTH: 2655
<212> TYPE: DNA
<213> ORGANISM: Bacteriophage T3

<400> SEQUENCE: 181

atgaacatca tcgaaaacat cgaaaagaat gacttctcag aaatcgaact ggctgctatc      60

ccgttcaaca cactggctga ccactacgga agcgccttgg ctaaagagca gttggcttta     120

gaacatgagt cttatgagct aggcgagcgc cgcttcctca agatgcttga gcgtcaagcg     180
```

-continued

```
aaagctggtg agattgcaga caacgcagcc gctaagccgt tactcgctac gcttctccct    240
aagttaacca cacgtatcgt cgagtggctc gaagagtacg catcgaagaa aggccgcaag    300
cctagcgcat acgcaccgct ccagttactc aagccggagg cctccgcgtt tatcaccctg    360
aaagttatcc ttgcgtcact aaccagtacg aacatgacaa ccattcaggc cgctgctggt    420
atgctgggga aagccattga ggacgaggca cgatttgggc gcatccgtga cctagaagcg    480
aagcacttca agaagcacgt tgaggaacag cttaacaagc gccacgggca agtctacaag    540
aaagcattta tgcaggtggt cgaggccgat atgattggtc gaggtctgct tggtggcgag    600
gcgtggtcta gctgggataa agaaaccacg atgcacgtag ggattcgcct gattgaaatg    660
ctgattgaat ccacgggtct ggtggaatta cagcgccaca acgcaggtaa cgcaggctct    720
gaccatgagg cactgcaact ggcccaagag tacgtggacg tattagcgaa gcgtgcaggc    780
gctctggcgg gtatctctcc gatgttccag ccgtgtgtcg taccgccgaa accttgggta    840
gcaatcacag ggggcggcta ttgggctaac ggtcgcagac ctttggcact cgttcgcact    900
cactctaaga agggcttgat gcgctacgaa gacgtttaca tgccagaagt ctacaaggct    960
gtgaacctcg cgcaaaacac cgcatggaaa atcaacaaga aagttcttgc tgttgtcaat   1020
gagattgtta actggaagaa ttgcccggta gcagacattc catcgctgga gcgccaagag   1080
ttaccgccta agcctgacga cattgacacc aacgaggcag cgctcaagga gtggaagaaa   1140
gccgctgctg gtatctatcg cttggacaag gcacgagtgt ctcgccgtat cagcttagag   1200
ttcatgctgg agcaggccaa caagttcgca agtaagaaag caatctggtt cccttacaac   1260
atggactggc gcggtcgtgt gtacgctgtg ccgatgttca acccgcaagg caacgacatg   1320
acgaaaggtc tgctgaccct tgctaaaggc aagccaatcg gtgaggaagg tttctactgg   1380
ctgaaaatcc acggtgcgaa ctgtgcgggt gttgataagg ttccattccc ggagcgcatc   1440
gcgttcattg agaagcacgt agacgacatt ctggcttgcg ctaaagaccc aatcaataac   1500
acttggtggg ctgagcagga ttcaccgttc tgtttcctcg cgttttgctt cgagtatgca   1560
ggcgttacgc accacggtct gagctacaat tgctctctgc cgctggcgtt cgacgggtct   1620
tgctctggta tccagcactt ctccgcgatg ctccgcgatg aggtaggcgg tcgtgcggtt   1680
aacctgctgc caagcgaaac cgtgcaggac atttacggca tcgttgcaca gaaagtaaac   1740
gagattctca aacaggatgc aatcaacggc acgcctaacg agatgattac cgtgaccgac   1800
aaggacaccg gggaaatctc agagaagctc aaacttggaa cctcaacgct ggcgcaacag   1860
tggctggcat atggtgtaac ccgtagcgta actaaacgtt cggtcatgac gctggcttac   1920
ggttccaagg agttcggctt tcgtcaacag gtattggatg acaccattca gcctgcaatt   1980
gacagcggta agggcttgat gttcacccaa ccgaaccaag cggctggcta tatggctaag   2040
ctgatttggg atgcggtaag cgtgaccgta gttgcagcgg ttgaggcgat gaactggctc   2100
aaatctgccg ctaagctgct ggctgctgag gtcaaggaca agaagaccaa ggagattctg   2160
cgccaccgtt gcgcggttca ctggactacg ccggacggct tcccggtctg gcaggaatac   2220
cgcaagccac tccagaagcg tctcgatatg attttcttag ggcaattccg tctgcaaccg   2280
acgattaata ccctcaagga ttcaggcatt gacgcacaca agcaggagtc tggcatcgct   2340
cctaactttg ttcactcaca ggacggtagc cacctccgca tgacagtcgt ttatgctcac   2400
gagaagtatg gcattgagtc ctttgcgctc atccatgaca gctttgggac tatcccggca   2460
gacgctggta agctctttaa ggctgtgcgt gaaacgatgg ttatcaccta tgagaacaac   2520
gatgtgctgg cagacttcta ctctcagttt gccgaccagc tacacgagac ccaactggac   2580
```

aagatgcctc cgcttccgaa gaaaggaaac ctgaacctgc aagacattct caagtctgac 2640
tttgcctttg cataa 2655

<210> SEQ ID NO 182
<211> LENGTH: 884
<212> TYPE: PRT
<213> ORGANISM: Bacteriophage T3

<400> SEQUENCE: 182

```
Met Asn Ile Ile Glu Asn Ile Glu Lys Asn Asp Phe Ser Glu Ile Glu
1               5                   10                  15

Leu Ala Ala Ile Pro Phe Asn Thr Leu Ala Asp His Tyr Gly Ser Ala
            20                  25                  30

Leu Ala Lys Glu Gln Leu Ala Leu Glu His Glu Ser Tyr Glu Leu Gly
        35                  40                  45

Glu Arg Arg Phe Leu Lys Met Leu Glu Arg Gln Ala Lys Ala Gly Glu
    50                  55                  60

Ile Ala Asp Asn Ala Ala Ala Lys Pro Leu Leu Ala Thr Leu Leu Pro
65                  70                  75                  80

Lys Leu Thr Thr Arg Ile Val Glu Trp Leu Glu Glu Tyr Ala Ser Lys
                85                  90                  95

Lys Gly Arg Lys Pro Ser Ala Tyr Ala Pro Leu Gln Leu Leu Lys Pro
            100                 105                 110

Glu Ala Ser Ala Phe Ile Thr Leu Lys Val Ile Leu Ala Ser Leu Thr
        115                 120                 125

Ser Thr Asn Met Thr Thr Ile Gln Ala Ala Ala Gly Met Leu Gly Lys
    130                 135                 140

Ala Ile Glu Asp Glu Ala Arg Phe Gly Arg Ile Arg Asp Leu Glu Ala
145                 150                 155                 160

Lys His Phe Lys Lys His Val Glu Glu Gln Leu Asn Lys Arg His Gly
                165                 170                 175

Gln Val Tyr Lys Lys Ala Phe Met Gln Val Val Glu Ala Asp Met Ile
            180                 185                 190

Gly Arg Gly Leu Leu Gly Gly Glu Ala Trp Ser Ser Trp Asp Lys Glu
        195                 200                 205

Thr Thr Met His Val Gly Ile Arg Leu Ile Glu Met Leu Ile Glu Ser
    210                 215                 220

Thr Gly Leu Val Glu Leu Gln Arg His Asn Ala Gly Asn Ala Gly Ser
225                 230                 235                 240

Asp His Glu Ala Leu Gln Leu Ala Gln Glu Tyr Val Asp Val Leu Ala
                245                 250                 255

Lys Arg Ala Gly Ala Leu Ala Gly Ile Ser Pro Met Phe Gln Pro Cys
            260                 265                 270

Val Val Pro Pro Lys Pro Trp Val Ala Ile Thr Gly Gly Gly Tyr Trp
        275                 280                 285

Ala Asn Gly Arg Arg Pro Leu Ala Leu Val Arg Thr His Ser Lys Lys
    290                 295                 300

Gly Leu Met Arg Tyr Glu Asp Val Tyr Met Pro Glu Val Tyr Lys Ala
305                 310                 315                 320

Val Asn Leu Ala Gln Asn Thr Ala Trp Lys Ile Asn Lys Lys Val Leu
                325                 330                 335

Ala Val Val Asn Glu Ile Val Asn Trp Lys Asn Cys Pro Val Ala Asp
            340                 345                 350
```

-continued

```
Ile Pro Ser Leu Glu Arg Gln Glu Leu Pro Pro Lys Pro Asp Asp Ile
        355                 360                 365

Asp Thr Asn Glu Ala Ala Leu Lys Glu Trp Lys Lys Ala Ala Ala Gly
    370                 375                 380

Ile Tyr Arg Leu Asp Lys Ala Arg Val Ser Arg Arg Ile Ser Leu Glu
385                 390                 395                 400

Phe Met Leu Glu Gln Ala Asn Lys Phe Ala Ser Lys Lys Ala Ile Trp
                405                 410                 415

Phe Pro Tyr Asn Met Asp Trp Arg Gly Arg Val Tyr Ala Val Pro Met
            420                 425                 430

Phe Asn Pro Gln Gly Asn Asp Met Thr Lys Gly Leu Leu Thr Leu Ala
        435                 440                 445

Lys Gly Lys Pro Ile Gly Glu Glu Gly Phe Tyr Trp Leu Lys Ile His
    450                 455                 460

Gly Ala Asn Cys Ala Gly Val Asp Lys Val Pro Phe Pro Glu Arg Ile
465                 470                 475                 480

Ala Phe Ile Glu Lys His Val Asp Asp Ile Leu Ala Cys Ala Lys Asp
                485                 490                 495

Pro Ile Asn Asn Thr Trp Trp Ala Glu Gln Asp Ser Pro Phe Cys Phe
            500                 505                 510

Leu Ala Phe Cys Phe Glu Tyr Ala Gly Val Thr His His Gly Leu Ser
        515                 520                 525

Tyr Asn Cys Ser Leu Pro Leu Ala Phe Asp Gly Ser Cys Ser Gly Ile
    530                 535                 540

Gln His Phe Ser Ala Met Leu Arg Asp Glu Val Gly Gly Arg Ala Val
545                 550                 555                 560

Asn Leu Leu Pro Ser Glu Thr Val Gln Asp Ile Tyr Gly Ile Val Ala
                565                 570                 575

Gln Lys Val Asn Glu Ile Leu Lys Gln Asp Ala Ile Asn Gly Thr Pro
            580                 585                 590

Asn Glu Met Ile Thr Val Thr Asp Lys Asp Thr Gly Glu Ile Ser Glu
        595                 600                 605

Lys Leu Lys Leu Gly Thr Ser Thr Leu Ala Gln Gln Trp Leu Ala Tyr
    610                 615                 620

Gly Val Thr Arg Ser Val Thr Lys Arg Ser Val Met Thr Leu Ala Tyr
625                 630                 635                 640

Gly Ser Lys Glu Phe Gly Phe Arg Gln Gln Val Leu Asp Asp Thr Ile
                645                 650                 655

Gln Pro Ala Ile Asp Ser Gly Lys Gly Leu Met Phe Thr Gln Pro Asn
            660                 665                 670

Gln Ala Ala Gly Tyr Met Ala Lys Leu Ile Trp Asp Ala Val Ser Val
        675                 680                 685

Thr Val Val Ala Ala Val Glu Ala Met Asn Trp Leu Lys Ser Ala Ala
    690                 695                 700

Lys Leu Leu Ala Ala Glu Val Lys Asp Lys Lys Thr Lys Glu Ile Leu
705                 710                 715                 720

Arg His Arg Cys Ala Val His Trp Thr Thr Pro Asp Gly Phe Pro Val
                725                 730                 735

Trp Gln Glu Tyr Arg Lys Pro Leu Gln Lys Arg Leu Asp Met Ile Phe
            740                 745                 750

Leu Gly Gln Phe Arg Leu Gln Pro Thr Ile Asn Thr Leu Lys Asp Ser
        755                 760                 765

Gly Ile Asp Ala His Lys Gln Glu Ser Gly Ile Ala Pro Asn Phe Val
```

```
    770                 775                 780

His Ser Gln Asp Gly Ser His Leu Arg Met Thr Val Val Tyr Ala His
785                 790                 795                 800

Glu Lys Tyr Gly Ile Glu Ser Phe Ala Leu Ile His Asp Ser Phe Gly
                805                 810                 815

Thr Ile Pro Ala Asp Ala Gly Lys Leu Phe Lys Ala Val Arg Glu Thr
            820                 825                 830

Met Val Ile Thr Tyr Glu Asn Asn Asp Val Leu Ala Asp Phe Tyr Ser
        835                 840                 845

Gln Phe Ala Asp Gln Leu His Glu Thr Gln Leu Asp Lys Met Pro Pro
    850                 855                 860

Leu Pro Lys Lys Gly Asn Leu Asn Leu Gln Asp Ile Leu Lys Ser Asp
865                 870                 875                 880

Phe Ala Phe Ala


<210> SEQ ID NO 183
<211> LENGTH: 1083
<212> TYPE: DNA
<213> ORGANISM: Escherichia coli

<400> SEQUENCE: 183

atgaaaccag taacgttata cgatgtcgca gagtatgccg gtgtctctta tcagaccgtt     60

tcccgcgtgg tgaaccaggc cagccacgtt tctgcgaaaa cgcgggaaaa agtggaagcg    120

gcgatggcgg agctgaatta cattcccaac cgcgtggcac aacaactggc gggcaaacag    180

tcgttgctga ttggcgttgc cacctccagt ctggccctgc acgcgccgtc gcaaattgtc    240

gcggcgatta aatctcgcgc cgatcaactg ggtgccagcg tggtggtgtc gatggtagaa    300

cgaagcggcg tcgaagcctg taaagcggcg gtgcacaatc ttctcgcgca acgcgtcagt    360

gggctgatca ttaactatcc gctggatgac caggatgcca ttgctgtgga agctgcctgc    420

actaatgttc cggcgttatt tcttgatgtc tctgaccaga cacccatcaa cagtattatt    480

ttctcccatg aagacggtac gcgactgggc gtggagcatc tggtcgcatt gggtcaccag    540

caaatcgcgc tgttagcggg cccattaagt tctgtctcgg cgcgtctgcg tctggctggc    600

tggcataaat atctcactcg caatcaaatt cagccgatag cggaacggga aggcgactgg    660

agtgccatgt ccggttttca acaaaccatg caaatgctga atgagggcat cgttcccact    720

gcgatgctgg ttgccaacga tcagatggcg ctgggcgcaa tgcgcgccat taccgagtcc    780

gggctgcgcg ttggtgcgga tatctcggta gtgggatacg acgataccga agacagctca    840

tgttatatcc cgccgtcaac caccatcaaa caggattttc gcctgctggg gcaaaccagc    900

gtggaccgct tgctgcaact ctctcagggc caggcggtga agggcaatca gctgttgccc    960

gtctcactgg tgaaaagaaa aaccaccctg gcgcccaata cgcaaaccgc ctctccccgc   1020

gcgttggccg attcattaat gcagctggca cgacaggttt cccgactgga aagcgggcag   1080

tga                                                                 1083


<210> SEQ ID NO 184
<211> LENGTH: 360
<212> TYPE: PRT
<213> ORGANISM: Escherichia coli

<400> SEQUENCE: 184

Met Lys Pro Val Thr Leu Tyr Asp Val Ala Glu Tyr Ala Gly Val Ser
1               5                   10                  15
```

-continued

```
Tyr Gln Thr Val Ser Arg Val Val Asn Gln Ala Ser His Val Ser Ala
            20                  25                  30

Lys Thr Arg Glu Lys Val Glu Ala Ala Met Ala Glu Leu Asn Tyr Ile
        35                  40                  45

Pro Asn Arg Val Ala Gln Gln Leu Ala Gly Lys Gln Ser Leu Leu Ile
    50                  55                  60

Gly Val Ala Thr Ser Ser Leu Ala Leu His Ala Pro Ser Gln Ile Val
65                  70                  75                  80

Ala Ala Ile Lys Ser Arg Ala Asp Gln Leu Gly Ala Ser Val Val Val
                85                  90                  95

Ser Met Val Glu Arg Ser Gly Val Glu Ala Cys Lys Ala Ala Val His
            100                 105                 110

Asn Leu Leu Ala Gln Arg Val Ser Gly Leu Ile Ile Asn Tyr Pro Leu
        115                 120                 125

Asp Asp Gln Asp Ala Ile Ala Val Glu Ala Ala Cys Thr Asn Val Pro
    130                 135                 140

Ala Leu Phe Leu Asp Val Ser Asp Gln Thr Pro Ile Asn Ser Ile Ile
145                 150                 155                 160

Phe Ser His Glu Asp Gly Thr Arg Leu Gly Val Glu His Leu Val Ala
                165                 170                 175

Leu Gly His Gln Gln Ile Ala Leu Leu Ala Gly Pro Leu Ser Ser Val
            180                 185                 190

Ser Ala Arg Leu Arg Leu Ala Gly Trp His Lys Tyr Leu Thr Arg Asn
        195                 200                 205

Gln Ile Gln Pro Ile Ala Glu Arg Glu Gly Asp Trp Ser Ala Met Ser
    210                 215                 220

Gly Phe Gln Gln Thr Met Gln Met Leu Asn Glu Gly Ile Val Pro Thr
225                 230                 235                 240

Ala Met Leu Val Ala Asn Asp Gln Met Ala Leu Gly Ala Met Arg Ala
                245                 250                 255

Ile Thr Glu Ser Gly Leu Arg Val Gly Ala Asp Ile Ser Val Val Gly
            260                 265                 270

Tyr Asp Asp Thr Glu Asp Ser Ser Cys Tyr Ile Pro Pro Ser Thr Thr
        275                 280                 285

Ile Lys Gln Asp Phe Arg Leu Leu Gly Gln Thr Ser Val Asp Arg Leu
    290                 295                 300

Leu Gln Leu Ser Gln Gly Gln Ala Val Lys Gly Asn Gln Leu Leu Pro
305                 310                 315                 320

Val Ser Leu Val Lys Arg Lys Thr Thr Leu Ala Pro Asn Thr Gln Thr
                325                 330                 335

Ala Ser Pro Arg Ala Leu Ala Asp Ser Leu Met Gln Leu Ala Arg Gln
            340                 345                 350

Val Ser Arg Leu Glu Ser Gly Gln
        355                 360
```

<210> SEQ ID NO 185
<211> LENGTH: 388
<212> TYPE: DNA
<213> ORGANISM: Escherichia coli

<400> SEQUENCE: 185

```
atgaaacgga ctcagcgcca ggatcaccgc ctggtgatag acgctggcgc gagtgagttt      60

cccggcggta aacacgccga tcgccccttc cttacgaccg atctcatcaa taccggtata     120

acgcgacatc acgggaccaa gcgcctcacc ttcacgcact ttttccagaa tcaccgcagg     180
```

```
caacggcaaa gtagccgaac gcgcctcgcc gcgctggctg gcgttttcaa tcaccaccca    240

actgaaagtg ctgtcaccat cgatgccagc ttcaatcgcc acccaaaaat cagcctctgg    300

aagtaaacgg cgggcattgg ctacccgatt tcgtgcgcca gcgcgcgttt cctcactgcc    360

aaagggctgt tccggtacac cgctctcg                                       388
```

<210> SEQ ID NO 186
<211> LENGTH: 101
<212> TYPE: PRT
<213> ORGANISM: Escherichia coli

<400> SEQUENCE: 186

```
Met Lys Arg Thr Gln Arg Gln Asp His Arg Leu Val Ile Asp Ala Gly
1               5                   10                  15

Ala Ser Glu Phe Pro Gly Gly Lys His Ala Asp Arg Pro Phe Leu Thr
            20                  25                  30

Thr Asp Leu Ile Asn Thr Gly Ile Thr Arg His His Gly Thr Lys Arg
        35                  40                  45

Leu Thr Phe Thr His Phe Phe Gln Asn His Arg Arg Gln Arg Gln Ser
    50                  55                  60

Ser Arg Thr Arg Leu Ala Ala Leu Ala Gly Val Phe Asn His His Pro
65                  70                  75                  80

Thr Glu Ser Ala Val Thr Ile Asp Ala Ser Phe Asn Arg His Pro Lys
                85                  90                  95

Ile Ser Leu Trp Lys
            100
```

<210> SEQ ID NO 187
<211> LENGTH: 634
<212> TYPE: DNA
<213> ORGANISM: Escherichia coli

<400> SEQUENCE: 187

```
atggcacgac taagcttgga cgacgtaatt tcaatggcgc tcaccctgct ggacagcgaa     60

gggctagagg gcttgactac gcgtaagctg gcgcagtccc taaaaattga gcaaccgact    120

ctgtattggc acgtgcgcaa caagcagact cttatgaaca tgctttcaga ggcaatactg    180

gcgaagcatc acacccgttc agcaccgtta ccgactgaga gttggcagca gtttctccag    240

gaaaatgctc tgagtttccg taaagcatta ctggtccatc gtgatggagc ccgattgcat    300

atagggacct ctcctacgcc cccccagttt gaacaagcag aggcgcaact acgctgtcta    360

tgcgatgcag ggttttcggt cgaggaggct cttttcattc tgcaatctat cagccatttt    420

acgttgggtg cagtattaga ggagcaagca acaaaccaga tagaaaataa tcatgtgata    480

gacgctgcac caccattatt acaagaggca tttaatattc aggcgagaac ctctgctgaa    540

atggccttcc atttcgggct gaaatcatta atatttggat tttctgcaca gttagatgaa    600

aaaaagcata cacccattga ggatggtaat aaat                                634
```

<210> SEQ ID NO 188
<211> LENGTH: 211
<212> TYPE: PRT
<213> ORGANISM: Escherichia coli

<400> SEQUENCE: 188

```
Met Ala Arg Leu Ser Leu Asp Asp Val Ile Ser Met Ala Leu Thr Leu
1               5                   10                  15
```

-continued

```
Leu Asp Ser Glu Gly Leu Glu Gly Leu Thr Thr Arg Lys Leu Ala Gln
            20                  25                  30

Ser Leu Lys Ile Glu Gln Pro Thr Leu Tyr Trp His Val Arg Asn Lys
        35                  40                  45

Gln Thr Leu Met Asn Met Leu Ser Glu Ala Ile Leu Ala Lys His His
    50                  55                  60

Thr Arg Ser Ala Pro Leu Pro Thr Glu Ser Trp Gln Gln Phe Leu Gln
65                  70                  75                  80

Glu Asn Ala Leu Ser Phe Arg Lys Ala Leu Leu Val His Arg Asp Gly
                85                  90                  95

Ala Arg Leu His Ile Gly Thr Ser Pro Thr Pro Pro Gln Phe Glu Gln
            100                 105                 110

Ala Glu Ala Gln Leu Arg Cys Leu Cys Asp Ala Gly Phe Ser Val Glu
        115                 120                 125

Glu Ala Leu Phe Ile Leu Gln Ser Ile Ser His Phe Thr Leu Gly Ala
    130                 135                 140

Val Leu Glu Glu Gln Ala Thr Asn Gln Ile Glu Asn Asn His Val Ile
145                 150                 155                 160

Asp Ala Ala Pro Pro Leu Leu Gln Glu Ala Phe Asn Ile Gln Ala Arg
                165                 170                 175

Thr Ser Ala Glu Met Ala Phe His Phe Gly Leu Lys Ser Leu Ile Phe
            180                 185                 190

Gly Phe Ser Ala Gln Leu Asp Glu Lys Lys His Thr Pro Ile Glu Asp
        195                 200                 205

Gly Asn Lys
    210


<210> SEQ ID NO 189
<211> LENGTH: 606
<212> TYPE: DNA
<213> ORGANISM: Escherichia coli

<400> SEQUENCE: 189

atgaaagcgt taacggccag gcaacaagag gtgtttgatc tcatccgtga tcacatcagc      60

cagacaggta tgccgccgac gcgtgcggaa atcgcgcagc gtttggggtt ccgttcccca     120

aacgcggctg aagaacatct gaaggcgctg gcacgcaaag gcgttattga aattgtttcc     180

ggcgcatcac gcgggattcg tctgttgcag gaagaggaag aagggttgcc gctggtaggt     240

cgtgtggctg ccggtgaacc acttctggcg caacagcata ttgaaggtca ttatcaggtc     300

gatccttcct tattcaagcc gaatgctgat ttcctgctgc gcgtcagcgg gatgtcgatg     360

aaagatatcg gcattatgga tggtgacttg ctggcagtgc ataaaactca ggatgtacgt     420

aacggtcagg tcgttgtcgc acgtattgat gacgaagtta ccgttaagcg cctgaaaaaa     480

cagggcaata aagtcgaact gttgccagaa aatagcgagt ttaaaccaat tgtcgttgac     540

cttcgtcagc agagcttcac cattgaaggg ctggcggttg ggttattcg caacggcgac     600

tggctg                                                                606


<210> SEQ ID NO 190
<211> LENGTH: 202
<212> TYPE: PRT
<213> ORGANISM: Escherichia coli

<400> SEQUENCE: 190

Met Lys Ala Leu Thr Ala Arg Gln Gln Glu Val Phe Asp Leu Ile Arg
1               5                   10                  15
```

```
Asp His Ile Ser Gln Thr Gly Met Pro Pro Thr Arg Ala Glu Ile Ala
            20                  25                  30

Gln Arg Leu Gly Phe Arg Ser Pro Asn Ala Ala Glu Glu His Leu Lys
        35                  40                  45

Ala Leu Ala Arg Lys Gly Val Ile Glu Ile Val Ser Gly Ala Ser Arg
    50                  55                  60

Gly Ile Arg Leu Leu Gln Glu Glu Glu Glu Gly Leu Pro Leu Val Gly
65                  70                  75                  80

Arg Val Ala Ala Gly Glu Pro Leu Leu Ala Gln Gln His Ile Glu Gly
                85                  90                  95

His Tyr Gln Val Asp Pro Ser Leu Phe Lys Pro Asn Ala Asp Phe Leu
            100                 105                 110

Leu Arg Val Ser Gly Met Ser Met Lys Asp Ile Gly Ile Met Asp Gly
        115                 120                 125

Asp Leu Leu Ala Val His Lys Thr Gln Asp Val Arg Asn Gly Gln Val
    130                 135                 140

Val Val Ala Arg Ile Asp Asp Glu Val Thr Val Lys Arg Leu Lys Lys
145                 150                 155                 160

Gln Gly Asn Lys Val Glu Leu Leu Pro Glu Asn Ser Glu Phe Lys Pro
                165                 170                 175

Ile Val Val Asp Leu Arg Gln Gln Ser Phe Thr Ile Glu Gly Leu Ala
            180                 185                 190

Val Gly Val Ile Arg Asn Gly Asp Trp Leu
        195                 200
```

<210> SEQ ID NO 191
<211> LENGTH: 20
<212> TYPE: DNA
<213> ORGANISM: Bacteriophage T7

<400> SEQUENCE: 191
taatacgact cactataggg 20

<210> SEQ ID NO 192
<211> LENGTH: 83
<212> TYPE: DNA
<213> ORGANISM: Bacteriophage T3

<400> SEQUENCE: 192
agttgtctat aatatccaac gttgtctatt taccctcact aaagggaata aggtggatac 60
ttaaagaggg aataaagatt tat 83

<210> SEQ ID NO 193
<211> LENGTH: 63
<212> TYPE: DNA
<213> ORGANISM: Bacteriophage SP6

<400> SEQUENCE: 193
aagaatttca aggacttggt aattagggga cactatagaa ggaggccgag gaataacagg 60
aag 63

<210> SEQ ID NO 194
<211> LENGTH: 2214
<212> TYPE: DNA
<213> ORGANISM: Human immunodeficiency virus

<400> SEQUENCE: 194

-continued

```
atgaaagtga aggggatcag gaagaattat cagcacttgt ggaaatgggg catcatgctc     60
cttgggatgt tgatgatctg tagtgctgta gaaaatttgt gggtcacagt ttattatggg    120
gtacctgtgt ggaaagaagc aaccaccact ctattttgtg catcagatgc taaagcatat    180
gatacagagg tacataatgt ttgggccaca catgcctgtg tacccacaga ccccaaccca    240
caagaagtag tattggaaaa tgtgacagaa aattttaaca tgtggaaaaa taacatggta    300
gaacagatgc atgaggatat aatcagttta tgggatcaaa gcctaaagcc atgtgtaaaa    360
ttaaccccac tctgtgttac tttaaattgc actgatttga ggaatgttac taatatcaat    420
aatagtagtg agggaatgag aggagaaata aaaaactgct ctttcaatat caccacaagc    480
ataagagata aggtgaagaa agactatgca cttttctata gacttgatgt agtaccaata    540
gataatgata atactagcta taggttgata aattgtaata cctcaaccat tacacaggcc    600
tgtccaaagg tatcctttga gccaattccc atacattatt gtaccccggc tggttttgcg    660
attctaaagt gtaaagacaa gaagttcaat ggaacagggc catgtaaaaa tgtcagcaca    720
gtacaatgta cacatggaat taggccagta gtgtcaactc aactgctgtt aaatggcagt    780
ctagcagaag aagaggtagt aattagatct agtaatttca cagacaatgc aaaaaacata    840
atagtacagt tgaaagaatc tgtagaaatt aattgtacaa gacccaacaa caatacaagg    900
aaaagtatac atataggacc aggaagagca ttttatacaa caggagaaat aataggagat    960
ataagacaag cacattgcaa cattagtaga acaaaatgga ataacacttt aaatcaaata   1020
gctacaaaat taaaagaaca atttgggaat aataaaacaa tagtctttaa tcaatcctca   1080
ggaggggacc cagaaattgt aatgcacagt tttaattgtg gaggggaatt cttctactgt   1140
aattcaacac aactgtttaa tagtacttgg aattttaatg gtacttggaa tttaacacaa   1200
tcgaatggta ctgaaggaaa tgacactatc acactcccat gtagaataaa acaaattata   1260
aatatgtggc aggaagtagg aaaagcaatg tatgcccctc ccatcagagg acaaattaga   1320
tgctcatcaa atattacagg gctaatatta acaagagatg gtggaactaa cagtagtggg   1380
tccgagatct tcagacctgg gggaggagat atgagggaca attggagaag tgaattatat   1440
aaatataaag tagtaaaaat tgaaccatta ggagtagcac ccaccaaggc aaaaagaaga   1500
gtggtgcaga gagaaaaaag agcagtggga acgataggag ctatgttcct tgggttcttg   1560
ggagcagcag gaagcactat gggcgcagcg tcaataacgc tgacggtaca ggccagacta   1620
ttattgtctg gtatagtgca acagcagaac aatttgctga gggctattga ggcgcaacag   1680
catctgttgc aactcacagt ctggggcatc aagcagctcc aggcaagagt cctggctgtg   1740
gaaagatacc taagggatca acagctccta gggatttggg gttgctctgg aaaactcatc   1800
tgcaccactg ctgtgccttg gaatgctagt tggagtaata aaactctgga tatgatttgg   1860
gataacatga cctggatgga gtgggaaaga gaaatcgaaa attacacagg cttaatatac   1920
accttaattg aggaatcgca gaaccaacaa gaaaagaatg aacaagactt attagcatta   1980
gataagtggg caagtttgtg gaattggttt gacatatcaa attggctgtg gtatgtaaaa   2040
atcttcataa tgatagtagg aggcttgata ggtttaagaa tagtttttac tgtactttct   2100
atagtaaata gagttaggca gggatactca ccattgtcat ttcagaccca cctcccagcc   2160
ccgaggggac ccgacaggcc cgaaggaatc gaagaagaag gtggagacag agac          2214
```

<210> SEQ ID NO 195
<211> LENGTH: 738
<212> TYPE: PRT
<213> ORGANISM: Human immunodeficiency virus

<400> SEQUENCE: 195

Met Lys Val Lys Gly Ile Arg Lys Asn Tyr Gln His Leu Trp Lys Trp
1               5                   10                  15

Gly Ile Met Leu Leu Gly Met Leu Met Ile Cys Ser Ala Val Glu Asn
            20                  25                  30

Leu Trp Val Thr Val Tyr Tyr Gly Val Pro Val Trp Lys Glu Ala Thr
        35                  40                  45

Thr Thr Leu Phe Cys Ala Ser Asp Ala Lys Ala Tyr Asp Thr Glu Val
    50                  55                  60

His Asn Val Trp Ala Thr His Ala Cys Val Pro Thr Asp Pro Asn Pro
65                  70                  75                  80

Gln Glu Val Val Leu Glu Asn Val Thr Glu Asn Phe Asn Met Trp Lys
                85                  90                  95

Asn Asn Met Val Glu Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asp Leu Arg Asn Val Thr Asn Ile Asn Asn Ser Ser Glu
    130                 135                 140

Gly Met Arg Gly Glu Ile Lys Asn Cys Ser Phe Asn Ile Thr Thr Ser
145                 150                 155                 160

Ile Arg Asp Lys Val Lys Lys Asp Tyr Ala Leu Phe Tyr Arg Leu Asp
                165                 170                 175

Val Val Pro Ile Asp Asn Asp Asn Thr Ser Tyr Arg Leu Ile Asn Cys
            180                 185                 190

Asn Thr Ser Thr Ile Thr Gln Ala Cys Pro Lys Val Ser Phe Glu Pro
        195                 200                 205

Ile Pro Ile His Tyr Cys Thr Pro Ala Gly Phe Ala Ile Leu Lys Cys
    210                 215                 220

Lys Asp Lys Lys Phe Asn Gly Thr Gly Pro Cys Lys Asn Val Ser Thr
225                 230                 235                 240

Val Gln Cys Thr His Gly Ile Arg Pro Val Val Ser Thr Gln Leu Leu
                245                 250                 255

Leu Asn Gly Ser Leu Ala Glu Glu Glu Val Val Ile Arg Ser Ser Asn
            260                 265                 270

Phe Thr Asp Asn Ala Lys Asn Ile Ile Val Gln Leu Lys Glu Ser Val
        275                 280                 285

Glu Ile Asn Cys Thr Arg Pro Asn Asn Asn Thr Arg Lys Ser Ile His
    290                 295                 300

Ile Gly Pro Gly Arg Ala Phe Tyr Thr Thr Gly Glu Ile Ile Gly Asp
305                 310                 315                 320

Ile Arg Gln Ala His Cys Asn Ile Ser Arg Thr Lys Trp Asn Asn Thr
                325                 330                 335

Leu Asn Gln Ile Ala Thr Lys Leu Lys Glu Gln Phe Gly Asn Asn Lys
            340                 345                 350

Thr Ile Val Phe Asn Gln Ser Ser Gly Gly Asp Pro Glu Ile Val Met
        355                 360                 365

His Ser Phe Asn Cys Gly Gly Glu Phe Phe Tyr Cys Asn Ser Thr Gln
    370                 375                 380

Leu Phe Asn Ser Thr Trp Asn Phe Asn Gly Thr Trp Asn Leu Thr Gln
385                 390                 395                 400

Ser Asn Gly Thr Glu Gly Asn Asp Thr Ile Thr Leu Pro Cys Arg Ile

-continued

```
                405                 410                 415

Lys Gln Ile Ile Asn Met Trp Gln Glu Val Gly Lys Ala Met Tyr Ala
            420                 425                 430

Pro Pro Ile Arg Gly Gln Ile Arg Cys Ser Ser Asn Ile Thr Gly Leu
        435                 440                 445

Ile Leu Thr Arg Asp Gly Gly Thr Asn Ser Ser Gly Ser Glu Ile Phe
    450                 455                 460

Arg Pro Gly Gly Gly Asp Met Arg Asp Asn Trp Arg Ser Glu Leu Tyr
465                 470                 475                 480

Lys Tyr Lys Val Val Lys Ile Glu Pro Leu Gly Val Ala Pro Thr Lys
                485                 490                 495

Ala Lys Arg Arg Val Val Gln Arg Glu Lys Arg Ala Val Gly Thr Ile
            500                 505                 510

Gly Ala Met Phe Leu Gly Phe Leu Gly Ala Ala Gly Ser Thr Met Gly
        515                 520                 525

Ala Ala Ser Ile Thr Leu Thr Val Gln Ala Arg Leu Leu Leu Ser Gly
    530                 535                 540

Ile Val Gln Gln Gln Asn Asn Leu Leu Arg Ala Ile Glu Ala Gln Gln
545                 550                 555                 560

His Leu Leu Gln Leu Thr Val Trp Gly Ile Lys Gln Leu Gln Ala Arg
                565                 570                 575

Val Leu Ala Val Glu Arg Tyr Leu Arg Asp Gln Gln Leu Leu Gly Ile
            580                 585                 590

Trp Gly Cys Ser Gly Lys Leu Ile Cys Thr Thr Ala Val Pro Trp Asn
        595                 600                 605

Ala Ser Trp Ser Asn Lys Thr Leu Asp Met Ile Trp Asp Asn Met Thr
    610                 615                 620

Trp Met Glu Trp Glu Arg Glu Ile Glu Asn Tyr Thr Gly Leu Ile Tyr
625                 630                 635                 640

Thr Leu Ile Glu Glu Ser Gln Asn Gln Gln Glu Lys Asn Glu Gln Asp
                645                 650                 655

Leu Leu Ala Leu Asp Lys Trp Ala Ser Leu Trp Asn Trp Phe Asp Ile
            660                 665                 670

Ser Asn Trp Leu Trp Tyr Val Lys Ile Phe Ile Met Ile Val Gly Gly
        675                 680                 685

Leu Ile Gly Leu Arg Ile Val Phe Thr Val Leu Ser Ile Val Asn Arg
    690                 695                 700

Val Arg Gln Gly Tyr Ser Pro Leu Ser Phe Gln Thr His Leu Pro Ala
705                 710                 715                 720

Pro Arg Gly Pro Asp Arg Pro Glu Gly Ile Glu Glu Glu Gly Gly Asp
                725                 730                 735

Arg Asp
```

<210> SEQ ID NO 196
<211> LENGTH: 2214
<212> TYPE: DNA
<213> ORGANISM: Human immunodeficiency virus

<400> SEQUENCE: 196

```
atgaaagtga aggggatcag gaagaattat cagcacttgt ggaaatgggg catcatgctc      60

cttgggatgt tgatgatctg tagtgctgta gaaaatttgt gggtcacagt ttattatggg     120

gtacctgtgt ggaaagaagc aaccaccact ctattttgtg catcagatgc taaagcatat     180

gatacagagg tacataatgt ttgggccaca catgcctgtg tacccacaga ccccaaccca     240
```

caagaagtag tattggaaaa tgtgacagaa aattttaaca tgtggaaaaa taacatggta 300
gaacagatgc atgaggatat aatcagttta tgggatcaaa gcctaaagcc atgtgtaaaa 360
ttaaccccac tctgtgttac tttaaattgc actgatttga ggaatgttac taatatcaat 420
aatagtagtg agggaatgag aggagaaata aaaaactgct ctttcagtat caccacaagc 480
ataagagata aggtgaagaa agactatgca cttttctata gacttgacgt agtaccaata 540
gataatgata atactagcta taggttgata aattgtaata cctcaaccat tacacaggcc 600
tgtccaaagg tatcctttga gccaattccc atacattatt gtaccccggc tggttttgcg 660
attctaaagt gtaaagacaa gaagttcaat ggaacagggc catgtaaaaa tgtcagcaca 720
gtacaatgta cacatggaat taggccagta gtgtcaactc aactgctgtt aaatggcagt 780
ctagcagaag aagaggtagt aattagatct agtaatttca cagacaatgc aaaaaacata 840
atagtacagt tgaaagaatc tgtagaaatt aattgtacaa gacccaacaa caatacaagg 900
aaaagtatac atataggacc aggaagagca ttttatacaa caggagaaat aataggagat 960
ataagacaag cacattgcaa cattagtaga acaaaatgga ataacacttt aaatcaaata 1020
gctacaaaat taaaagaaca atttgggaat aataaaacaa tagtctttaa tcaatcctca 1080
ggaggggacc cagaaattgt aatgcacagt tttaattgtg gaggggaatt cttctactgt 1140
aattcaacac aactgtttaa tagtacttgg agttttaatg gtacttggaa tttaacacaa 1200
tcgaatggta ctgaaggaaa tgacactatc acactcccat gtagaataaa acaaattata 1260
aatatgtggc aggaagtagg aaaagcaatg tatgcccctc ccatcagagg acaaattaga 1320
tgctcatcaa atattacagg gctaatatta acaagagatg gtggaactaa cagtagtggg 1380
tccgagatct tcagacctgg gggaggagat atgagggaca attggagaag tgaattatat 1440
aaatataaag tagtaaaaat tgaaccatta ggagtagcac ccaccaaggc aaaaagaaga 1500
gtggtgcaga gagaaaaaag agcagtggga acgataggag ctatgttcct tgggttcttg 1560
ggagcagcag gaagcactat gggcgcagcg tcaataacgc tgacggtaca ggccagacta 1620
ttattgtctg gtatagtgca acagcagaac aatttgctga gggctattga ggcgcaacag 1680
catctgttgc aactcacagt ctggggcatc aagcagctcc aggcaagagt cctggctgtg 1740
gaaagatacc taagggatca acagctccta gggatttggg gttgctctgg aaaactcatc 1800
tgcaccactg ctgtgccttg gaatgctagt tggagtaata aaactctgga tatgatttgg 1860
gataacatga cctggatgga gtgggaaaga gaaatcgaaa attacacagg cttaatatac 1920
accttaattg aggaatcgca gaaccaacaa gaaaagaatg aacaagactt attagcatta 1980
gataagtggg caagtttgtg gaattggttt gacatatcaa attggctgtg gtatgtaaaa 2040
atcttcataa tgatagtagg aggcttgata ggtttaagaa tagtttttac tgtactttct 2100
atagtaaata gagttaggca gggatactca ccattgtcat ttcagaccca cctcccagcc 2160
ccgaggggac ccgacaggcc cgaaggaatc gaagaagaag gtggagacag agac 2214

<210> SEQ ID NO 197
<211> LENGTH: 738
<212> TYPE: PRT
<213> ORGANISM: Human immunodeficiency virus

<400> SEQUENCE: 197

Met Lys Val Lys Gly Ile Arg Lys Asn Tyr Gln His Leu Trp Lys Trp
1               5                   10                  15

Gly Ile Met Leu Leu Gly Met Leu Met Ile Cys Ser Ala Val Glu Asn

-continued

```
                20                  25                  30

Leu Trp Val Thr Val Tyr Tyr Gly Val Pro Val Trp Lys Glu Ala Thr
            35                  40                  45

Thr Thr Leu Phe Cys Ala Ser Asp Ala Lys Ala Tyr Asp Thr Glu Val
    50                  55                  60

His Asn Val Trp Ala Thr His Ala Cys Val Pro Thr Asp Pro Asn Pro
65                  70                  75                  80

Gln Glu Val Val Leu Glu Asn Val Thr Glu Asn Phe Asn Met Trp Lys
                85                  90                  95

Asn Asn Met Val Glu Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asp Leu Arg Asn Val Thr Asn Ile Asn Asn Ser Ser Glu
    130                 135                 140

Gly Met Arg Gly Glu Ile Lys Asn Cys Ser Phe Ser Ile Thr Thr Ser
145                 150                 155                 160

Ile Arg Asp Lys Val Lys Lys Asp Tyr Ala Leu Phe Tyr Arg Leu Asp
                165                 170                 175

Val Val Pro Ile Asp Asn Asp Asn Thr Ser Tyr Arg Leu Ile Asn Cys
            180                 185                 190

Asn Thr Ser Thr Ile Thr Gln Ala Cys Pro Lys Val Ser Phe Glu Pro
        195                 200                 205

Ile Pro Ile His Tyr Cys Thr Pro Ala Gly Phe Ala Ile Leu Lys Cys
    210                 215                 220

Lys Asp Lys Lys Phe Asn Gly Thr Gly Pro Cys Lys Asn Val Ser Thr
225                 230                 235                 240

Val Gln Cys Thr His Gly Ile Arg Pro Val Val Ser Thr Gln Leu Leu
                245                 250                 255

Leu Asn Gly Ser Leu Ala Glu Glu Glu Val Val Ile Arg Ser Ser Asn
            260                 265                 270

Phe Thr Asp Asn Ala Lys Asn Ile Ile Val Gln Leu Lys Glu Ser Val
        275                 280                 285

Glu Ile Asn Cys Thr Arg Pro Asn Asn Asn Thr Arg Lys Ser Ile His
    290                 295                 300

Ile Gly Pro Gly Arg Ala Phe Tyr Thr Thr Gly Glu Ile Ile Gly Asp
305                 310                 315                 320

Ile Arg Gln Ala His Cys Asn Ile Ser Arg Thr Lys Trp Asn Asn Thr
                325                 330                 335

Leu Asn Gln Ile Ala Thr Lys Leu Lys Glu Gln Phe Gly Asn Asn Lys
            340                 345                 350

Thr Ile Val Phe Asn Gln Ser Ser Gly Gly Asp Pro Glu Ile Val Met
        355                 360                 365

His Ser Phe Asn Cys Gly Gly Glu Phe Phe Tyr Cys Asn Ser Thr Gln
    370                 375                 380

Leu Phe Asn Ser Thr Trp Ser Phe Asn Gly Thr Trp Asn Leu Thr Gln
385                 390                 395                 400

Ser Asn Gly Thr Glu Gly Asn Asp Thr Ile Thr Leu Pro Cys Arg Ile
                405                 410                 415

Lys Gln Ile Ile Asn Met Trp Gln Glu Val Gly Lys Ala Met Tyr Ala
            420                 425                 430

Pro Pro Ile Arg Gly Gln Ile Arg Cys Ser Ser Asn Ile Thr Gly Leu
        435                 440                 445
```

-continued

Ile Leu Thr Arg Asp Gly Gly Thr Asn Ser Ser Gly Ser Glu Ile Phe
    450                 455                 460

Arg Pro Gly Gly Gly Asp Met Arg Asp Asn Trp Arg Ser Glu Leu Tyr
465                 470                 475                 480

Lys Tyr Lys Val Val Lys Ile Glu Pro Leu Gly Val Ala Pro Thr Lys
                485                 490                 495

Ala Lys Arg Arg Val Val Gln Arg Glu Lys Arg Ala Val Gly Thr Ile
            500                 505                 510

Gly Ala Met Phe Leu Gly Phe Leu Gly Ala Ala Gly Ser Thr Met Gly
        515                 520                 525

Ala Ala Ser Ile Thr Leu Thr Val Gln Ala Arg Leu Leu Leu Ser Gly
    530                 535                 540

Ile Val Gln Gln Gln Asn Asn Leu Leu Arg Ala Ile Glu Ala Gln Gln
545                 550                 555                 560

His Leu Leu Gln Leu Thr Val Trp Gly Ile Lys Gln Leu Gln Ala Arg
                565                 570                 575

Val Leu Ala Val Glu Arg Tyr Leu Arg Asp Gln Gln Leu Leu Gly Ile
            580                 585                 590

Trp Gly Cys Ser Gly Lys Leu Ile Cys Thr Thr Ala Val Pro Trp Asn
        595                 600                 605

Ala Ser Trp Ser Asn Lys Thr Leu Asp Met Ile Trp Asp Asn Met Thr
    610                 615                 620

Trp Met Glu Trp Glu Arg Glu Ile Glu Asn Tyr Thr Gly Leu Ile Tyr
625                 630                 635                 640

Thr Leu Ile Glu Glu Ser Gln Asn Gln Gln Glu Lys Asn Glu Gln Asp
                645                 650                 655

Leu Leu Ala Leu Asp Lys Trp Ala Ser Leu Trp Asn Trp Phe Asp Ile
            660                 665                 670

Ser Asn Trp Leu Trp Tyr Val Lys Ile Phe Ile Met Ile Val Gly Gly
        675                 680                 685

Leu Ile Gly Leu Arg Ile Val Phe Thr Val Leu Ser Ile Val Asn Arg
    690                 695                 700

Val Arg Gln Gly Tyr Ser Pro Leu Ser Phe Gln Thr His Leu Pro Ala
705                 710                 715                 720

Pro Arg Gly Pro Asp Arg Pro Glu Gly Ile Glu Glu Glu Gly Gly Asp
                725                 730                 735

Arg Asp

<210> SEQ ID NO 198
<211> LENGTH: 1695
<212> TYPE: DNA
<213> ORGANISM: Human influenza A virus

<400> SEQUENCE: 198
atgaaggcaa acctactggt cctgttaagt gcacttgcag ctgcagatgc agacacaata 60
tgtataggct accatgcgaa caattcaacc gacactgttg acacagtact cgagaagaat 120
gtgacagtga cacactctgt taacctgctc gaagacagcc acaacggaaa actatgtaga 180
ttaaaaggaa tagccccact acaattgggg aaatgtaaca tcgccggatg gctcttggga 240
aacccagaat gcgacccact gcttccagtg agatcatggt cctacattgt agaaacacca 300
aactctgaga atggaatatg ttatccagga gatttcatcg actatgagga gctgagggag 360
caattgagct cagtgtcatc attcgaaaga ttcgaaatat ttcccaaaga aagctcatgg 420

-continued

```
cccaaccaca acacaaacgg agtaacggca gcatgctccc atgaggggaa aagcagtttt    480

tacagaaatt tgctatggct gacggagaag gagggctcat acccaaagct gaaaaattct    540

tatgtgaaca aaaaagggaa agaagtcctt gtactgtggg gtattcatca cccgcctaac    600

agtaaggaac aacagaatct ctatcagaat gaaaatgctt atgtctctgt agtgacttca    660

aattataaca ggagatttac cccggaaata gcagaaagac ccaaagtaag agatcaagct    720

gggaggatga actattactg gaccttgcta aaacccggag acacaataat atttgaggca    780

aatggaaatc taatagcacc aatgtatgct ttcgcactga gtagaggctt tgggtccggc    840

atcatcacct caaacgcatc aatgcatgag tgtaacacga agtgtcaaac acccctggga    900

gctataaaca gcagtctccc ttaccagaat atacacccag tcacaatagg agagtgccca    960

aaatacgtca ggagtgccaa attgaggatg gttacaggac taaggaacac tccgtccatt   1020

caatccagag gtctatttgg agccattgcc ggttttattg aagggggatg gactggaatg   1080

atagatggat ggtatggtta tcatcatcag aatgaacagg gatcaggcta tgcagcggat   1140

caaaaaagca cacaaaatgc cattaacggg attacaaaca aggtgaacac tgttatcgag   1200

aaaatgaaca ttcaattcac agctgtgggt aaagaattca acaaattaga aaaaaggatg   1260

gaaaatttaa ataaaaaagt tgatgatgga tttctggaca tttggacata taatgcagaa   1320

ttgttagttc tactggaaaa tgaaaggact ctggatttcc atgactcaaa tgtgaagaat   1380

ctgtatgaga aagtaaaaag ccaattaaag aataatgcca aagaaatcgg aaatggatgt   1440

tttgagttct accacaagtg tgacaatgaa tgcatggaaa gtgtaagaaa tgggacttat   1500

gattatccca aatattcaga agagtcaaag ttgaacaggg aaaaggtaga tggagtgaaa   1560

ttggaatcaa tggggatcta tcagattctg gcgatctact caactgtcgc cagttcactg   1620

gtgcttttgg tctccctggg ggcaatcagt ttctggatgt gttctaatgg atctttgcag   1680

tgcagaatat gcatc                                                   1695
```

```
<210> SEQ ID NO 199
<211> LENGTH: 565
<212> TYPE: PRT
<213> ORGANISM: Human influenza A virus

<400> SEQUENCE: 199

Met Lys Ala Asn Leu Leu Val Leu Leu Ser Ala Leu Ala Ala Ala Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Lys Cys Asn Ile Ala Gly Trp Leu Leu Gly
65                  70                  75                  80

Asn Pro Glu Cys Asp Pro Leu Leu Pro Val Arg Ser Trp Ser Tyr Ile
                85                  90                  95

Val Glu Thr Pro Asn Ser Glu Asn Gly Ile Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Asn
    130                 135                 140
```

-continued

```
Thr Asn Gly Val Thr Ala Ala Cys Ser His Glu Gly Lys Ser Ser Phe
145                 150                 155                 160

Tyr Arg Asn Leu Leu Trp Leu Thr Glu Lys Glu Gly Ser Tyr Pro Lys
                165                 170                 175

Leu Lys Asn Ser Tyr Val Asn Lys Lys Gly Lys Glu Val Leu Val Leu
            180                 185                 190

Trp Gly Ile His His Pro Pro Asn Ser Lys Glu Gln Gln Asn Leu Tyr
        195                 200                 205

Gln Asn Glu Asn Ala Tyr Val Ser Val Val Thr Ser Asn Tyr Asn Arg
    210                 215                 220

Arg Phe Thr Pro Glu Ile Ala Glu Arg Pro Lys Val Arg Asp Gln Ala
225                 230                 235                 240

Gly Arg Met Asn Tyr Tyr Trp Thr Leu Leu Lys Pro Gly Asp Thr Ile
                245                 250                 255

Ile Phe Glu Ala Asn Gly Asn Leu Ile Ala Pro Met Tyr Ala Phe Ala
            260                 265                 270

Leu Ser Arg Gly Phe Gly Ser Gly Ile Ile Thr Ser Asn Ala Ser Met
        275                 280                 285

His Glu Cys Asn Thr Lys Cys Gln Thr Pro Leu Gly Ala Ile Asn Ser
    290                 295                 300

Ser Leu Pro Tyr Gln Asn Ile His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Thr Pro Ser Ile Gln Ser Arg Gly Leu Phe Gly Ala Ile Ala Gly Phe
            340                 345                 350

Ile Glu Gly Gly Trp Thr Gly Met Ile Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Thr Val Ile Glu
385                 390                 395                 400

Lys Met Asn Ile Gln Phe Thr Ala Val Gly Lys Glu Phe Asn Lys Leu
                405                 410                 415

Glu Lys Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asp Asn Glu Cys Met Glu Ser Val Arg
                485                 490                 495

Asn Gly Thr Tyr Asp Tyr Pro Lys Tyr Ser Glu Glu Ser Lys Leu Asn
            500                 505                 510

Arg Glu Lys Val Asp Gly Val Lys Leu Glu Ser Met Gly Ile Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
```

-continued

565

<210> SEQ ID NO 200
<211> LENGTH: 5694
<212> TYPE: DNA
<213> ORGANISM: Artificial Sequence
<220> FEATURE:
<223> OTHER INFORMATION: TK Promoter controlling T7 RNA polymerase and I1L promoter controlling expression of Lac repressor; insert from plasmid WX52

<400> SEQUENCE: 200

```
atgtggccat ttgcatcggt acctgcggga gcaaaatgta ggctggtaga aacactacca     60
gaaaatatgg attttagatc cgatcattta acaacatttg aatgttttaa cgaaattatc    120
actctagcta agaaatatat atacatagca tctttttgtt gtaatcctct gagtacgact    180
aggggcgcgc ttatttttga taaactaaaa gaggcatctg aaaaagggat taaaataata    240
gttttgctag atgaacgagg gaaaagaaat ctgggagagc tacaaagtca ctgcccggat    300
ataaatttta taaccgttaa tatagataaa aaaaataatg tgggactact actcggttgt    360
ttttgggtgt cagatgatga aagatgttat gtaggaaacg cgtcatttac tggaggatct    420
atacatacga ttaaaacgtt aggtgtatat tctgattatc ccccgctggc cacagatctt    480
cgtagaagat ttgatacttt taaagccttt aatagcgcaa aaaattcatg gttgaattta    540
tgctctgcgg cttgttgttt gccagttagc actgcgtatc atattaagaa tcctataggt    600
ggagtgttct ttactgattc tccggaacac ctattgggat attctagaga tctagatacc    660
gatgtagtta ttgataaact caagtcggct aagactagta tagatattga acatttggcc    720
atagttccca ctacacgtgt cgacggtaat agctactatt ggcccgacat ttacaactcc    780
attatagaag cagccattaa tagaggagtt aagatcagac ttctagttgg taattgggat    840
aagaacgacg tatattctat ggcaaccgcc agaagtctag acgcgttgtg tgttcaaaat    900
gatctatctg tgaaggtttt cactattcag aataatacaa aattgttgat agtcgacgac    960
gaatatgttc atatcacttc ggcaaatttc gacggaaccc attaccaaaa tcacggattc   1020
gtcagtttta atagtataga taaacagctt gtaagcgagg ctaaaaaaat atttgagaga   1080
gattgggtga gctcacattc aaagagtctt aagatataac tcgagcgaat aaagtgaaca   1140
ataattaatt ctttattgtc atcatgaaca cgattaacat cgctaagaac gacttctctg   1200
acatcgaact ggctgctatc ccgttcaaca ctctggctga ccattacggt gagcgtttag   1260
ctcgcgaaca gttggccctt gagcatgagt cttacgagat gggtgaagca cgcttccgca   1320
agatgtttga gcgtcaactt aaagctggtg aggttgcgga taacgctgcc gccaagcctc   1380
tcatcactac cctactccct aagatgattg cacgcatcaa cgactggttt gaggaagtga   1440
aagctaagcg cggcaagcgc ccgacagcct tccagttcct gcaagaaatc aagccggaag   1500
ccgtagcgta catcaccatt aagaccactc tggcttgcct aaccagtgct gacaatacaa   1560
ccgttcaggc tgtagcaagc gcaatcggtc gggccattga ggacgaggct cgcttcggtc   1620
gtatccgtga ccttgaagct aagcacttca agaaaaacgt tgaggaacaa ctcaacaagc   1680
gcgtagggca cgtctacaag aaagcattta tgcaagttgt cgaggctgac atgctctcta   1740
agggtctact cggtggcgag gcgtggtctt cgtggcataa ggaagactct attcatgtag   1800
gagtacgctg catcgagatg ctcattgagt caaccggaat ggttagctta caccgccaaa   1860
atgctggcgt agtaggtcaa gactctgaga ctatcgaact cgcacctgaa tacgctgagg   1920
ctatcgcaac ccgtgcaggt gcgctggctg gcatctctcc gatgttccaa ccttgcgtag   1980
```

-continued

```
ttcctcctaa gccgtggact ggcattactg gtggtggcta ttgggctaac ggtcgtcgtc   2040
ctctggcgct ggtgcgtact cacagtaaga aagcactgat gcgctacgaa gacgtttaca   2100
tgcctgaggt gtacaaagcg attaacattg cgcaaaacac cgcatggaaa atcaacaaga   2160
aagtcctagc ggtcgccaac gtaatcacca agtggaagca ttgtccggtc gaggacatcc   2220
ctgcgattga gcgtgaagaa ctcccgatga aaccggaaga catcgacatg aatcctgagg   2280
ctctcaccgc gtggaaacgt gctgccgctg ctgtgtaccg caaggacaag gctcgcaagt   2340
ctcgccgtat cagccttgag ttcatgcttg agcaagccaa taagtttgct aaccataagg   2400
ccatctggtt cccttacaac atggactggc gcggtcgtgt ttacgctgtg tcaatgttca   2460
acccgcaagg taacgatatg accaaaggac tgcttacgct ggcgaaaggt aaaccaatcg   2520
gtaaggaagg ttactactgg ctgaaaatcc acggtgcaaa ctgtgcgggt gtcgataagg   2580
ttccgttccc tgagcgcatc aagttcattg aggaaaacca cgagaacatc atggcttgcg   2640
ctaagtctcc actggagaac acttggtggg ctgagcaaga ttctccgttc tgcttccttg   2700
cgttctgctt tgagtacgct ggggtacagc accacggcct gagctataac tgctcccttc   2760
cgctggcgtt tgacgggtct tgctctggca tccagcactt ctccgcgatg ctccgagatg   2820
aggtaggtgg tcgcgcggtt aacttgcttc ctagtgaaac cgttcaggac atctacggga   2880
ttgttgctaa gaaagtcaac gagattctac aagcagacgc aatcaatggg accgataacg   2940
aagtagttac cgtgaccgat gagaacactg gtgaaatctc tgagaaagtc aagctgggca   3000
ctaaggcact ggctggtcaa tggctggctt acggtgttac tcgcagtgtg actaagcgtt   3060
cagtcatgac gctggcttac gggtccaaag agttcggctt ccgtcaacaa gtgctggaag   3120
ataccattca gccagctatt gattccggca agggtctgat gttcactcag ccgaatcagg   3180
ctgctggata catggctaag ctgatttggg aatctgtgag cgtgacggtg gtagctgcgg   3240
ttgaagcaat gaactggctt aagtctgctg ctaagctgct ggctgctgag gtcaaagata   3300
agaagactgg agagattctt cgcaagcgtt gcgctgtgca ttgggtaact cctgatggtt   3360
tccctgtgtg gcaggaatac aagaagccta ttcagacgcg cttgaacctg atgttcctcg   3420
gtcagttccg cttacagcct accattaaca ccaacaaaga tagcgagatt gatgcacaca   3480
aacaggagtc tggtatcgct cctaactttg tacacagcca agacggtagc caccttcgta   3540
agactgtagt gtgggcacac gagaagtacg gaatcgaatc ttttgcactg attcacgact   3600
ccttcggtac cattccggct gacgctgcga acctgttcaa agcagtgcgc gaaactatgg   3660
ttgacacata tgagtcttgt gatgtactgg ctgatttcta cgaccagttc gctgaccagt   3720
tgcacgagtc tcaattggac aaaatgccag cacttccggc taaaggtaac ttgaacctcc   3780
gtgacatctt agagtcggac ttcgcgttcg cgtaagaatt cctgcagttt gtatttgtat   3840
ttaaaagttg tttggtgaac ttaaatgaaa ccagtaacgt tatacgatgt cgcagagtat   3900
gccggtgtct cttatcagac cgtttcccgc gtggtgaacc aggccagcca cgtttctgcg   3960
aaaacgcggg aaaaagtgga agcggcgatg gcggagctga attacattcc caaccgcgtg   4020
gcacaacaac tggcgggcaa acagtcgttg ctgattggcg ttgccacctc cagtctggcc   4080
ctgcacgcgc cgtcgcaaat tgtcgcggcg attaaatctc gcgccgatca actgggtgcc   4140
agcgtggtgg tgtcgatggt agaacgaagc ggcgtcgaag cctgtaaagc ggcggtgcac   4200
aatcttctcg cgcaacgcgt cagtgggctg atcattaact atccgctgga tgaccaggat   4260
gccattgctg tggaagctgc ctgcactaat gttccggcgt tatttcttga tgtctctgac   4320
```

```
cagacaccca tcaacagtat tattttctcc catgaagacg gtacgcgact gggcgtggag   4380

catctggtcg cattgggtca ccagcaaatc gcgctgttag cgggcccatt aagttctgtc   4440

tcggcgcgtc tgcgtctggc tggctggcat aaatatctca ctcgcaatca aattcagccg   4500

atagcggaac gggaaggcga ctggagtgcc atgtccggtt ttcaacaaac catgcaaatg   4560

ctgaatgagg gcatcgttcc cactgcgatg ctggttgcca acgatcagat ggcgctgggc   4620

gcaatgcgcg ccattaccga gtccgggctg cgcgttggtg cggatatctc ggtagtggga   4680

tacgacgata ccgaagacag ctcatgttat atcccgccgt caaccaccat caaacaggat   4740

tttcgcctgc tggggcaaac cagcgtggac cgcttgctgc aactctctca gggccaggcg   4800

gtgaagggca atcagctgtt gcccgtctca ctggtgaaaa gaaaaaccac cctggcgccc   4860

aatacgcaaa ccgcctctcc ccgcgcgttg gccgattcat taatgcagct ggcacgacag   4920

gtttcccgac tggaaagcgg gcagtgaccc gggaagcttc catggaggcc taaataaata   4980

atttttatgg atccggagag ctcgggtatc tagccacagt aaatcgttaa aaatttaaaa   5040

aaagaaaata gagacgtata gaacgccatc atgttaaaca gggtacaaat cttgatgaaa   5100

acagctaaca attatgaaac tattgagata ttgcgtaatt atttaagact gtatattatt   5160

ttggcacgaa atgaagaagg ccgtggtata ctaatatacg atgataacat agatagtatt   5220

atgtcgatga tgaatattac aagattagaa gttataggat tgacgactca ttgcacaaaa   5280

ttaagatcat cgcctccaat tcctatgtct agattgttta tggacgaaat agatcatgag   5340

tcatattatt ctccaaaaac ttcagattat ccgttgatcg atattatacg aaagcgttcc   5400

cacgaacagg gagatatagc actggcttta gaacaatacg gtatcgagaa tacagattcc   5460

atatcagaaa ttaatgaatg gctgtcgtca aaaggtttag catgttatag atttgtaaaa   5520

tttaacgatt ataggaaaca gatgtatcgt aagttctcta ggtgtactat agttgacagt   5580

atgataatag ggcatatagg tcatcattat atttggatta aaaatttaga aacatatacg   5640

cgtcccgaaa ttgatgtgtt accgtttgat attaaataca tatctagaga tgaa         5694
```

<210> SEQ ID NO 201
<211> LENGTH: 5125
<212> TYPE: DNA
<213> ORGANISM: Artificial Sequence
<220> FEATURE:
<223> OTHER INFORMATION: Firefly luciferase gene inserted into vaccinia A56 gene; insert from plasmid pVOTE.1.gfp

<400> SEQUENCE: 201

```
ctagactttg ttctctgttt tgtatttacg tgaacgttta ttatatatat aatatgtaat     60

acagaaaatt gccacggccg acaatataat taatgcggta ataccaaata tttctacaaa    120

gtccttggtt ttataattgc taatagaggt tgtactaccg cctacagtag ttggtggtac    180

tgtatcatta tcattgtacg tatcataaag atccgcatca tcggtggttg atttagtagt    240

gacaattcca gatgatgtac ttactgtagt gtatgagaca gtgtctgtaa ctgtatgatc    300

ttctttatca gtaattggtt ccggagtctc gtctgttgtg gattctccag atgatgcact    360

tactgtatta atgctatcac tagtgtatgt gacggtgtct gtatgatctt ctacattatc    420

agtaattggt tccggagtcg gaattgggcg gccgcagaaa aattagcgac cggagattgg    480

cgggacgaat acgacgccca tatcccacgg ctgttcaatc caggtatctt gcgggatatc    540

ggccgcttta cttgtacagc tcgtccatgc cgagagtgat cccggcggcg gtcacgaact    600

ccagcaggac catgtgatcg cgcttctcgt tggggtcttt gctcagggcg gactgggtgc    660
```

-continued

```
tcaggtagtg gttgtcgggc agcagcacgg ggccgtcgcc gatgggggtg ttctgctggt    720

agtggtcggc gagctgcacg ctgccgtcct cgatgttgtg gcggatcttg aagttcacct    780

tgatgccgtt cttctgcttg tcggccatga tatagacgtt gtggctgttg tagttgtact    840

ccagcttgtg ccccaggatg ttgccgtcct ccttgaagtc gatgcccttc agctcgatgc    900

ggttcaccag ggtgtcgccc tcgaacttca cctcggcgcg ggtcttgtag ttgccgtcgt    960

ccttgaagaa gatggtgcgc tcctggacgt agccttcggg catggcggac ttgaagaagt   1020

cgtgctgctt catgtggtcg gggtagcggc tgaagcactg cacgccgtag gtcagggtgg   1080

tcacgagggt gggccagggc acgggcagct tgccggtggt gcagatgaac ttcagggtca   1140

gcttgccgta ggtggcatcg ccctcgccct cgccggacac gctgaacttg tggccgttta   1200

cgtcgccgtc cagctcgacc aggatgggca ccaccccggt gaacagctcc tcgcccttgc   1260

tcaccattta tagcatagaa aaaaacaaaa tgaaattcgg tggcgaccgg tatccaccag   1320

gtcatcaata acgatgaagc cttcgccatc gccttctgcg cgtttcagca ctttaagctc   1380

gcgctggttg tcgtgatcgt agctggaaat acaaacggta tcgacatgac gaatacccag   1440

ttcacgcgcc agtaacgcac ccggtaccag accgccacgg cttacggcaa taatgccttt   1500

ccattgttca gaaggcatca gtcggcttgc gagtttacgt gcatggatct gcaacatgtc   1560

ccaggtgacg atgtattttt cgctcatact tccttaccgt gcaataaatt agaatatatt   1620

ttctactttt acgagaaatt aattattgta tttattattt atgggtgaaa aacttactat   1680

aaaaagcggg tgggtttgga attagtgatc gtcgatcgac atggatctcg atcccgcgaa   1740

attaatacga ctcactatag ggaattgtga gcgctcacaa ttccctagca attccgcccc   1800

tctccctccc ccccccctaa cgttactggc cgaagccgct tggaataagg ccggtgtgcg   1860

tttgtctata tgttattttc caccatattg ccgtcttttg gcaatgtgag ggcccggaaa   1920

cctggccctg tcttcttgac gagcattcct aggggtcttt cccctctcgc caaaggaatg   1980

caaggtctgt tgaatgtcgt gaaggaagca gttcctctgg aagcttcttg aagacaaaca   2040

acgtctgtag cgaccctttg caggcagcgg aaccccccac ctggcgacag gtgcctctgc   2100

ggccaaaagc cacgtgtata agatacacct gcaaaggcgg cacaacccca gtgccacgtt   2160

gtgagttgga tagttgtgga aagagtcaaa tggctctcct caagcgtatt caacaagggg   2220

ctgaaggatg cccagaaggt accccattgt atgggatctg atctggggcc tcggtgcaca   2280

tgctttacat gtgtttagtc gaggttaaaa aacgtctagg ccccccgaac cacggggacg   2340

tggttttcct ttgaaaaaca cgataatacc atggaagacg ccaaaaacat aaagaaaggc   2400

ccggcgccat tctatccgct ggaagatgga accgctggag agcaactgca taaggctatg   2460

aagagatacg ccctggttcc tggaacaatt gcttttacag atgcacatat cgaggtggac   2520

atcacttacg ctgagtactt cgaaatgtcc gttcggttgg cagaagctat gaaacgatat   2580

gggctgaata caaatcacag aatcgtcgta tgcagtgaaa actctcttca attctttatg   2640

ccggtgttgg gcgcgttatt tatcggagtt gcagttgcgc ccgcgaacga catttataat   2700

gaacgtgaat tgctcaacag tatgggcatt tcgcagccta ccgtggtgtt cgtttccaaa   2760

aaggggttgc aaaaaatttt gaacgtgcaa aaaaagctcc caatcatcca aaaaattatt   2820

atcatggatt ctaaaacgga ttaccaggga tttcagtcga tgtacacgtt cgtcacatct   2880

catctacctc ccggttttaa tgaatacgat tttgtgccag agtccttcga tagggacaag   2940

acaattgcac tgatcatgaa ctcctctgga tctactggtc tgcctaaagg tgtcgctctg   3000

cctcatagaa ctgcctgcgt gagattctcg catgccagag atcctatttt tggcaatcaa   3060
```

-continued

```
atcattccgg atactgcgat tttaagtgtt gttccattcc atcacggttt tggaatgttt   3120

actacactcg gatatttgat atgtggattt cgagtcgtct taatgtatag atttgaagaa   3180

gagctgtttc tgaggagcct tcaggattac aagattcaaa gtgcgctgct ggtgccaacc   3240

ctattctcct tcttcgccaa aagcactctg attgacaaat acgatttatc taatttacac   3300

gaaattgctt ctggtggcgc tcccctctct aaggaagtcg gggaagcggt tgccaagagg   3360

ttccatctgc caggtatcag gcaaggatat gggctcactg agactacatc agctattctg   3420

attacacccg agggggatga taaaccgggc gcggtcggta aagttgttcc atttttttgaa   3480

gcgaaggttg tggatctgga taccgggaaa acgctgggcg ttaatcaaag aggcgaactg   3540

tgtgtgagag gtcctatgat tatgtccggt tatgtaaaca atccggaagc gaccaacgcc   3600

ttgattgaca aggatggatg gctacattct ggagacatag cttactggga cgaagacgaa   3660

cacttcttca tcgttgaccg cctgaagtct ctgattaagt acaaaggcta tcaggtggct   3720

cccgctgaat tggaatccat cttgctccaa caccccaaca tcttcgacgc aggtgtcgca   3780

ggtcttcccg acgatgacgc cggtgaactt cccgccgccg ttgttgtttt ggagcacgga   3840

aagacgatga cggaaaaaga gatcgtggat tacgtcgcca gtcaagtaac aaccgcgaaa   3900

aagttgcgcg gaggagttgt gtttgtggac gaagtaccga aaggtcttac cggaaaactc   3960

gacgcaagaa aaatcagaga gatcctcata aaggccaaga agggcggaaa gatcgccgtg   4020

taaggatcct aattaattta agatcctaat taatttaaga tccggctgct aacaaagccc   4080

gaaaggaagc tgagttggct gctgccaccg ctgagcaata actagcataa ccccttgggg   4140

cctctaaacg ggtcttgagg ggttttttgc tgaaaggagg aactatatcc ggatcgagat   4200

ccagatctct agaagcttgg agcttgggtc ccacctgacc ccatgccgaa ctcagaagtg   4260

aaacgccgta gcgccgatgg tagtgtgggg tctccccatg cgagagtagg gaactgccag   4320

gcatcaaata aaacgaaagg ctcagtcgaa agactgggcc tttcgtttta tctgttgttt   4380

gtcggtgaac gctctcctga gtaggacaaa tccgccggga gcggatttga acgttgcgaa   4440

gcaacggccc ggagggtggc gggcaggacg cccgccataa actgccaggc atcaaattaa   4500

gcagaaggcc atcctgacgg atggcctttt tgcgtttcta caaactcttc ctgtcgtcat   4560

atctacaagc catcccccca cagatctcgg aattaattct cgatcgagcg gccgcagctc   4620

cgatttcgaa taccgacgag caattagaat tatctatata atcaggtttc ttagaactag   4680

tttccggtga atgtgtagat ccagatagta ttatgtctat agtcgattca ctatctgtat   4740

ttacaatcaa ctctgtggag tattcttcat aatctacttt atcagtgtca tttgtagttg   4800

atgtcataaa gaatgcacat acataagtac cggcatctct agcagtcaat gatttaattg   4860

tgatagttgt aactagatca tcgtatggag agtcgtaaga tattttatcc ttggtataat   4920

tatcaaaata caagacgtcg cttttagcag ctaaaagaat aatggaattg ggctccttat   4980

accaagcact cataacaacg tagtcatttg tattatttcg attacatgat agagttgcat   5040

catcacctat ttttttagat gtctgaggaa aaggtgtagc gtatactaat gatattagta   5100

acaaaagtat tggtaatcgt gtcat                                          5125
```

<210> SEQ ID NO 202
<211> LENGTH: 1154
<212> TYPE: DNA
<213> ORGANISM: Artificial Sequence
<220> FEATURE:
<223> OTHER INFORMATION: DsRED gene flanked by sequences from vaccinia
A22 gene and A24 gene <400> SEQUENCE: 202
cgaagcattt cttgattgga tggacacatt cggattgcga gactccgttc cggatagacg 60
caaattagac gatgtagcgg atagtttcaa tttggctatg agatacgtat tagataaatg 120
gaatactaat tatacacctt ataataggtg taaatctaga aattacataa aaaaaatgta 180
ataacgttag taacgccgaa tttcattttg tttttttcta tgctataaat ggcctcctcc 240
gagaacgtca tcaccgagtt catgcgcttc aaggtgcgca tggagggcac cgtgaacggc 300
cacgagttcg agatcgaggg cgagggcgag ggccgcccct acgagggcca caacaccgtg 360
aagctgaagg tgaccaaggg cggcccccctg cccttcgcct gggacatcct gtccccccag 420
ttccagtacg gctccaaggt gtacgtgaag caccccgccg acatccccga ctacaagaag 480
ctgtccttcc ccgagggctt caagtgggag cgcgtgatga acttcgagga cggcggcgtg 540
gcgaccgtga cccaggactc ctccctgcag gacggctgct tcatctacaa ggtgaagttc 600
atcggcgtga acttcccctc cgacggcccc gtgatgcaga agaagaccat gggctgggag 660
gcctccaccg agcgcctgta cccccgcgac ggcgtgctga agggcgagac ccacaaggcc 720
ctgaagctga aggacggcgg ccactacctg gtggagttca agtccatcta catggccaag 780
aagcccgtgc agctgcccgg ctactactac gtggacgcca agctggacat cacctcccac 840
aacgaggact acaccatcgt ggagcagtac gagcgcaccg agggccgcca ccacctgttc 900
ctgtaagata tagaaacgga atcggtagat cgtctaaaag aattgcttct aaaatgaaaa 960
aaaacactga ttcagaaatg gatcaacgac tagggtataa gtttttggtg cctgatccta 1020
aagccggagt tttttataga ccgttacatt tccaatatgt atcgtattct aattttatat 1080
tgcatcgatt gcatgaaatc ttgaccgtca agcggccact cttatcgttt aagaataata 1140
cagaacgaat tatg 1154

<210> SEQ ID NO 203
<211> LENGTH: 5191
<212> TYPE: DNA
<213> ORGANISM: Artificial Sequence
<220> FEATURE:
<223> OTHER INFORMATION: Gene for influenza A/Puerto Rico/8-MC/1934
(H1N1) inserted into vaccinia A56 gene; insert from plasmid WX58

<400> SEQUENCE: 203
ctagactttg ttctctgttt tgtatttacg tgaacgttta ttatatatat aatatgtaat 60
acagaaaatt gccacggccg acaatataat taatgcggta ataccaaata tttctacaaa 120
gtccttggtt ttataattgc taatagaggt tgtactaccg cctacagtag ttggtggtac 180
tgtatcatta tcattgtacg tatcataaag atccgcatca tcggtggttg atttagtagt 240
gacaattcca gatgatgtac ttactgtagt gtatgagaca gtgtctgtaa ctgtatgatc 300
ttctttatca gtaattggtt ccggagtctc gtctgttgtg gattctccag atgatgcact 360
tactgtatta atgctatcac tagtgtatgt gacggtgtct gtatgatctt ctacattatc 420
agtaattggt tccggagtcg gaattgggcg gccgcagaaa aattagcgac cggagattgg 480
cgggacgaat acgacgccca tatcccacgg ctgttcaatc caggtatctt gcgggatatc 540
ggccgcttta cttgtacagc tcgtccatgc cgagagtgat cccggcggcg gtcacgaact 600
ccagcaggac catgtgatcg cgcttctcgt tggggtcttt gctcagggcg gactgggtgc 660
tcaggtagtg gttgtcgggc agcagcacgg ggccgtcgcc gatgggggtg ttctgctggt 720
agtggtcggc gagctgcacg ctgccgtcct cgatgttgtg gcggatcttg aagttcacct 780

-continued

```
tgatgccgtt cttctgcttg tcggccatga tatagacgtt gtggctgttg tagttgtact    840
ccagcttgtg ccccaggatg ttgccgtcct ccttgaagtc gatgcccttc agctcgatgc    900
ggttcaccag ggtgtcgccc tcgaacttca cctcggcgcg ggtcttgtag ttgccgtcgt    960
ccttgaagaa gatggtgcgc tcctggacgt agccttcggg catggcggac ttgaagaagt   1020
cgtgctgctt catgtggtcg gggtagcggc tgaagcactg cacgccgtag gtcagggtgg   1080
tcacgagggt gggccagggc acgggcagct tgccggtggt gcagatgaac ttcagggtca   1140
gcttgccgta ggtggcatcg ccctcgccct cgccggacac gctgaacttg tggccgttta   1200
cgtcgccgtc cagctcgacc aggatgggca ccaccccggt gaacagctcc tcgcccttgc   1260
tcaccattta tagcatagaa aaaaacaaaa tgaaattcgg tggcgaccgg tatccaccag   1320
gtcatcaata acgatgaagc cttcgccatc gccttctgcg cgtttcagca ctttaagctc   1380
gcgctggttg tcgtgatcgt agctggaaat acaaacggta tcgacatgac gaatacccag   1440
ttcacgcgcc agtaacgcac ccggtaccag accgccacgg cttacggcaa taatgccttt   1500
ccattgttca gaaggcatca gtcggcttgc gagtttacgt gcatggatct gcaacatgtc   1560
ccaggtgacg atgtattttt cgctcatact tccttaccgt gcaataaatt agaatatatt   1620
ttctactttt acgagaaatt aattattgta tttattattt atgggtgaaa aacttactat   1680
aaaaagcggg tgggtttgga attagtgatc gtcgatcgac atggatctcg atcccgcgaa   1740
attaatacga ctcactatag ggaattgtga gcgctcacaa ttccctagca attccgcccc   1800
tctccctccc ccccccctaa cgttactggc cgaagccgct tggaataagg ccggtgtgcg   1860
tttgtctata tgttattttc caccatattg ccgtcttttg gcaatgtgag ggcccggaaa   1920
cctggccctg tcttcttgac gagcattcct aggggtcttt cccctctcgc caaaggaatg   1980
caaggtctgt tgaatgtcgt gaaggaagca gttcctctgg aagcttcttg aagacaaaca   2040
acgtctgtag cgaccctttg caggcagcgg aaccccccac ctggcgacag gtgcctctgc   2100
ggccaaaagc cacgtgtata agatacacct gcaaaggcgg cacaacccca gtgccacgtt   2160
gtgagttgga tagttgtgga aagagtcaaa tggctctcct caagcgtatt caacaagggg   2220
ctgaaggatg cccagaaggt accccattgt atgggatctg atctggggcc tcggtgcaca   2280
tgctttacat gtgtttagtc gaggttaaaa aacgtctagg ccccccgaac cacggggacg   2340
tggttttcct ttgaaaaaca cgataatacc atgaaggcaa acctactggt cctgttaagt   2400
gcacttgcag ctgcagatgc agacacaata tgtataggct accatgcgaa caattcaacc   2460
gacactgttg acacagtact cgagaagaat gtgacagtga cacactctgt taacctgctc   2520
gaagacagcc acaacggaaa actatgtaga ttaaaaggaa tagccccact acaattgggg   2580
aaatgtaaca tcgccggatg gctcttggga aacccagaat gcgacccact gcttccagtg   2640
agatcatggt cctacattgt agaaacacca aactctgaga atggaatatg ttatccagga   2700
gatttcatcg actatgagga gctgagggag caattgagct cagtgtcatc attcgaaaga   2760
ttcgaaatat ttcccaaaga aagctcatgg cccaaccaca acacaaacgg agtaacggca   2820
gcatgctccc atgaggggaa aagcagtttt tacagaaatt tgctatggct gacggagaag   2880
gagggctcat acccaaagct gaaaaattct tatgtgaaca aaaaagggaa agaagtcctt   2940
gtactgtggg gtattcatca cccgcctaac agtaaggaac aacagaatct ctatcagaat   3000
gaaaatgctt atgtctctgt agtgacttca aattataaca ggagatttac cccggaaata   3060
gcagaaagac ccaaagtaag agatcaagct gggaggatga actattactg gaccttgcta   3120
```

-continued

```
aaacccggag acacaataat atttgaggca aatggaaatc taatagcacc aatgtatgct   3180
ttcgcactga gtagaggctt tgggtccggc atcatcacct caaacgcatc aatgcatgag   3240
tgtaacacga agtgtcaaac acccctggga gctataaaca gcagtctccc ttaccagaat   3300
atacacccag tcacaatagg agagtgccca aaatacgtca ggagtgccaa attgaggatg   3360
gttacaggac taaggaacac tccgtccatt caatccagag gtctatttgg agccattgcc   3420
ggttttattg aagggggatg gactggaatg atagatggat ggtatggtta tcatcatcag   3480
aatgaacagg gatcaggcta tgcagcggat caaaaaagca cacaaaatgc cattaacggg   3540
attacaaaca aggtgaacac tgttatcgag aaaatgaaca ttcaattcac agctgtgggt   3600
aaagaattca acaaattaga aaaaaggatg gaaaatttaa ataaaaaagt tgatgatgga   3660
tttctggaca tttggacata taatgcagaa ttgttagttc tactggaaaa tgaaaggact   3720
ctggatttcc atgactcaaa tgtgaagaat ctgtatgaga aagtaaaaag ccaattaaag   3780
aataatgcca aagaaatcgg aaatggatgt tttgagttct accacaagtg tgacaatgaa   3840
tgcatggaaa gtgtaagaaa tgggacttat gattatccca aatattcaga agagtcaaag   3900
ttgaacaggg aaaaggtaga tggagtgaaa ttggaatcaa tggggatcta tcagattctg   3960
gcgatctact caactgtcgc cagttcactg gtgcttttgg tctccctggg ggcaatcagt   4020
ttctggatgt gttctaatgg atctttgcag tgcagaatat gcatctgacc cgggaattct   4080
gcagtcgacg gatcctaatt aatttaagat cctaattaat ttaagatccg gctgctaaca   4140
aagcccgaaa ggaagctgag ttggctgctg ccaccgctga gcaataacta gcataacccc   4200
ttggggcctc taaacgggtc ttgaggggtt ttttgctgaa aggaggaact atatccggat   4260
cgagatccag atctctagaa gcttggagct tgggtcccac ctgaccccat gccgaactca   4320
gaagtgaaac gccgtagcgc cgatggtagt gtggggtctc cccatgcgag agtagggaac   4380
tgccaggcat caaataaaac gaaaggctca gtcgaaagac tgggcctttc gttttatctg   4440
ttgtttgtcg gtgaacgctc tcctgagtag gacaaatccg ccgggagcgg atttgaacgt   4500
tgcgaagcaa cggcccggag ggtggcgggc aggacgcccg ccataaactg ccaggcatca   4560
aattaagcag aaggccatcc tgacggatgg cctttttgcg tttctacaaa ctcttcctgt   4620
cgtcatatct acaagccatc cccccacaga tctcggaatt aattctcgat cgagcggccg   4680
cagctccgat ttcgaatacc gacgagcaat tagaattatc tatataatca ggtttcttag   4740
aactagtttc cggtgaatgt gtagatccag atagtattat gtctatagtc gattcactat   4800
ctgtatttac aatcaactct gtggagtatt cttcataatc tactttatca gtgtcatttg   4860
tagttgatgt cataaagaat gcacatacat aagtaccggc atctctagca gtcaatgatt   4920
taattgtgat agttgtaact agatcatcgt atggagagtc gtaagatatt ttatccttgg   4980
tataattatc aaaatacaag acgtcgcttt tagcagctaa aagaataatg gaattgggct   5040
ccttatacca agcactcata acaacgtagt catttgtatt atttcgatta catgatagag   5100
ttgcatcatc acctattttt ttagatgtct gaggaaaagg tgtagcgtat actaatgata   5160
ttagtaacaa aagtattggt aatcgtgtca t                                  5191
```

```
<210> SEQ ID NO 204
<211> LENGTH: 2253
<212> TYPE: DNA
<213> ORGANISM: Artificial Sequence
<220> FEATURE:
<223> OTHER INFORMATION: T7 promoter expression cassette flanked by
      vaccinia A22 and A24 gene sequences; insert from plasmid WX60
```

-continued

<400> SEQUENCE: 204

```
gaagtcaagg ataactccgt tagggtattg gatatatcaa aattagactg gagttctgat     60
tgggaaaggc gcatagctaa agatttgtca caatatgaat acactacagt tcttctagaa    120
cgtcagccta gaaggtcgcc gtatgttaaa tttatctatt ttattaaagg ctttttatat    180
catacatcgg ctgccaaagt tatttgcgtc tcgcctgtca tgtctggtaa ttcatataga    240
gatcgaaaaa agagatcggt cgaagcattt cttgattgga tggacacatt cggattgcga    300
gactccgttc cggatagacg caaattagac gatgtagcgg atagtttcaa tttggctatg    360
agatacgtat tagataaatg gaatactaat tatacacctt ataataggtg taaatctaga    420
aattacataa aaaaaatgta ataacgttag taacgccccg acatggatct cgatcccgcg    480
aaattaatac gactcactat aggggaatt gtgagcgctc acaattccct agcaattccg    540
cccctctccc tcccccccc taacgttact ggccgaagcc gcttggaata aggccggtgt    600
gcgtttgtct atatgttatt ttccaccata ttgccgtctt ttggcaatgt gagggcccgg    660
aaacctggcc ctgtcttctt gacgagcatt cctaggggtc tttcccctct cgccaaagga    720
atgcaaggtc tgttgaatgt cgtgaaggaa gcagttcctc tggaagcttc ttgaagacaa    780
acaacgtctg tagcgaccct ttgcaggcag cggaaccccc cacctggcga caggtgcctc    840
tgcggccaaa agccacgtgt ataagataca cctgcaaagg cggcacaacc ccagtgccac    900
gttgtgagtt ggatagttgt ggaaagagtc aaatggctct cctcaagcgt attcaacaag    960
gggctgaagg atgcccagaa ggtaccccat tgtatgggat ctgatctggg gcctcggtgc   1020
acatgcttta catgtgttta gtcgaggtta aaaaacgtct aggccccccg aaccacgggg   1080
acgtggtttt cctttgaaaa acacgataat accatggctc gagctcccgg gaattctgca   1140
gtcgacggat cctaattaat ttaagatcct aattaattta agatccggct gctaacaaag   1200
cccgaaagga agctgagttg gctgctgcca ccgctgagca ataactagca taaccccttg   1260
gggcctctaa acgggtcttg aggggttttt tgctgaaagg aggaactata tccggatcga   1320
gatccagatc tctagaagct tggagcttgg gtcccacctg accccatgcc gaactcagaa   1380
gtgaaacgcc gtagcgccga tggtagtgtg gggtctcccc atgcgagagt agggaactgc   1440
caggcatcaa ataaaacgaa aggctcagtc gaaagactgg gcctttcgtt ttatctgttg   1500
tttgtcggtg aacgctctcc tgagtaggac aaatccgccg ggagcggatt tgaacgttgc   1560
gaagcaacgg cccggagggt ggcgggcagg acgcccgcca taaactgcca ggcatcaaat   1620
taagcagaag gccatcctga cggatggcct ttttgcgttt ctacaaactc ttcctgtcgt   1680
catatctaca agccatcccc ccacagatct cggaattaat tctcgacgag cggccgggga   1740
tatagaaacg gaatcggtag atcgtctaaa agaattgctt ctaaaatgaa aaaaaacact   1800
gattcagaaa tggatcaacg actagggtat aagtttttgg tgcctgatcc taaagccgga   1860
gtttttttata gaccgttaca tttccaatat gtatcgtatt ctaattttat attgcatcga   1920
ttgcatgaaa tcttgaccgt caagcggcca ctcttatcgt ttaagaataa tacagaacga   1980
attatgatag aaattagcaa tgttaaagtg actcctccag attactcacc tataatcgcg   2040
agtattaaag gtaagagtta tgatgcatta gccacgttca ctgtaaatat ctttaaagag   2100
gtaatgacca aagagggtat atccatcact aaaataagta gttatgaggg aaaagattct   2160
catttgataa aaattccgct actaatagga tacgggaata aaaatccact tgatacagcc   2220
aagtatcttg ttcctaatgt cataggtgga gtc                                 2253
```

```
<210> SEQ ID NO 205
<211> LENGTH: 4465
<212> TYPE: DNA
<213> ORGANISM: Artificial Sequence
<220> FEATURE:
<223> OTHER INFORMATION: HIV clade ADA envelope T gene controlled by T7
      promoter and flanked by vaccinia A22 and A24 gene sequences;
      insert from plasmid WX61

<400> SEQUENCE: 205

gaagtcaagg ataactccgt tagggtattg gatatatcaa aattagactg gagttctgat     60

tgggaaaggc gcatagctaa agatttgtca caatatgaat acactacagt tcttctagaa    120

cgtcagccta gaaggtcgcc gtatgttaaa tttatctatt ttattaaagg ctttttatat    180

catacatcgg ctgccaaagt tatttgcgtc tcgcctgtca tgtctggtaa ttcatataga    240

gatcgaaaaa agagatcggt cgaagcattt cttgattgga tggacacatt cggattgcga    300

gactccgttc cggatagacg caaattagac gatgtagcgg atagtttcaa tttggctatg    360

agatacgtat tagataaatg gaatactaat tatacacctt ataataggtg taaatctaga    420

aattacataa aaaaaatgta ataacgttag taacgccccg acatggatct cgatcccgcg    480

aaattaatac gactcactat aggggaatt gtgagcgctc acaattccct agcaattccg    540

cccctctccc tccccccccc taacgttact ggccgaagcc gcttggaata aggccggtgt    600

gcgtttgtct atatgttatt ttccaccata ttgccgtctt ttggcaatgt gagggcccgg    660

aaacctggcc ctgtcttctt gacgagcatt cctaggggtc tttcccctct cgccaaagga    720

atgcaaggtc tgttgaatgt cgtgaaggaa gcagttcctc tggaagcttc ttgaagacaa    780

acaacgtctg tagcgaccct ttgcaggcag cggaaccccc cacctggcga caggtgcctc    840

tgcggccaaa agccacgtgt ataagataca cctgcaaagg cggcacaacc ccagtgccac    900

gttgtgagtt ggatagttgt ggaaagagtc aaatggctct cctcaagcgt attcaacaag    960

gggctgaagg atgcccagaa ggtaccccat tgtatgggat ctgatctggg gcctcggtgc   1020

acatgcttta catgtgttta gtcgaggtta aaaaaacgtc taggcccccc gaaccacggg   1080

gacgtggttt tcctttgaaa aacacgataa taccatgaaa gtgaagggga tcaggaagaa   1140

ttatcagcac ttgtggaaat ggggcatcat gctccttggg atgttgatga tctgtagtgc   1200

tgtagaaaat ttgtgggtca cagtttatta tggggtacct gtgtggaaag aagcaaccac   1260

cactctattt tgtgcatcag atgctaaagc atatgataca gaggtacata atgtttgggc   1320

cacacatgcc tgtgtaccca cagaccccaa cccacaagaa gtagtattgg aaaatgtgac   1380

agaaaatttt aacatgtgga aaaataacat ggtagaacag atgcatgagg atataatcag   1440

tttatgggat caaagcctaa agccatgtgt aaaattaacc ccactctgtg ttactttaaa   1500

ttgcactgat ttgaggaatg ttactaatat caataatagt agtgagggaa tgagaggaga   1560

aataaaaaac tgctctttca gtatcaccac aagcataaga gataaggtga agaaagacta   1620

tgcacttttc tatagacttg acgtagtacc aatagataat gataatacta gctataggtt   1680

gataaattgt aatacctcaa ccattacaca ggcctgtcca aaggtatcct ttgagccaat   1740

tcccatacat tattgtaccc cggctggttt tgcgattcta aagtgtaaag acaagaagtt   1800

caatggaaca gggccatgta aaaatgtcag cacagtacaa tgtacacatg gaattaggcc   1860

agtagtgtca actcaactgc tgttaaatgg cagtctagca gaagaagagg tagtaattag   1920

atctagtaat ttcacagaca atgcaaaaaa cataatagta cagttgaaag aatctgtaga   1980

aattaattgt acaagaccca acaacaatac aaggaaaagt atacatatag gaccaggaag   2040
```

-continued

```
agcattttat acaacaggag aaataatagg agatataaga caagcacatt gcaacattag   2100
tagaacaaaa tggaataaca ctttaaatca aatagctaca aaattaaaag aacaatttgg   2160
gaataataaa acaatagtct ttaatcaatc ctcaggaggg gacccagaaa ttgtaatgca   2220
cagttttaat tgtggagggg aattcttcta ctgtaattca acacaactgt ttaatagtac   2280
ttggagtttt aatggtactt ggaatttaac acaatcgaat ggtactgaag gaaatgacac   2340
tatcacactc ccatgtagaa taaaacaaat tataaatatg tggcaggaag taggaaaagc   2400
aatgtatgcc cctcccatca gaggacaaat tagatgctca tcaaatatta cagggctaat   2460
attaacaaga gatggtggaa ctaacagtag tgggtccgag atcttcagac ctgggggagg   2520
agatatgagg gacaattgga gaagtgaatt atataaatat aaagtagtaa aaattgaacc   2580
attaggagta gcacccacca aggcaaaaag aagagtggtg cagagagaaa aaagagcagt   2640
gggaacgata ggagctatgt tccttgggtt cttgggagca gcaggaagca ctatgggcgc   2700
agcgtcaata acgctgacgg tacaggccag actattattg tctggtatag tgcaacagca   2760
gaacaatttg ctgagggcta ttgaggcgca acagcatctg ttgcaactca cagtctgggg   2820
catcaagcag ctccaggcaa gagtcctggc tgtggaaaga tacctaaggg atcaacagct   2880
cctagggatt tggggttgct ctggaaaact catctgcacc actgctgtgc cttggaatgc   2940
tagttggagt aataaaactc tggatatgat ttgggataac atgacctgga tggagtggga   3000
aagagaaatc gaaaattaca caggcttaat atacacctta attgaggaat cgcagaacca   3060
acaagaaaag aatgaacaag acttattagc attagataag tgggcaagtt tgtggaattg   3120
gtttgacata tcaaattggc tgtggtatgt aaaaatcttc ataatgatag taggaggctt   3180
gataggttta agaatagttt ttactgtact ttctatagta aatagagtta ggcagggata   3240
ctcaccattg tcatttcaga cccacctccc agccccgagg ggacccgaca ggcccgaagg   3300
aatcgaagaa gaaggtggag acagagacta atttttatcc cgggaattct gcagtcgacg   3360
gatcctaatt aatttaagat cctaattaat ttaagatccg gctgctaaca aagcccgaaa   3420
ggaagctgag ttggctgctg ccaccgctga gcaataacta gcataacccc ttggggcctc   3480
taaacgggtc ttgaggggtt ttttgctgaa aggaggaact atatccggat cgagatccag   3540
atctctagaa gcttggagct tgggtcccac ctgaccccat gccgaactca gaagtgaaac   3600
gccgtagcgc cgatggtagt gtggggtctc cccatgcgag agtagggaac tgccaggcat   3660
caaataaaac gaaaggctca gtcgaaagac tgggcctttc gttttatctg ttgtttgtcg   3720
gtgaacgctc tcctgagtag gacaaatccg ccgggagcgg atttgaacgt tgcgaagcaa   3780
cggcccggag ggtggcgggc aggacgcccg ccataaactg ccaggcatca aattaagcag   3840
aaggccatcc tgacggatgg cctttttgcg tttctacaaa ctcttcctgt cgtcatatta   3900
caagccatcc ccccacagat ctcggaatta attctcgacg agcggccggg gatatagaaa   3960
cggaatcggt agatcgtcta aaagaattgc ttctaaaatg aaaaaaaaca ctgattcaga   4020
aatggatcaa cgactagggt ataagttttt ggtgcctgat cctaaagccg gagtttttta   4080
tagaccgtta catttccaat atgtatcgta ttctaatttt atattgcatc gattgcatga   4140
aatcttgacc gtcaagcggc cactcttatc gtttaagaat aatacagaac gaattatgat   4200
agaaattagc aatgttaaag tgactcctcc agattactca cctataatcg cgagtattaa   4260
aggtaagagt tatgatgcat tagccacgtt cactgtaaat atctttaaag aggtaatgac   4320
```

-continued

```
caaagagggt atatccatca ctaaaataag tagttatgag ggaaaagatt ctcatttgat   4380

aaaaattccg ctactaatag gatacgggaa taaaaatcca cttgatacag ccaagtatct   4440

tgttcctaat gtcataggtg gagtc                                         4465
```

VIRUS-BASED EXPRESSION VECTORS AND USES THEREOF

CROSS REFERENCE TO RELATED APPLICATIONS

This application is a national stage application under 35 U.S.C. 371 and claims the benefit of PCT Application No. PCT/US2015/052295 having an international filing date of 25 Sep. 2015, which designated the United States, which PCT application claimed the benefit of U.S. Provisional Application No. 62/055,989 filed 26 Sep. 2014. Each of these disclosures are incorporated herein by reference.

REFERENCE TO SEQUENCE LISTING

This application contains a Sequence Listing submitted as an electronic text file named "6137NIAID-37-PCT_Sequence_Listing_ST25.txt", having a size in bytes of 129 KB, and created on Sep. 25, 2015. The information contained in this electronic file is hereby incorporated by reference in its entirety pursuant to 37 CFR § 1.52(e)(5).

TECHNICAL FIELD

The disclosure relates to virus-based expression vectors that may be non-replicating in humans and other animals, have high expression of exogenous genes to achieve strong immunogenicity, demonstrate low expression of vector proteins to minimize anti-vector immune responses and competition with expression of recombinant proteins and are capable of stable propagation in a continuous cell line. Such vectors make ideal vaccines for inducing an immune response in vaccinated individuals.

BACKGROUND

The first poxvirus vectors were constructed more than 30 years ago. The original studies emphasized the large capacity for foreign genetic material and the high levels of expression obtained with recombinant vaccinia virus. Subsequently, emphasis was placed on increased safety and increased immunogenicity, which were mainly achieved through gene deletions in vaccinia virus or use of other host-range restricted poxviruses. These systems have been extensively used for vaccine studies and numerous veterinary vaccines have been licensed. In addition, many such vaccines are in human clinical trials. Nevertheless, the present generation of poxvirus vectors has some shortcomings. The ideal poxvirus vector should have the following characteristics: (i) non-replicating in humans and other animals; (ii) high expression of recombinant gene(s) to achieve strong immunogenicity; (iii) low expression of vector proteins to minimize anti-vector immune responses and competition with expression of recombinant proteins; (iv) stable propagation in a continuous cell line. While most vectors achieve some of these goals, no existent vector meets them all.

SUMMARY OF THE DISCLOSURE

One aspect of this disclosure provides a recombinant viral vector. The recombinant virus vector comprises a first nucleic acid sequence encoding a heterologous DNA-dependent RNA polymerase, wherein the first nucleic acid sequence is functionally linked to a pre-replicative promoter; a second nucleic acid sequence encoding a heterologous repressor protein, wherein the second nucleic acid sequence is functionally linked to a post-replicative promoter; a third nucleic acid sequence comprising at least one polynucleotide sequence encoding at least one heterologous polypeptide, and, at least one inactivating mutation in an ORF required for the expression of post-replicative genes.

The first and second nucleic acid sequences in these viral vectors may be stably inserted into the viral vector. The recombinant viral vector may also be capable of replicating the viral genome. At least one mutation may be in a transcription factor required for expression of post-replicative genes.

The third nucleic acid sequence may include the at least one polynucleotide sequence encoding at least one heterologous polypeptide, is functionally linked to a promoter recognized by the heterologous polymerase, and the third nucleic acid sequence comprises a binding site for the heterologous repressor protein such that binding of the heterologous repressor protein to the binding site impedes the heterologous polymerase from transcribing the third nucleic acid sequence. The promoter may be recognized by the heterologous polymerase is a T7 promoter. The binding site for the heterologous repressor protein may be a lac operator (lacO). The heterologous protein may be a therapeutic protein. The heterologous polypeptide may be an immunogenic polypeptide. The immunogenic polypeptide may be from a virus selected from the group consisting of adenoviruses, herpesviruses, papilloma viruses, polyomaviruses, hepadnaviruses, parvoviruses, astroviruses, calciviruses, picornaviruses, coronaviruses, flaviviruses, togaviruses, hepeviruses, retroviruses, orthomyxoviruses, arenaviruses, bunyaviruses, filoviruses, paramyxoviruses, rhabdoviruses, reoviruses, and poxviruses.

The viral vectors of this disclosure may be used to express, for example, proteins encoded by one or more of adenoviruses, herpesviruses, papilloma viruses, polyomaviruses, hepadnaviruses, parvoviruses, astroviruses, calciviruses, picornaviruses, coronaviruses, flaviviruses, togaviruses, hepeviruses, retroviruses, orthomyxoviruses, arenaviruses, bunyaviruses, filoviruses, paramyxoviruses, rhabdoviruses, reoviruses, and poxviruses that infect humans or other animals, as well as therapeutic proteins or anti-cancer proteins.

The recombinant viral vector may be a recombinant vaccinia virus or chordopoxvirus. The pre-replicative promoter may be a vaccinia virus early promoter. The pre-replicative promoter may be selected from the promoters listed in Table 1. The pre-replicative promoter may be the vaccinia virus thymidine kinase promoter (VACVWR094). The pre-replicative promoter may include SEQID NO:40.

The post-replicative promoter may be a vaccinia virus intermediate promoter. The post-replicative promoter may be selected from the promoters listed in Table 2. The post-replicative promoter may be the vaccinia virus I1L (VACWR070) promoter. The post-replicative promoter may include SEQID NO:90.

The at least one inactivating mutation may be present in an ORF encoding vaccinia virus transcription factor. The transcription factor may control post-replicative gene expression. The transcription factor may be selected from the group encoded by the A8R (VACWR127) and A23R (VACWR143) ORFs and homologs of these transcription factors from other poxviruses. The transcription factor may be encoded by vaccinia virus A23R (VACWR143) ORF.

The heterologous polymerase may be selected from the group consisting of bacteriophage-induced DNA-dependent RNA polymerases. The heterologous polymerase may be a single subunit phage DNA-dependent RNA polymerase, a T7 RNA polymerase (GenBank M38308), a SP6 RNA polymerase (Y00105), and/or a T3 RNA polymerase (M17496). The heterologous polymerase may be at least one of the T7 bacteriophage DNA-dependent RNA polymerases.

The heterologous repressor protein may be selected from the group consisting of prokaryotic proteins that bind operators. The heterologous repressor protein may be the LacI protein. The repressor protein may be selected from at least one of *E. coli* Lac repressor (GenBank EG1 0525), *E. coli* trp repressor (J01715), *E. coli* tet repressor (X14035), and *E. coli* lexA repressor (J01643).

Another aspect provides a method for treating a patient for an illness by administering a recombinant viral vector of this disclosure to the patient. A recombinant viral vector of this disclosure may be administered to a subject in order to elicit an immune response in the subject.

Another aspect provides is a method of vaccinating an individual by administering a recombinant viral vector of this disclosure to the individual.

Another aspect of provides a system for producing a therapeutic composition, the system comprising a recombinant viral vector of this disclosure and a recombinant cell expressing the active transcription factor enabling post-replicative gene expression and formation of progeny virus.

Another aspect provides a method of producing a therapeutic composition for administration into an individual in need of such therapy. These methods include mixing a recombinant viral vector of this disclosure in vitro with a recombinant cell expressing the active transcription factor, and isolating viral particles from the mixture of the recombinant viral vector and the recombinant cell.

BRIEF DESCRIPTION OF THE DRAWINGS

FIG. 2A depicts the construction of the new vector in complementing cell line—RK/A8A23. FIG. 2B depicts the new vector in non-complementing cells—RK13 and HeLa cells.

DETAILED DESCRIPTION

Figure 1:
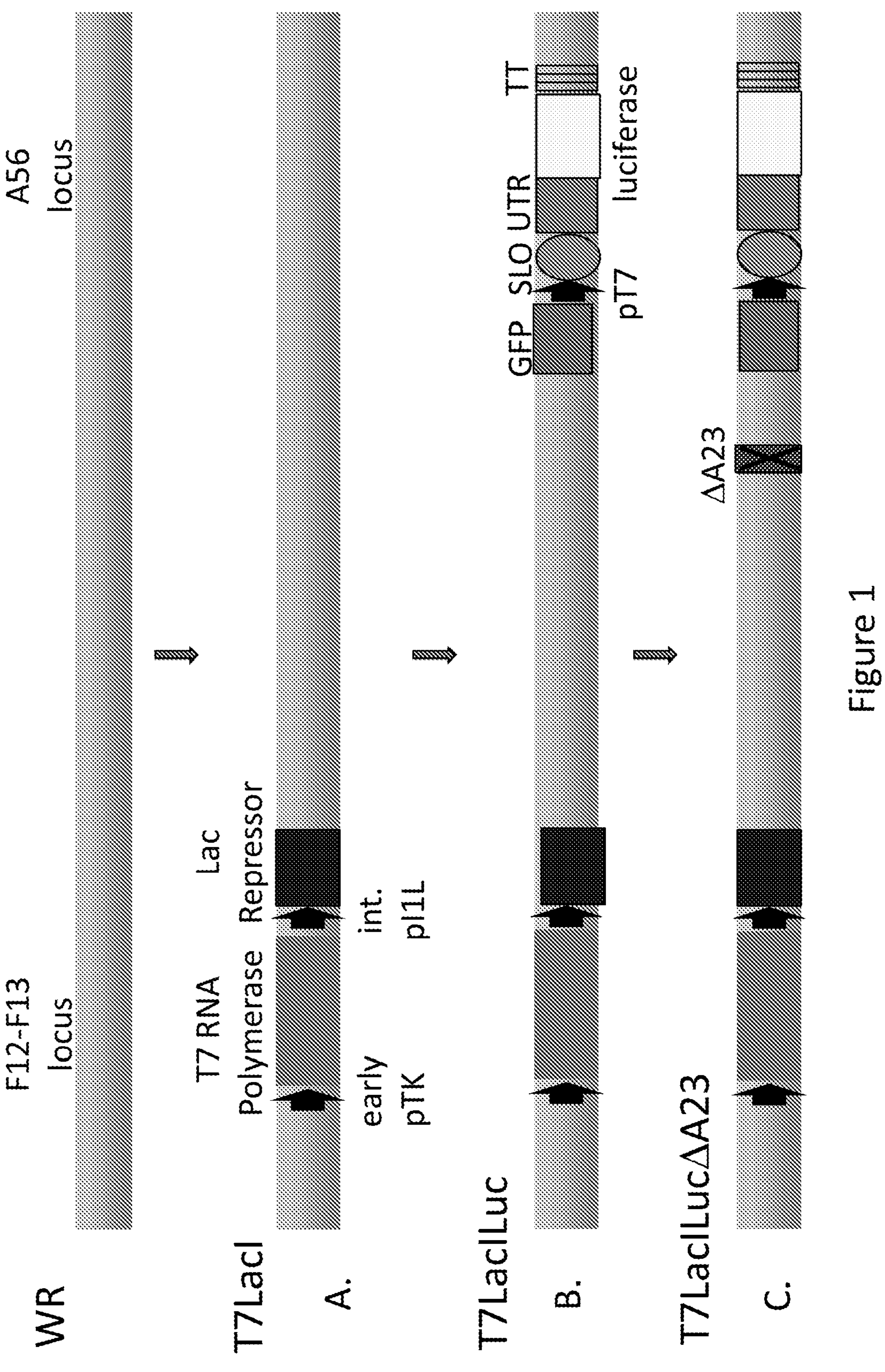
FIGS. 1A, 1B, and 1C show the scheme for constructing new vectors according to this disclosure.

The expression vectors and their uses, described in this disclosure, make use of the fact that many viruses have a life cycle that comprises temporal expression of their genes. Temporal expression of genes refers to the fact that different genes are expressed at different times during the virus life cycle. Some genes are expressed early in the life cycle, some in the middle of the life cycle (intermediate) and others at late times during the viral life cycle (late genes). Such temporal regulation allows for expression of viral proteins only when needed. For example, expression of viral capsid proteins, which are needed to package the viral genome, may be delayed until after genomic replication has occurred and newly synthesized viral genomes are present. Moreover, expression of intermediate and late genes is often dependent on earlier events in the life cycle, such as expression of early genes and virus genome replication, thereby regulating the virus life cycle. Consequently, modification of the expression of such regulatory genes, or the regulatory proteins themselves, can result in inhibition of various parts of the life cycle. The inventors have discovered that by combining elements (e.g., promoters, polymerases, operators, etc.) from various organisms and placing the expression of such elements under the control of a viral temporal expression system, it is possible to create a novel, virus-based expression vector that is particularly useful as a vaccine, or as a delivery platform for other therapeutic molecules such as therapeutic proteins and RNAs. For example, such a vaccine would be particularly useful in vaccinating an individual against organisms such as adenoviruses, herpesviruses, papilloma viruses, polyomaviruses, hepadnaviruses, parvoviruses, astroviruses, calciviruses, picornaviruses, coronaviruses, flaviviruses, togaviruses, hepeviruses, retroviruses, orthomyxoviruses, arenaviruses, bunyaviruses, filoviruses, paramyxoviruses, rhabdoviruses, reoviruses, and poxviruses that infect humans or other animals. Thus, one aspect of this disclosure is a recombinant virus vector that is capable of being grown to high titers under the appropriate conditions in tissue culture, but which is unable to replicate in an individual, wherein the virus vector is capable of high-level expression of a heterologous nucleic acid molecule (e.g., open-reading frame (ORF)) when administered to an individual.

It should be understood that this disclosure is not limited to particular embodiments described, as such may vary. The terminology used herein is for the purpose of describing particular embodiments only, and is not intended to be limiting.

As used herein, and in the appended claims, the singular forms "a," "an," and "the" include plural referents unless the context clearly dictates otherwise. For example, a nucleic acid molecule refers to one or more nucleic acid molecules. As such, the terms "a", "an", "one or more" and "at least one" can be used interchangeably. Similarly the terms "comprising", "including" and "having" can be used interchangeably. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

One embodiment of the disclosure is a recombinant virus vector comprising:

a) a first nucleic acid sequence encoding a heterologous DNA-dependent RNA polymerase, wherein the first nucleic acid sequence is functionally linked to a pre-replicative promoter;

b) a second nucleic acid sequence encoding a heterologous repressor protein, wherein the second nucleic acid sequence is functionally linked to a post-replicative promoter; and, c) at least one inactivating mutation in a virus gene required for the expression of post-replicative viral genes.

This recombinant virus vector is capable of replicating the viral genome when introduced into a cell, and wherein expression of post-replicative viral genes is impeded in cells lacking the activity of the gene required for expression of post-replicative viral genes (i.e. non-complementing cells).

As used herein, a recombinant virus vector, a recombinant viral vector, and the like, is a virus, the genome of which has been altered by the hand of man, wherein the altered virus is still capable of replicating its genome. Such alterations include, but are not limited to, insertion mutations, including insertion of one or more nucleotides, deletion mutations, including deletion of one or more nucleotides, substitution mutations, including substitution of one or more nucleotides, and insertions of heterologous nucleic acid sequences into the genome. Any virus can be used to construct recombinant virus vectors of this disclosure, so long as the resulting recombinant virus vector has the desirable characteristics disclosed herein. Viruses used to construct recombinant virus vectors of this disclosure can be eukaryotic viruses or prokaryotic viruses. Moreover, elements from viruses or bacteria used to construct recombinant virus vectors of this disclosure can be from eukaryotic cells, eukaryotic viruses, prokaryotic viruses, bacteria, or any combination thereof. Examples of such elements include, but are not limited to, ORF sequences, gene sequences, promoter sequences, enhancer sequences, repressor sequences, cleavage sequences, or any useful fragments thereof. Examples of viruses useful for constructing recombinant virus vectors of this disclosure include, but are not limited to, poxviruses, iridoviruses, phycodnaviruses, mimiviruses, adenoviruses, adeno-associated viruses, Simian Virus 40 (SV40), Epstein-Barr virus, herpesvirus, JC virus, bacteriophage T7, bacteriophage, T3 and bacteriophage SP6.

It will be understood by those skilled in the art that because recombinant virus vectors of this disclosure are made by starting with a selected virus (referred to herein as the base or originating virus) and then making alterations to the genome thereof, the majority of the structure (i.e., nucleic acid molecules, proteins, etc.) of the recombinant virus vector will come from the base virus. Indeed, the final recombinant virus vector will comprise the genome of the base virus, albeit with the necessary alterations made thereto. Consequently, the final recombinant virus vector can be referred to with reference to the base virus. For example, if a recombinant virus vector of this disclosure is constructed starting with a vaccinia virus, the majority of the nucleic acid molecules and proteins in the recombinant virus vector will come from vaccinia virus and thus the final recombinant virus vector can be referred to, for example, as a recombinant vaccinia virus vector or a vaccinia-based recombinant virus vector. The recombinant virus vector is selected from the group consisting of a recombinant poxvirus vector, a recombinant vaccinia virus vector, a recombinant chordopoxvirus vector, a recombinant iridovirus vector, a recombinant phycodnavirus vector, a recombinant mimivirus vector, a recombinant adenovirus vector, a recombinant adeno-associated virus vector, a recombinant SV40 virus vector, a recombinant Epstein-Barr virus vector, a recombinant herpes virus vector and a recombinant JC virus vector.

As used herein, the term heterologous is a comparative term, and refers to a molecule that is from an organism different from that to which it is being referenced or that is made synthetically. The molecule can be a protein or a nucleic acid sequence (i.e., RNA or DNA). For example, a heterologous nucleic acid sequence in a recombinant virus vector refers to the fact that the heterologous nucleic acid sequence is from an organism other than the base virus used to construct the recombinant virus vector. As a further example, a heterologous nucleic acid sequence in a recombinant vaccinia virus vector refers to the fact that the heterologous nucleic acid sequence is from an organism other than vaccinia virus or that was made synthetically.

It will be understood by those skilled in the art, that the first and second nucleic acid sequences, being heterologous, are inserted into the genome of the recombinant virus vector. Such heterologous nucleic acid sequence can be inserted at any location in the recombinant virus vector genome, as long as such insertion does not unintentionally alter the functioning of the resulting recombinant virus vector. For example, the first and second nucleic acid sequence can be inserted into a non-essential region. Such non-essential regions include, but are not limited to, naturally occurring deletions within the viral genome (e.g., Del I, II, II, etc. of modified vaccinia virus Ankara (MVA), intergenic regions or non-essential genes. A non-essential region is a genomic region, the alteration of which has no, or almost no, discernible effect on viral replication and the production of progeny virus. One example of a non-essential region is a non-essential gene such as, for example, the vaccinia virus hemagglutinin gene.

Alternatively, the first and second nucleic acid sequences can be inserted into an essential region of the genome (e.g., an essential gene). It will be appreciated that interruption of an essential region will result in a recombinant virus vector unable to complete the virus life cycle and produce progeny virus. However, such recombinant virus vectors can produce progeny virus when grown in cells that provide the missing function. Such a cell can be referred to as a complementing cell because it provides the function usually provided by the essential gene. That is, it "complements" the recombinant virus vector. Conversely, a cell that is unable to provide the missing viral function can be referred to as a non-commenting cell. Such culture systems are disclosed herein. At least one heterologous nucleic acid sequence may be inserted into the gene required for expression of post-replicative viral genes.

According to the present disclosure, any DNA-dependent RNA polymerase can be used to construct recombinant virus vectors of this disclosure, as long as the DNA-dependent RNA polymerase is heterologous relative to the base virus used to construct the recombinant viral vector. Preferred DNA-dependent RNA polymerases to use are bacteriophage-induced DNA-dependent RNA polymerases, as they consist of a single polypeptide. The heterologous DNA-dependent RNA polymerase may be a bacteriophage-induced DNA-dependent RNA polymerase. The heterologous DNA-dependent RNA polymerase may be a single subunit phage DNA-dependent RNA polymerase. The heterologous DNA-dependent RNA polymerase may be from a bacteriophage selected from the group consisting of bacteriophage T3, bacteriophage T4, bacteriophage T7 and bacteriophage SP6. The heterologous DNA-dependent RNA polymerase may be encoded by a nucleic acid molecule comprising a nucleic acid sequence selected from the group consisting of SEQ ID NO:177, SEQ ID NO:179 and SEQ ID NO:181. The heterologous DNA-dependent RNA polymerase may include an amino acid sequence selected from the group consisting of SEQ ID NO:178, SEQ ID NO:180 and SEQ ID NO:182. The heterologous DNA-dependent RNA polymerase may be a bacteriophage T7 DNA-dependent RNA polymerase.

It should be appreciated that while the inventors have disclosed exemplary sequences that can be used to construct recombinant virus vectors of this disclosure, variants of such sequences may also be used, as long as the variant sequence can function for its intended purpose (e.g., transcribe mRNA, repress transcription, etc.). As used herein, a variant refers to a protein, or nucleic acid molecule, the sequence of which is similar, but not identical, to a reference sequence, wherein the activity of the variant protein (or the protein encoded by the variant nucleic acid molecule) is not significantly altered. These variations in sequence can be naturally occurring variations or they can be engineered through the use of genetic engineering technique know to those skilled in the art. Examples of such techniques are found in Sambrook J, Fritsch E F, Maniatis T et al., in Molecular Cloning—A Laboratory Manual, 2nd Edition, Cold Spring Harbor Laboratory Press, 1989, pp. 9.31-9.57), or in Current Protocols in Molecular Biology, John Wiley & Sons, N.Y. (1989), 6.3.1-6.3.6, both of which are incorporated herein by reference in their entirety.

With regard to variants, any type of alteration in the amino acid, or nucleic acid, sequence is permissible so long as the resulting variant sequence functions for its intended purpose. Examples of such variations include, but are not limited to, deletions, insertions, substitutions and combinations thereof. For example, with regard to proteins, it is well understood by those skilled in the art that one or more (e.g., 2, 3, 4, 5, 6, 7, 8, 9 or 10), amino acids can often be removed from the amino and/or carboxy terminal ends of a protein without significantly affecting the activity of that protein. Similarly, one or more (e.g., 2, 3, 4, 5, 6, 7, 8, 9 or 10) amino acids can often be inserted into a protein, or deleted from a protein, without significantly affecting the activity of the protein.

With specific regard to proteins, any amino acid substitution is permissible so long as the activity of the protein is not significantly affected. In this regard, it is appreciated in the art that amino acids can be classified into groups based on their physical properties. Examples of such groups include, but are not limited to, charged amino acids, uncharged amino acids, polar uncharged amino acids, and hydrophobic amino acids. Preferred variants that contain substitutions are those in which an amino acid is substituted with an amino acid from the same group. Such substitutions are referred to as conservative substitutions.

Naturally occurring residues may be divided into classes based on common side chain properties:
1) hydrophobic: Met, Ala, Val, Leu, Ile;
2) neutral hydrophilic: Cys, Ser, Thr;
3) acidic: Asp, Glu;
4) basic: Asn, Gln, His, Lys, Arg;
5) residues that influence chain orientation: Gly, Pro; and
6) aromatic: Trp, Tyr, Phe.

For example, non-conservative substitutions may involve the exchange of a member of one of these classes for a member from another class.

In making amino acid changes, the hydropathic index of amino acids may be considered. Each amino acid has been assigned a hydropathic index on the basis of its hydrophobicity and charge characteristics. The hydropathic indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). The importance of the hydropathic amino acid index in conferring interactive biological function on a protein is generally understood in the art (Kyte et al., 1982, J. Mol. Biol. 157:105-31). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those within ±1 are particularly preferred, and those within ±0.5 are even more particularly preferred.

It is also understood in the art that the substitution of like amino acids can be made effectively on the basis of hydrophilicity, particularly where the biologically functionally equivalent protein or peptide thereby created is intended for use in immunological uses. The greatest local average hydrophilicity of a protein, as governed by the hydrophilicity of its adjacent amino acids, correlates with its immunogenicity and antigenicity, i.e., with a biological property of the protein. The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4). In making changes based upon similar hydrophilicity values, the substitution of amino acids whose hydrophilicity values are within ±2 is preferred, those within ±1 are particularly preferred, and those within ±0.5 are even more particularly preferred. One may also identify epitopes from primary amino acid sequences on the basis of hydrophilicity.

Desired amino acid substitutions (whether conservative or non-conservative) can be determined by those skilled in the art at the time such substitutions are desired. For example, amino acid substitutions can be used to identify important residues of a protein, or to increase or decrease the immunogenicity, solubility or stability of a protein. Exemplary amino acid substitutions are shown in the following table:

TABLE 1

Amino Acid Substitutions

| Original Amino Acid | Exemplary Substitutions |
|---|---|
| Ala | Val, Leu, Ile |
| Arg | Lys, Gln, Asn |
| Asn | Gln |
| Asp | Glu |
| Cys | Ser, Ala |
| Gln | Asn |
| Glu | Asp |
| Gly | Pro, Ala |
| His | Asn, Gln, Lys, Arg |
| Ile | Leu, Val, Met, Ala |
| Leu | Ile, Val, Met, Ala |
| Lys | Arg, Gln, Asn |
| Met | Leu, Phe, Ile |
| Phe | Leu, Val, Ile, Ala, Tyr |
| Pro | Ala |
| Ser | Thr, Ala, Cys |
| Thr | Ser |
| Trp | Tyr, Phe |
| Tyr | Trp, Phe, Thr, Ser |
| Val | Ile, Met, Leu, Phe, Ala |

As used herein, the phrase significantly affect a proteins activity refers to a decrease in the activity of a protein by at least 10%, at least 20%, at least 30% or at least 40%. With regard to the present disclosure, such an activity may be measured, for example, as the ability of a protein to elicit antibodies against the reference (i.e., non-mutated) protein or by measuring the activity of the protein (e.g., polymerase activity, binding activity, etc.). In cases where a protein is necessary for viral replication, such activity may be measured by measuring the ability of the virus to produce progeny virus (e.g., titer). Methods of making such measurements are known to those skilled in the art.

The heterologous DNA-dependent RNA polymerase may be encoded by a nucleic acid molecule comprising a nucleic acid sequence at least 85%, at least 90%, at least 95%, at least 97% or at least 99% identical to a sequence selected from the group consisting of SEQ ID NO:177, SEQ ID NO:179 and SEQ ID NO:181. The heterologous DNA-dependent RNA polymerase may include an amino acid sequence at least 85%, at least 90%, at least 95%, at least 97% or at least 99% identical to a sequence selected from the group consisting of SEQ ID NO:178, SEQ ID NO:180 and SEQ ID NO:182.

As used herein, the term functionally linked refers to two or more nucleic acids sequences, or partial sequences, which are positioned so that they functionally interact to perform their intended functions. For example, a promoter is functionally linked to a nucleic acid (e.g., coding) sequence if it is able to control or modulate transcription of the linked nucleic acid sequence in the cis position. Generally, but not necessarily, functionally linked nucleic acid sequences are close together. Although a functionally linked promoter is generally located upstream of the coding sequence it does not necessarily have to be close to it Enhancers need not be close by either, provided that they assist the transcription of the nucleic acid sequence. For this purpose they may be both upstream and/or downstream of the nucleic acid sequence, possibly at some distance from it. A polyadenylation site is functionally linked to a gene sequence if it is positioned at the 3' end of the gene sequence in such a way that the transcription progresses via the coding sequence to the polyadenylation signal. Accordingly, two or more nucleic acid sequences that are functionally linked may or may not be in direct contact (i.e., immediately adjacent to one another in the virus vector genome).

As used herein, a gene refers to a nucleotide sequence that encodes an amino acid sequence (e.g., protein or peptide). According to this disclosure, a gene may or may not comprise introns. Thus, it should be appreciated that, as used herein, the term gene encompasses open reading frames (ORFs). The term ORF refers to a nucleic acid sequence (or polynucleotide sequence) that encodes an amino acid sequence, but which lacks introns. Thus, the entire sequence of an ORF, with the possible exception of the final termination codon, encodes an amino acid sequence. It should be understood that in the context of this disclosure, the terms gene and ORF can be used interchangeably.

As used herein, pre-replicative refers to elements that function, or events that occur, prior to replication of the recombinant virus vector genome. Likewise, post-replicative refers to elements that function, or events that occur, following replication of the recombinant virus vector genome. For example, a pre-replicative promoter is a promoter that drives expression of a nucleic acid sequence to which it is functionally linked, prior to replication of the recombinant virus vector genome. According to this disclosure, the phrase drive expression, and the like, refers to a scenario in which binding of a promoter by a polymerase causes transcription from a nucleic acid sequence to which the promoter is functionally linked. As a further example, a post-replicative promoter is a promoter that drives expression of a nucleic acid sequence to which it is functionally linked, only after replication of the recombinant virus vector genome has occurred. Likewise, a post-replicative gene is one that is expressed following replication of the recombinant virus vector genome. It is to be understood that a pre-replicative promoter may or may not drive expression of functionally-linked nucleic acid sequences after replication of the recombinant virus vector genome has occurred. The important point is that a pre-replicative promoter functions prior to replication of the recombinant virus vector genome. However, post-replicative promoters used in this disclosure can only function after replication of the recombinant virus vector genome has occurred.

According to this disclosure, any promoter can be used for constructing recombinant virus vectors of this disclosure, as long as it has the appropriate characteristics for the intended purpose. For example, promoters used to control expression of heterologous sequences should respond to transcription factors produced by the recombinant virus vector in a temporal fashion. Thus, for example, any promoter can be used as a pre-replicative promoter as long as it functions (i.e., drives expression of a functionally-linked nucleic acid sequence) prior to replication of the recombinant virus vector genome. Likewise, any promoter can be used as a post-replicative promoter, as long as it only functions once replication of the recombinant virus vector genome has occurred. Promoters can be obtained from any organism (e.g., mammal, eukaryotic virus, prokaryotic virus, bacteria, etc.) as long as they function for their intended purpose. Pre-replicative promoters may be native promoters (i.e., promoters having a sequence identical to that found in an organism) or they may be synthetic. A synthetic promoter is one having sequences that have been altered compared to the sequence found in the organism in nature. A synthetic promoter may also be a promoter that has been designed de novo (not constructed by modifying a natural promoter) and that possesses the desired characteristics (e.g., early, late, etc.). The pre- and post-replicative promoters may be obtained from, or derived from (e.g., a synthetic promoter), the originating virus from which the recombinant virus vector is constructed. For example, if the recombinant virus vector is a recombinant vaccinia virus-based vector, it is preferable to use pre- and post-replicative promoters from vaccinia virus. The pre-replicative promoter may be a poxvirus promoter. The pre-replicative promoter may be a vaccinia virus promoter. The pre-replicative promoter may be selected from the early promoters shown in Table 1.

TABLE 1

Vaccinia Virus Pre-replicative Promoters[1]

| SEQ ID NO | VACWR | VACCOP | Predicted Promoter Core Sequence |
|---|---|---|---|
| 1 | VACWR001/218 | C23L | AAAGTAGAAAATATA |
| 2 | VACWR002/217 | Pseudogene | TATCCGGAGACGTCA |
| 3 | VACWR009/210 | C11R | ATTACTGAATTAATA |
| 4 | VACWR010/209 | C10L | GCAACGTAAAACACA |
| 5 | VACWR011/208 | no ortholog | AAAAAATAAAAAAAA |
| 6 | VACWR012/207 | no ortholog | AGTAAAGAAAAAGAA |
| 7 | VACWR013 | no ortholog | AAAATTGATAAATAA |
| 8 | VACWR018 | no ortholog | AAATTAGACATTTGA |
| 9 | VACWR019 | C9L | ATAACTGAAATGAAA |
| 10 | VACWR021 | C7L | AAAGATGAAAAAGTA |
| 11 | VACWR022 | C6L | ATTAATGAAATAATA |
| 12 | VACWR023 | C5L | AAAAATGAAAATGGA |
| 13 | VACWR024 | C4L | AAAACATAAAAATTA |
| 14 | VACWR029 | N2L | ATAACATAAAAATAA |
| 15 | VACWR031 | M2L | AAGATAGATTTCCTA |

TABLE 1-continued

Vaccinia Virus Pre-replicative Promoters[1]

| SEQ ID NO | VACWR | VACCOP | Predicted Promoter Core Sequence |
|---|---|---|---|
| 16 | VACWR032 | K1L | AAAAATGAAAAAATA |
| 17 | VACWR034 | K3L | GAAAAAGAAATTCCT |
| 18 | VACWR037 | K5L | AATGGTGAAAAAATG |
| 19 | VACWR038 | K6L | AAAACATAAAAATAA |
| 20 | VACWR039 | K7R | ATAATTGTAAAAACA |
| 21 | VACWR046 | F7L | ATAATTGAAAATGGA |
| 22 | VACWR047 | F8L | AAAAATTTAATTACA |
| 23 | VACWR050 | F11L | AAAAGTGAAAAACAA |
| 24 | VACWR051 | F12L | AAAAAAGAAAATAGA |
| 25 | VACWR053 | F14L | GTAGAAGAAAATAAT |
| 26 | VACWR054 | F15L | AAAAATGAAACGTAA |
| 27 | VACWR055 | F16L | AAAAAACAAAATGAA |
| 28 | VACWR057 | E1L | GAGACAGTAGTTTTA |
| 29 | VACWR059 | E3L | AAAAATGATAAAATA |
| 30 | VACWR060 | E4L | AATAATGAAAAAATA |
| 31 | VACWR061 | E5R | ACAAAAGTGAATATA |
| 32 | VACWR065 | E9L | TTAAATGAAAATATA |
| 33 | VACWR068 | OIL | AATAATGAAAAAACA |
| 34 | VACWR072 | I3L | TAAAGTGAAAATATA |
| 35 | VACWR073 | I4L | ATTAATGAAAAGTTA |
| 36 | VACWR080 | G2R | ATAACAAAAATAAAA |
| 37 | VACWR082 | G5R | AAAAATGATAAGATA |
| 38 | VACWR083 | G5.5R | AAAACTGTAACACGA |
| 39 | VACWR089 | L2R | AAAACTGAAAATATA |
| 40 | VACWR094 | J2R | TAAAGTGAACAATAA |
| 41 | VACWR098 | J6R | AAAAGGGAAATTTGA |
| 42 | VACWR101 | H3L | AGAATTGAAAACGAA |
| 43 | VACWR103 | H5R | AAAAATGAAAATAAA |
| 44 | VACWR106 | D1R | GTAAATGAAAAAAAA |
| 45 | VACWR109 | D4R | GAAAATGAAAAGGTA |
| 46 | VACWR112 | D7R | AAAACTGATGAAATA |
| 47 | VACWR114 | D9R | AAAAATGAAATGATA |
| 48 | VACWR117 | D12L | AATAATGAAAACAAA |
| 49 | VACWR123 | A4L | AATTCTGAAACTAGA |
| 50 | VACWR124 | A5R | AAAATTGAATTGCGA |
| 51 | VACWR127 | A8R | TAAAGTGAAAATCTA |
| 52 | VACWR138 | A18R | GCAATAGAAAAGATG |

TABLE 1-continued

Vaccinia Virus Pre-replicative Promoters[1]

| SEQ ID NO | VACWR | VACCOP | Predicted Promoter Core Sequence |
|---|---|---|---|
| 53 | VACWR141 | A20R | AAGAATGAAATAACA |
| 54 | VACWR143 | A23R | AAAAATGTAATAACG |
| 55 | VACWR152 | A29L | AAAGTCGAAAAAGAA |
| 56 | VACWR154 | A31R | AAAACATAAATATAA |
| 57 | VACWR156 | A33R | AATATGGAAAACTAA |
| 58 | VACWR158 | A35R | AAAAATGAATTAATA |
| 59 | VACWR160 | A37R | AAAATTGAAGTAATA |
| 60 | VACWR165 | A40R | AATACTTAAAATGTA |
| 61 | VACWR166 | A41L | AAAATATAAAATAAA |
| 62 | VACWR169 | 268 | AAAAATGAACTCTTA |
| 63 | VACWR170 | A44L | AAAATAGAATAAGTA |
| 64 | VACWR172 | A46R | ATAAATGAAAAGATA |
| 65 | VACWR173 | A47L | AAAACTGAAAATAAA |
| 66 | VACWR174 | A48R | AAATTGTAAAAAATA |
| 67 | VACWR176 | A50R | AAATATTAAAAAAAA |
| 68 | VACWR178 | A52R | GAAATAAAAAACATA |
| 69 | VACWR180 | A55R | AAAAATAAAAATATA |
| 70 | VACWR181 | A56R | AATTTTGTAAAAATA |
| 71 | VACWR181.5 | — | ATTACATATTATATA |
| 72 | VACWR183 | B1R | AAAACTTAAAATTTA |
| 73 | VACWR184 | B2R | ATAAAAATTAAAAAA |
| 74 | VACWR187 | B5R | ATATCTAAAAATCTT |
| 75 | VACWR188 | B6R | AAAAATAATGACCAA |
| 76 | VACWR190 | B8R | ATTATTCAAAATATG |
| 77 | VACWR193 | B11R | GAAAATGAAAATATA |
| 78 | VACWR194 | B12R | AAAACATAAAAAACA |
| 79 | VACWR195 | B13R | AAGATTGAAATTATA |
| 80 | VACWR198 | B17L | AAATATGTAAATATG |
| 81 | VACWR200 | B19R | AAAACTGATATTATA |
| 82 | VACWR201 | Pseudogene | ATAAATGTAGACTCT |
| 83 | VACWR205 | C12L | TAAACTGAAGTTTAA |

[1]VACWR and VACCOP refer to different ORF nomenclatures originally used for the WR and Copenhagen strains of vaccinia virus The pre-replicative promoter may include a nucleic acid sequence selected from the promoter sequences listed in Table 1. The pre-replicative promoter may include a functional variant of a sequence selected from those listed in Table 1. The pre-replicative promoter may include a nucleic acid sequence selected from the group consisting of SEQ ID NO:1-SEQ ID NO:83. The pre-replicative promoter may include a functional variant of a nucleic acid sequence selected from the group consisting of SEQ ID NO:1-SEQ ID NO:83. The variations preferably do not significantly affect the native activity of the variant promoter. The pre-replicative promoter may be the vaccinia virus thymidine kinase promoter (VACVWR094). The pre-replicative promoter may include SEQ ID NO: 40.

The post-replicative promoter may be a poxvirus promoter. The post-replicative promoter may be a vaccinia virus promoter. The post-replicative promoter may be selected from the late or intermediate promoters shown in Table 2.

TABLE 2

Vaccinia Virus ORFs Having Post-Replicative Promoters

| SEQ ID NO | VACWR | VACCOP | Promoter Sequence[1] |
|---|---|---|---|
| 84 | VACWR033 | K2L | ATTTTTATACCGAACATAAAAATAAGGTTAATTATT AATACCATAAAATCATG |
| 85 | VACWR035 | K4L | GGATTTTTAATAGAGTGAAGTGATATAGGATTATTC TTTTAACAAATAAAATG |
| 86 | VACWR052 | F13L | ATTCTAGAATCGTTGATAGAACAGGATGTATAAGTT TTTATGTTAACTAAATG |
| 87 | VACWR067 | E11L | TTTGTATCATTTGTCCATCAACGTCATTTCAATAATA TTGGATGATATAAATG |
| 88 | VACWR069 | O2L | ACTAAAGAGTTAAATAAGTCGAGATAGTTTTATATC ACTTAAATATTAAAATG |
| 89 | VACWR069.5 | O3L | GTGCCTAATATTACTATATCAAGTAATGCTGAATAA AAATATTTATAAATATG |
| 90 | VACWR070 | I1L | TTCTACTACTATTGATATATTTGTATTTAAAAGTTGT TTGGTGAACTTAAATG |

TABLE 2-continued

| Vaccinia Virus ORFs Having Post-Replicative Promoters | | | |
|---|---|---|---|
| SEQ ID NO | VACWR | VACCOP | Promoter Sequence[1] |
| 91 | VACWR074 | I5L | ATACAACTAGGACTTTGTCACATATTCTTTGATCTAA TTTTTAGATATAAATG |
| 92 | VACWR075 | I6L | TGTGATATGTGATAAATTAACTACAAAATTAAATAG AATAGTAAACGACGATG |
| 93 | VACWR081 | G4L | CAGTGATTTATTTTCCAGCAGTAACGATTTTAAGTTT TTGATACCCATAAATG |
| 94 | VACWR099 | H1L | AATTACACGCGTTTACCGATAAAGTAGTTTTATCCA TTTGTACGTTATAAATG |
| 95 | VACWR101 | H3L | AAAATATAACTCGTATTAAAGAGTTGTATATGATTA ATTTCAATAACTAAATG |
| 96 | VACWR113 | D8L | AATTCCCATACTAAGAGCTATTTTTAAACAGTTATC ATTTCATTTTTACTATG |
| 97 | VACWR116 | D11L | TAAACTACTGCTGTGATTTTTAAAACATAGTTATTAC TTATCACTCATAAATG |
| 98 | VACWR118 | D13L | GATATTTCTCTACGGAGTTTATTGTAAGCTTTTTCCA TTTTAAATAGAAAATG |
| 99 | VACWR119 | A1L | AGGTTTTCTACTTGCTCATTAGAAGTATAAAAAAAT AGTTCCGTAATTAAATG |
| 100 | VACWR120 | A2L | AAAATGTTTTTATATAAAATATTGGACGACGAGATA CGTAGAGTGTTAACATG |
| 101 | VACWR122 | A3L | AGATTGGATATTAAAATCACGCTTTCGAGTAAAAAC TACGAATATAAATAATG |
| 102 | VACWR125 | A6L | AACTCTGGAAGAGCACAAATAAATTAAACAACTAA ATCTGTAAATAAATAATG |
| 103 | VACWR131 | A12L | TATAATCTAGTTAAATCTTCTGTATAAATAAAAATA TTTTTAGCTTCTAAATG |
| 104 | VACWR135 | A15L | CTATTTTATATCTATTTATTCGCGTCCTAAAATTAAA ACAAATGATATAAATG |
| 105 | VACWR136 | A16L | GATGTTGATATACCAACATTTAACAGTTTAAATACT GACGATTATTAAGAATG |
| 106 | VACWR139 | A19L | TTGCACGATCGTGTTATAGGGCATATTCTGACTTATT TTTTACTACCTAAATG |
| 107 | VACWR146 | | AATTCGAAAGAAAAAGAATCACAGTCCTAAAAGCT GAACTTCGGAAATCTATG |
| 108 | VACWR147 | | ATCTAGAATATCAGATCTTGAAAGACAGTTGAACGA CTGTAGACGTAATAATG |
| 109 | VACWR148 | A25L | TTATAATTACCCGATTGTAGTTAAGTTTTGAATAAA ATTTTTTATAATAAATG |
| 110 | VACWR150 | A27L | TACCAAATATAAATAACGCAGAGTGTCAGTTTCTAA AATCTGTACTTTAAATG |
| 111 | VACWR153 | A30L | TCCATAAAAGACGAATAAGATACAAACACAAATGT TTATATAATATTTAAATG |
| 112 | VACWR153.5 | A30.5L | ATGTTTTTTCCAAAAACCTAAGTGTATTTAAAATAG ATGCCATGTTAAAAATG |
| 113 | VACWR155 | A32L | TCCATATTTTGATTTATTATCAAATTAATTTAGTAAC TGTAAATATAATTATG |
| 114 | VACWR162 | A38L | CAAAATAGAATAAAATAAATAACAAAGGTATCATTT TAAATAAATAAAAAATG |
| 115 | VACWR204.5 | | GATATCCATGGTATAGACCAAACAATAACGATATAT ATCATAAATAAATAATG |

TABLE 2-continued

| Vaccinia Virus ORFs Having Post-Replicative Promoters | | | |
|---|---|---|---|
| SEQ ID NO | VACWR | VACCOP | Promoter Sequence[1] |
| 116 | VACWR062 | E6R | TAATTATTAGAATAAGAGTGTAGTATCATAGATAAC TCTCTTCTATAAAAATG |
| 117 | VACWR063 | E7R | TATACATAGATATAATTATCACATATTAAAAATTCA CACATTTTTGATAAATG |
| 118 | VACWR064 | E8R | ACATAAAAACTCATTACATAGTTGATAAAAAGCGGT AGGATATAAATATTATG |
| 119 | VACWR077 | I8R | TAGTTCTGGTATTTTACTAATTACTAAATCTGTATAT CTTTCCATTTATCATG |
| 120 | VACWR086 | G8R | CGACGCTGTTCTGCAGCCATTTAACTTTAAATAATTT ACAAAAATTTAAAATG |
| 121 | VACWR091 | L4R | TTTGTAACATCGGTACGGGTATTCATTTATCACAAA AAAAACTTCTCTAAATG |
| 122 | VACWR093 | J1R | TAGTAAACCGATAGTGTATAAAGATTGTGCAAAGCT TTTGCGATCAATAAATG |
| 123 | VACWR105 | H7R | CTACGGATGGATGATATAGATCTTTACACAAATAAT TACAAAACCGATAAATG |
| 124 | VACWR111 | D6R | ATCTCCGTAAATATATGCTCATATATTTATAGAAGA TATCACATATCTAAATG |
| 125 | VACWR115 | D10R | GATAAATACGAATATCTGTCTTATATTTATAATATGC TAGTTAATAGTAAATG |
| 126 | VACWR142 | A22R | CAATATTGAAAATACTAATTGTTTAAATAACCCGAG TATTGAAACTATATATG |
| 127 | VACWR157 | A34R | TATTTTTGTGTTAAAACAATGAACTAATATTTATTTT TGTACATTAATAAATG |
| 128 | VACWR164 | | GATACGATACTATATGTATTCTTCGATAGTCCGCATT ATGTACCTATTCTATG |
| 129 | VACWR167 | A42R | CAAGTTTATTCCAATAGATGTCTTATTAAAAACATA TATAATAAATAACAATG |
| 130 | VACWR168 | A43R | AACTGGTAATTAAAATAAAAAGTAATATTCATATGT AGTGTCAATTTTAAATG |
| 131 | VACWR179 | A53R | TTTTTGATGGTGGTTTAACGTTTTAAAAAAAGATTTT GTTATTGTAGTATATG |
| 132 | VACWR186 | B4R | TAACATTGTTAATTGAAAAGGGATAACATGTTACAG AATATAAATTATATATG |
| 133 | VACWR191 | B9R | TGCATATTATACACTGGTTAACGCCCTTATAGGCTCT AACCATTTTCAAGATG |
| 134 | VACWR192 | | TTGCAGTGTTCATCTCCCAACTGCAAGTGAAGGATT GATAACTGAAGGCAATG |
| 135 | VACWR197 | | CTCTTCTCCCTTTCCCAGAAACAAACTTTTTTTACCC ACTATAAAATAAAATG |
| 136 | VACWR206 | C13L | AATAGTATAAACTAAAAATTAAACAAATCGTTATTA TAAGTAATATCAAAATG |
| 137 | VACWR008 | C19L | TTCTGTTTTTCTTTCACATCTTTAATTATGAAAAAGT AAATCATTATGAGATG |
| 138 | VACWR020 | C8L | CACTTACTAAATAGCCAAGGTGATTATTCGTATTTTT TTAAGGAGTAACCATG |
| 139 | VACWR025 | C3L | TTTTATTATTTGTACGATGTCCAGGATAACATTTTTA CGGATAAATAAATATG |
| 140 | VACWR048 | F9L | TAGTTTCTTGGAAAAATTTATTATGAGAGACATTTTC TCAGACTGGATAAATG |

TABLE 2-continued

Vaccinia Virus ORFs Having Post-Replicative Promoters

| SEQ ID NO | VACWR | VACCOP | Promoter Sequence[1] |
|---|---|---|---|
| 141 | VACWR049 | F10L | TCTATCAAACCTGGACTTTCGTTTGTAAATTGGGGCT TTTTGTACAATAAATG |
| 142 | VACWR071 | I2L | ATGAATATGATGAAGATAGCGATAAAGAAAAGCCA ATATTCAATGTATAAATG |
| 143 | VACWR076 | I7L | AACGCAGTTTGGAAAAAAGAAGATATCTGGTAAATT CTTTTCCATGATAAATG |
| 144 | VACWR078 | G1L | TACGATGATAACGACATACGAACATTACTTCCTATT TTACTCCTTAGTAAATG |
| 145 | VACWR079 | G3L | ATCTTCTGTAAGTAGGAATTTGGACAAGTTGAACAA AATTAGATCTCTAAATG |
| 146 | VACWR085 | G7L | ATTTTTATACGGATGCTCATTTTAAATTTTTGTAAAT TATTTAAAGTTAAATG |
| 147 | VACWR090 | L3L | ATGAGGTTTTCTAGCAGTAGACTCATTTAGAGAAGT TTTTTTTGTGATAAATG |
| 148 | VACWR097 | J5L | TTATTACAACTATAAAAATAATAGTTATATTTACACT TTAAATTTTTATCATG |
| 149 | VACWR102 | H4L | TAAAAAAATTATACATCATAAACCAATTTCCTAGTT GTTTGTAACTTTAAATG |
| 150 | VACWR107 | D2L | CGTTATCGTCGTTATCTACTTTGGGATACTTATTATC CTTAACTATAAAAATG |
| 151 | VACWR121 | A2.5L | TATATTAGCGCTAGACATATTACAGAACTATTTTAG ATTATGATATTTAAATG |
| 152 | VACWR126 | A7L | AAGACTTACATCATCGGTAGTAGATTTTCACTTTACC CCACGATATAAATATG |
| 153 | VACWR128 | A9L | AAAATCTAAATATGACAGATGGTGACTCTGTCTCTT TTGATGATGAATAAATG |
| 154 | VACWR129 | A10L | ATCGTTTTGTATATCCGTCACTGGTACGGTCGTCATT TAATACTAAATAAATG |
| 155 | VACWR132 | A13L | AAAAGATGATATATTGCATACTTGATCAATAGTGAA GTTATTGTCAATAAATG |
| 156 | VACWR133 | A14L | GTTTATATTCCACTTTGTTCATTCGGCGATTTAAAAT TTTTATTAGTTAAATG |
| 157 | VACWR134 | A14.5L | ATTCGTATTATTTGAGCAAGAAAATATCCCACCACC TTTTCGTCTAGTAAATG |
| 158 | VACWR137 | A17L | GGCATAAAGATTATACTCCATCTTTAATAGTGACAT TTTTTAATATATAAATG |
| 159 | VACWR140 | A21L | TGTACAGACTAAGTAATTCTTTTAAGTTAGTTAAATC AGCGCTAGAAGTCATG |
| 160 | VACWR149 | A26L | ACTTAACTCTTTTGTTAATTAAAAGTATATTCAAAAA ATGAGTTATATAAATG |
| 161 | VACWR151 | A28L | CATTGTCTGATGCGTGTAAAAAAATTTTGTCAGCTTC TAATAGATTATAAATG |
| 162 | VACWR056 | F17R | TGTATGTAAAAATATAGTAGAATTTCATTTTGTTTTT TTCTATGCTATAAATG |
| 163 | VACWR066 | E10R | TAATGCACCGAACATCCATTTATAGAATTTAGAAAT ATATTTTCATTTAAATG |
| 164 | VACWR084 | G6R | AGAACCTCAACGTAACTTAACAGTGCAACCTCTATT GGATATAAACTAATATG |
| 165 | VACWR087 | G9R | GATCAACATCTTTATGGCGTTTTTAGATTAATACTTT CAATGAGATAAATATG |

TABLE 2-continued

Vaccinia Virus ORFs Having Post-Replicative Promoters

| SEQ ID NO | VACWR | VACCOP | Promoter Sequence[1] |
|---|---|---|---|
| 166 | VACWR088 | L1R | TCAGTTTATTATCTCTCTTGGTAATATGGATACTAAT TGTAGCTATTTAAATG |
| 167 | VACWR092 | L5R | AAAAGAATATTCCTCTAACAGATATTCCGACAAAGG ATTGATTACTATAAATG |
| 168 | VACWR100 | H2R | GTAGTAGTAAGTATTTATACAAACTTTTCTTATCCAT TTATAACGTACAAATG |
| 169 | VACWR104 | H6R | AGGGAAAATCTAAAGTTGTTCGTAAAAAAGTTAAA ACTTGTAAGAAGTAAATG |
| 170 | VACWR108 | D3R | ATAAAATACTACTGTTGAGTAAATCAGTTATTTTTTT TATATCGATATTGATG |
| 171 | VACWR130 | A11L | TTGATCAAGAGTAACTATTGACTTAATAGGCATCAT TTATTTAGTATTAAATG |
| 172 | VACWR163 | A39R | CCAATTTCCATCTAATATACTTTGTCGGATTATCTAT AGTACACGGAATAATG |
| 173 | VACWR171 | A45R | CCATTGCTGCCACTCATAATATCAGACTACTTATTCT ATTTTACTAAATAATG |
| 174 | VACWR189 | B7R | TTTGTATAAATAATTATTTCAATATACTAGTTAAAAT TTTAAGATTTTAAATG |
| 175 | VACWR145 | | TCCATCCACAGACGTTACCGAACCGATTAGTGATGT GACACCATCGGTGGATG |
| 176 | VACWR207 | | ATACGAGGACGTGTATAGAGTAAGTAAAGAAAAAG AATGTGGAATTTGCTATG |

[1]The promoter sequences shown includes the ATG translation start site.

The post-replicative promoter may include a nucleic acid sequence selected from the promoter sequences listed in Table 2. The post-replicative promoter may include a functional variant of a sequence selected from those listed in Table 2. The post-replicative promoter may include a nucleic acid sequence selected from the group consisting of SEQ ID NO:84-SEQ ID NO:176. The pre-replicative promoter may include a functional variant of a nucleic acid sequence selected from the group consisting of SEQ ID NO:84-SEQ ID NO:176. The variations preferably do not significantly affect the native activity of the variant promoter. The post-replicative promoter may be the vaccinia virus I1L promoter (VACWR130). The post-replicative promoter may include SEQ ID NO: 171. It should be noted that, while not required, post-replicative promoters are generally within the 50 nucleotides immediately preceding the start of the functionally linked ORF.

As used herein, a repressor protein (repressor) is a DNA-binding protein that impedes expression of a nucleic acid sequence by a DNA-dependent RNA polymerase molecule. While not intending to be bound by theory, but merely for purposes of illustration, repressor proteins work by binding to a nucleic acid sequence (referred to as an operator), thereby blocking attachment of the polymerase to the nucleic acid molecule to be transcribed. The end result is that the polymerase is prevented from initiating transcription of the gene blocked by the repressor protein. Consequently, no transcription, or a severely reduced level of transcription (e.g., at last 80%, at least 85%, at least 95%), of the blocked gene occurs. Such prevention of transcription is referred to as repression. It will be apparent to those skilled in the art that repressors and operators are paired, meaning that a given repressor protein recognizes the sequence of one or more specific operator (operator sequence). A nucleic acid sequence encoding any repressor protein can be used to construct recombinant virus vectors of this disclosure as long as the relevant embodiments contain the appropriate operator sequence. Suitable repressor proteins for constructing recombinant virus vectors of this disclosure are known to those skilled in the art. The repressor protein may be a prokaryotic repressor protein. The repressor protein may be selected from the group consisting of lactose repressor (Lad), tetracycline repressor (TetR), tryptophan repressor (TrypR), Arabinose repressor (AraR), histidine utilization repressor (HutC). The repressor protein may be a LacI protein. The repressor protein may be encoded by a nucleic acid sequence at least 90%, at least 95%, at least 97% or at least 99% identical to a sequence selected from the group consisting of SEQ ID NO:183, SEQ ID NO:185, SEQ ID NO:187 and SEQ ID NO:189. The repressor protein may be encoded by a nucleic acid sequence selected from the group consisting of SEQ ID NO:183, SEQ ID NO:185, SEQ ID NO:187 and SEQ ID NO:189. The repressor protein may include an amino acid sequence at least 85%, at least 90%, at least 95%, at least 97% or at least 99% identical to a sequence selected from the group consisting of SEQ ID NO:184, SEQ ID NO:186, SEQ ID NO:188 and SEQ ID NO:190. The repressor protein may include an amino acid sequence selected from the group consisting of SEQ ID NO:180, SEQ ID NO:181, SEQ ID NO182 and SEQ ID NO:183.

As discussed above, a recombinant virus vector of this disclosure has an inactivating mutation in a gene required for the expression of post-replicative genes. As used herein, an inactivating mutation is a mutation in a nucleic acid sequence that abolishes the function of the protein encoded by that nucleic acid sequence. Such mutations include, but are not limited to, point mutations, deletions, including deletion of one or more nucleotide, insertions, including insertions of one or more nucleotide and substitutions, including substitutions of one or more nucleotides. Inactivating mutations may also include deletion of a portion or the entire nucleic acid sequence encoding the protein. Methods of making such mutations are known to those skilled in the art. According to this disclosure, abolishing the function of a protein refers to reducing the level of activity of a protein to such a level that the recombinant virus vector is unable to complete one round of replication (e.g., is unable to produce progeny virus). Inactivating mutations may abolish protein activity by reducing, or completely eliminating, the transcription of a gene encoding the protein. Alternatively, inactivating mutations can alter the sequence of the encoded protein, thereby reducing, or completely eliminating, the activity of the encoded protein. The inactivating mutation may reduce the level of transcription, or the level of activity of a protein, by at least 50%, at least 60%, at least 70%, at least 80%, at least 90%, at least 95% or at least 99%. The inactivating mutation may completely eliminate transcription of a gene, or the activity of a protein. As used herein, to completely eliminate transcription refers to being unable to detect transcripts from the mutated gene, or any activity of the encoded protein. The inactivating mutation may reduce the level of transcription, or protein activity, to a level low enough such that the life cycle of the virus is interrupted (e.g., the virus is unable to complete a replication cycle and produce progeny virus). The inactivating mutation may reduce the level of transcription, or protein activity, to a level low enough such that post-replicative genes are not expressed. The inactivating mutation may be in a gene required for the expression of post-replicative genes. The inactivating mutation may be in a gene encoding a transcription factor required for the expression of post-replicative genes. The inactivating mutation may be in a gene encoding a vaccinia virus transcription factor. The inactivating mutation may be in a gene selected from the group consisting of A8R (VACW127) and A23R (VACWR13).

Heretofore has been described a recombinant virus vector comprising a network of proteins and nucleic acid elements, the interaction of which functions to regulate transcription of nucleic acid sequences functionally linked to a promoter recognized by the DNA-dependent RNA polymerase. Such a recombinant virus vector is ideally suited for controlled expression of a heterologous protein.

The recombinant viral vectors of this disclosure include recombinant viral vectors comprising a third nucleic acid sequence comprising at least one polynucleotide sequence encoding at least one heterologous polypeptide, wherein the polynucleotide sequence is functionally linked to a promoter recognized by the heterologous DNA-dependent RNA polymerase encoded by the recombinant viral vector.

The third nucleic acid sequence may include a binding site (e.g., operator) for a heterologous repressor protein encoded by the recombinant virus vector, the binding site being functionally linked to the polynucleotide sequence encoding the heterologous polypeptide. The binding site is positioned such that binding of the repressor protein to the binding site impedes the heterologous DNA-dependent RNA polymerase from transcribing (e.g., blocking initiation of transcription) the polynucleotide sequence encoding the heterologous polypeptide. As used herein, the terms, impedes, impedance, and the like, refer to repression-related reduction in the level of transcription of a nucleic acid sequence, when compared to the level of transcription of the same nucleic acid sequence observed when the repressor protein is absent. According to this disclosure, such impedance may or may not refer to a total cessation of transcription. The level of transcription of the nucleic acid sequence encoding the heterologous protein may be higher in cells lacking the heterologous repressor protein than it is in cells expressing the heterologous repressor protein. Binding of the heterologous repressor protein to the operator sequence may result in a reduction of transcription of the polynucleotide sequence encoding the heterologous polypeptide of at least 50%, at least 60%, at least 70%, at least 80%, at least 90%, at least 95%, at least 97% or at least 99%. Binding of the heterologous repressor protein to the operator sequence may result in complete elimination of transcription of the polynucleotide sequence encoding the heterologous protein. According to this disclosure, the phrase complete elimination of transcription refers to an inability to detect the presence of transcripts from the polynucleotide sequence or an encoded heterologous protein. Measurement of level of transcription can be determined by measuring actual RNA transcripts, the level of the encoded heterologous polypeptide or the level of activity of the encoded polypeptide. Methods of making such measurements are known to those skilled in the art.

The promoter to which the polynucleotide sequence encoding the heterologous polypeptide is linked can be any promoter, as long as it is recognized by the heterologous DNA-dependent RNA polymerase encoded by the recombinant virus vector. The promoter recognized by the heterologous DNA-dependent RNA polymerase may be from a bacteriophage selected from the group consisting of bacteriophage T3, bacteriophage T4, bacteriophage T7 and bacteriophage SP6. The promoter recognized by the heterologous DNA-dependent RNA polymerase may be a functional variant of a promoter from a bacteriophage selected from the group consisting of bacteriophage T3, bacteriophage T4, bacteriophage T7 and bacteriophage SP6. The promoter recognized by the heterologous DNA-dependent RNA polymerase may be a bacteriophage T7 promoter. The promoter recognized by the heterologous DNA-dependent RNA polymerase may include a nucleotide sequence selected from the group consisting of SEQ ID NO:191, SEQ ID NO:192, SEQ ID NO:193, or functional variants thereof.

The operator to which the polynucleotide sequence encoding the heterologous polypeptide is linked can be any operator, as long as it is recognized by the heterologous repressor protein encoded by the recombinant virus vector. The operator recognized by the heterologous repressor protein is selected from the group consisting of a lac operator, a tet operator, a tryp operator, an ara operator and a hut operator. The sequences of such operators are known to those skilled in the art.

The polynucleotide sequence can encode any polypeptide or multiple polypeptides. The encoded polypeptide may be a therapeutic protein. Examples of useful encoded proteins include, but are not limited to an antibody, an Fc fusion proteins, an anticoagulant, a blood factor, a bone morphogenetic protein, an enzyme, a growth factor, a hormone, an interferon, an interleukin, and a thrombolytics protein. The heterologous polypeptide(s) may be an immunogenic polypeptide. As used herein, the term immunogenic refers to the ability of a specific polypeptide, or a specific region thereof, to elicit an immune response to the specific polypeptide, or to polypeptides comprising an amino acid sequence having a high degree of identity with the specific polypeptide.

According to this disclosure, two polypeptides having a high degree of identity comprise contiguous amino acid sequences that are at least 80% identical, at least 85% identical, at least 87% identical, at least 90% identical, at least 92% identical, at least 93% identical, at least 94% identical, at least 95% identical, at least 96% identical, at least 97% identical, at least 98% identical or at least 99% identical. The encoded heterologous immunogenic polypeptide may be selected from the group consisting of a viral polypeptide and a bacterial polypeptide. The encoded heterologous immunogenic polypeptide may be from a virus selected from the group consisting of adenoviruses, herpesviruses, papilloma viruses, polyomaviruses, hepadnaviruses, parvoviruses, astroviruses, calciviruses, picornaviruses, coronaviruses, flaviviruses, togaviruses, hepeviruses, retroviruses, orthomyxoviruses, arenaviruses, bunyaviruses, filoviruses, paramyxoviruses, rhabdoviruses, reoviruses, and poxviruses.

The encoded heterologous immunogenic polypeptide may be from a human immunodeficiency virus (HIV). The polynucleotide sequence may encode an HIV envelope protein, and epitope thereof, or an immunogenic portion thereof. The polynucleotide sequence may include a nucleic acid sequence at least 80% identical, at least 85% identical, at least 87% identical, at least 90% identical, at least 95% identical, at least 96% identical, at least 97% identical, at least 98% identical or at least 99% identical to SEQ ID NO:194 or SEQ ID NO:196, or a fragment thereof, wherein the fragment encodes an immunogenic polypeptide. The polynucleotide sequence may include SEQ ID NO:194 or SEQ ID NO:196, or a fragment thereof. The polynucleotide sequence may encode a polypeptide comprising an amino acid sequence at least 80% identical, at least 85% identical, at least 87% identical, at least 90% identical, at least 95% identical, at least 96% identical, at least 97% identical, at least 98% identical or at least 99% identical to SEQ ID NO:195 or SEQ ID NO:197, or an immunogenic fragment thereof. The polynucleotide sequence may encode a polypeptide comprising SEQ ID NO:195 or SEQ ID NO:197, or an immunogenic fragment thereof.

Influenza, which is commonly referred to as the flu, is caused by the infectious agent influenza virus, an RNA virus in the orthomyxovirus family. Protective immune responses against influenza virus are primarily directed to the viral hemagglutinin (HA) protein, which is a glycoprotein on the surface of the virus responsible for interaction of the virus with host cell receptors. Thus, the influenza virus HA protein makes an attractive target against which to induce an immune response by vaccination. Thus, the encoded heterologous immunogenic polypeptide may be from an influenza virus. Such viruses include, but are not limited to, human influenza virus and avian influenza virus. The polynucleotide sequence may encode an influenza hemagglutinin (HA) protein, an epitope thereof, an immunogenic portion thereof or a variant thereof. Any influenza HA protein, epitope thereof, portion thereof, or variant thereof, can be used in practicing this disclosure, as long as the HA protein, epitope thereof, portion thereof, or variant thereof induces an immune response, and preferably a protective immune response against influenza virus. Examples of useful influenza HA proteins, epitopes thereof, fragments thereof and variants thereof are disclosed in U.S. Patent Publication No. 2010/0074916, U.S. Patent Publication No. 2011/0171260, U.S. Patent Publication No. 2011/0177122 and U.S. Patent Publication No. 2014/0302079, the entire disclosures of which are incorporated herein by reference.

The polynucleotide sequence may include a nucleic acid sequence at least 80% identical, at least 85% identical, at least 87% identical, at least 90% identical, at least 95% identical, at least 96% identical, at least 97% identical, at least 98% identical or at least 99% identical to SEQ ID NO:198, or a fragment thereof, wherein the fragment encodes an immunogenic polypeptide. The polynucleotide sequence may include SEQ ID NO:198, or a fragment thereof. The polynucleotide sequence may encode a polypeptide comprising an amino acid sequence at least 80% identical, at least 85% identical, at least 87% identical, at least 90% identical, at least 95% identical, at least 96% identical, at least 97% identical, at least 98% identical or at least 99% identical to SEQ ID NO:199, or an immunogenic fragment thereof. The polynucleotide sequence may encode a polypeptide comprising SEQ ID NO:199, or an immunogenic fragment thereof.

As used herein, an immune response to the encoded heterologous polypeptide refers to the development in a subject of a humoral and/or a cellular immune response to encoded heterologous polypeptide. For purposes of this disclosure, a "humoral immune response" refers to an immune response mediated by antibody molecules, including secretory (IgA) or IgG molecules, while a "cellular immune response" is one mediated by T-lymphocytes and/or other white blood cells. One important aspect of cellular immunity involves an antigen-specific response by cytolytic T-cells ("CTL" s). CTLs have specificity for peptide antigens that are presented in association with proteins encoded by the major histocompatibility complex (MHC) and expressed on the surfaces of cells. CTLs help induce and promote the destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A cellular immune response also refers to the production of cytokines, chemokines and other such molecules produced by activated T-cells and/or other white blood cells, including those derived from CD4+ and CD8+ T-cells.

Thus, an immunological response may be one that stimulates CTLs, and/or the production or activation of helper T-cells. The production of chemokines and/or cytokines may also be stimulated. The encoded heterologous polypeptide may also elicit an antibody-mediated immune response. Hence, an immunological response may include one or more of the following effects: the production of antibodies (e.g., IgA or IgG) by B-cells; and/or the activation of suppressor, cytotoxic, or helper T-cells and/or T-cells directed specifically to the encoded heterologous polypeptide.

While the inventors have demonstrated use of this disclosure for producing several heterologous proteins, it should be appreciated that this disclosure is a delivery platform capable of delivering many diverse therapeutic molecules to cells. One type of such therapeutic molecule is therapeutic RNA. Thus, the heterologous nucleic acid molecule may encode a therapeutic RNA molecule. Therapeutic RNAs capable of being delivered to cells by recombinant virus vectors of this disclosure include, but are not limited to, inhibitors of mRNA translation (e.g., antisense molecules), molecules that interfere with RNA (e.g., RNAi), catalytically active RNA molecules (e.g., ribozymes) and RNAs that bind proteins and other ligands (e.g., aptamers). Methods of producing such molecules are known to those skilled in the art and are also disclosed in U.S. Patent Publication No. 2014/0303073, U.S. Patent Publication No. 2012/0232128, U.S. Patent Publication No. 2011/0118334, U.S. Patent Publication No. 2011/0033859, U.S. Patent Publication No. 2006/0089323, U.S. Patent Publication No. 2012/0263782, U.S. Patent Publication No. 2012/0301449, and U.S. Patent Publication No. 2004/0137429, the entire disclosures of which are incorporated herein by reference.

From the description thus far, it will be apparent to one skilled in the art that the benefits of this disclosure arise from functional interaction of a novel combination of elements. Specific embodiments are now described in order to illustrate these interactions and the benefits thereof. It should be understood that the description of this specific embodiment is for illustrative purposes only and it is not intended to be limiting in any way on the scope of this disclosure, as other embodiments can be produced using other viruses and elements disclosed herein.

A specific recombinant vaccinia virus vector may include:

a) a first nucleic acid sequence encoding a polymerase selected from the group consisting of bacteriophage T7 RNA polymerase, bacteriophage T3 RNA polymerase and a bacteriophage SP6 RNA polymerase, wherein the first nucleic acid sequence is functionally linked to the vaccinia virus thymidine kinase promoter (VACVWR094); and, b) a second nucleic acid sequence encoding a repressor protein selected from the group consisting of a bacterial lad repressor protein, a bacterial trp repressor protein, a bacterial tet repressor protein and a bacterial lexA repressor protein, wherein the second nucleic acid sequence is functionally linked to the vaccinia virus I1L (VACVWR070) promoter The first and second nucleic acid sequences are inserted between the F12 and F13 ORFs of the recombinant vaccinia virus vector. The A23R (VACWR143) ORF of the recombinant vaccinia virus vector comprises at least one inactivating mutation. This recombinant vaccinia virus vector is capable of replicating its genome.

One recombinant vaccinia virus vector includes:

a) a first nucleic acid sequence encoding a polymerase selected from the group consisting of bacteriophage T7 RNA polymerase, bacteriophage T3 RNA polymerase and a bacteriophage SP6 RNA polymerase, wherein the first nucleic acid sequence is functionally linked to the vaccinia virus thymidine kinase promoter (VACVWR094);

b) a second nucleic acid sequence encoding a bacterial lad repressor protein, a bacterial trp repressor protein, a bacterial tet repressor protein and a bacterial lexA repressor protein, wherein the second nucleic acid sequence is functionally linked to the vaccinia virus I1L (VACVWR070) promoter; and, c) a third nucleic acid sequence comprising a polynucleotide sequence encoding a heterologous protein selected from the group consisting of luciferase, HIV envelope protein and influenza virus hemagglutinin protein, wherein the polynucleotide sequence is functionally linked to a promoter selected from the group consisting of a bacteriophage T7 RNA polymerase promoter, a bacteriophage T3 RNA polymerase promoter and a bacteriophage SP6 RNA polymerase promoter; wherein the third nucleic acid sequence comprises an operator sequence positioned such that binding of the repressor protein to the operator sequence impedes transcription of the polynucleotide sequence by the bacteriophage polymerase; and an untranslated leader (UTR) that enhances translation;

The first and second nucleic acid sequences are inserted between the F12 and F13 ORFs of the recombinant vaccinia virus vector. The third nucleic acid sequence is inserted within the non-essential A56R gene. The A23R (VACWR143) ORF of the recombinant vaccinia virus vector comprises at least one inactivating mutation. This recombinant vaccinia virus vector is capable of replicating its genome.

Figure 10:
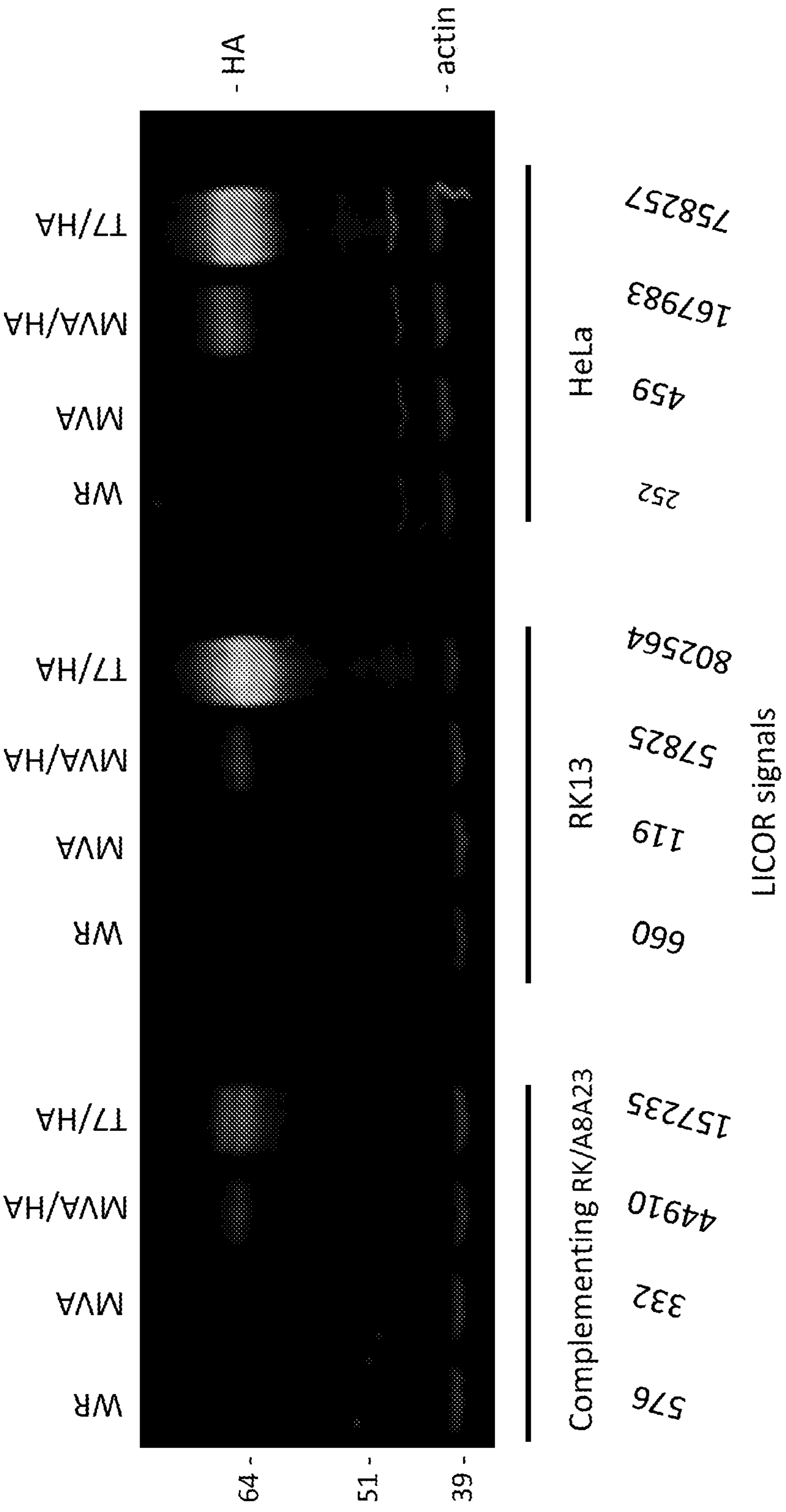
FIG. 10 is a Western blot, and LICOR quantitation of hemagglutinin bands, of influenza HA expression from T7/HA in three cell lines.
Figure 17:
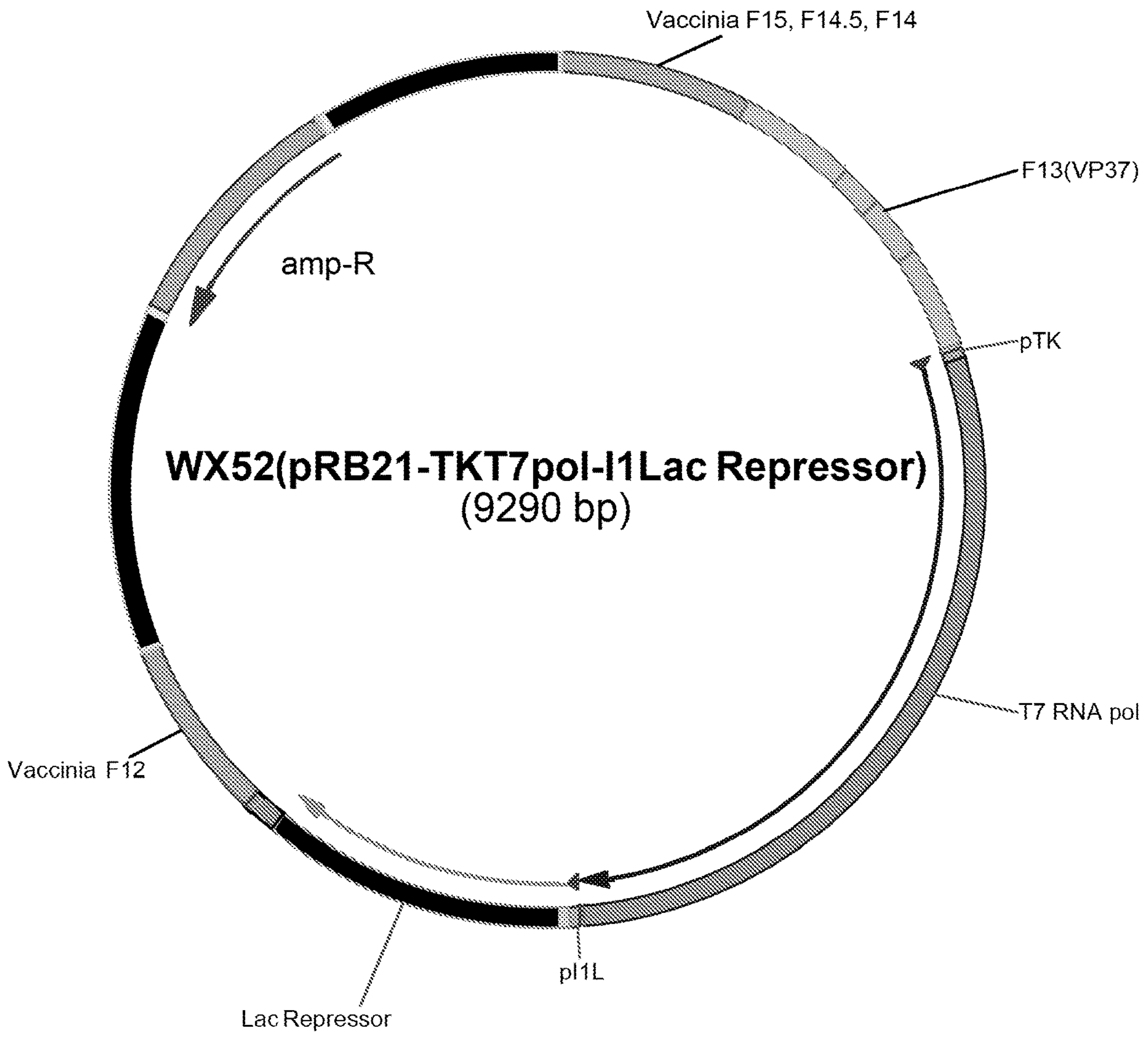
FIG. 17 depicts a viral vector construct map of a viral vector (WX52(pRB21-TKT7pol-I1Lac Repressor)) of this disclosure.

Schematic illustrations of such embodiments are shown in FIGS. 1, 10 and 17. It will be apparent to one skilled in the art that because the above-described recombinant vaccinia virus vector comprises an inactivating mutation in the A23R ORF, which encodes a vaccinia virus transcription factor necessary for expression of vaccinia virus intermediate (i.e., post-replicative) ORFs, upon infecting a regular cell, such a recombinant vaccinia virus vector would not be able to express intermediate or late ORFs. Consequently, such a recombinant vaccinia virus vector would be unable to complete its replication cycle. However, if the recombinant vaccinia virus vector is used to infect a recombinant cell expressing a recombinant version of the vaccinia virus A23 protein (referred to as a complementing cell line), the recombinant A23 protein would provide the missing transcription factor function and consequently, the recombinant vaccinia virus vector would be able to complete its replication. Thus, by using such complementing cell line, the recombinant vaccinia virus could be grown to high titers.

Regarding expression of the heterologous protein in such a complementing cell line, because the first nucleic acid sequence encoding the bacteriophage RNA polymerase (e.g., T7 RNA polymerase) is functionally linked to a pre-replicative promoter, upon infection of the complementing cell the pre-replicative promoter drives expression of the bacteriophage polymerase ORF and consequently, the bacteriophage RNA polymerase will be produced. The bacteriophage RNA polymerase will recognize, and bind to, the bacteriophage RNA polymerase promoter that is functionally linked to the ORF encoding the heterologous protein and consequently, the heterologous protein will be produced. However, following replication of the recombinant vaccinia virus vector genome, post-replicative transcription factors will be produced. Because the repressor protein (e.g., lad) is functionally linked to a post-replicative promoter, the post-replicative transcription factors will recognize the post-replicative promoter, resulting in production of bacterial repressor protein. The bacterial repressor protein will bind to the operator sequence, thereby causing repression of production of the heterologous protein. The end result of this interacting network is that by using the complementing cell line, high titers of recombinant vaccinia virus vector can be produced with minimal production of the heterologous protein. The scenario outlined above is depicted in FIG. 2A.

In contrast to the above, infection of a non-complementing cell with the recombinant vaccinia virus vector results in a very different outcome. As with the complementing cell, because the first nucleic acid sequence encoding the bacteriophage RNA polymerase (e.g., T7 RNA polymerase) is functionally linked to a pre-replicative promoter, upon infection of the non-complementing cell the pre-replicative promoter drives expression of the bacteriophage RNA polymerase ORF and consequently, bacteriophage RNA polymerase will be produced. The bacteriophage RNA polymerase will recognize, and bind to, the bacteriophage RNA promoter (e.g., T7 RNA polymerase promoter) that is functionally linked to the ORF encoding the heterologous protein and consequently, the heterologous protein will be produced. However, in contrast to the complementing cell line described above, the non-complementing cell does not provide the A23R function. Therefore, because the recombinant vaccinia virus vector comprises an inactivating mutation in the A23R ORF, following replication of its genome, the recombinant vaccinia virus vector will be unable to produce post-replicative proteins required for expression from ORFs functionally linked to post-replicative promoters. Consequently, replication of the recombinant vaccinia virus vector will stall. Additionally, because the bacterial repressor protein is functionally linked to a post-replicative promoter, it will not be produced and the bacteriophage RNA polymerase, which will be continually produced, continues to cause expression of the heterologous protein. Thus, the result of infecting a non-complementing cell with a recombinant vaccinia virus vector is that no further recombinant vaccinia virus particles will be produced, but the cell will produce a large amount of the heterologous. Such a scenario is depicted in FIG. 2B.

Figure 2A:
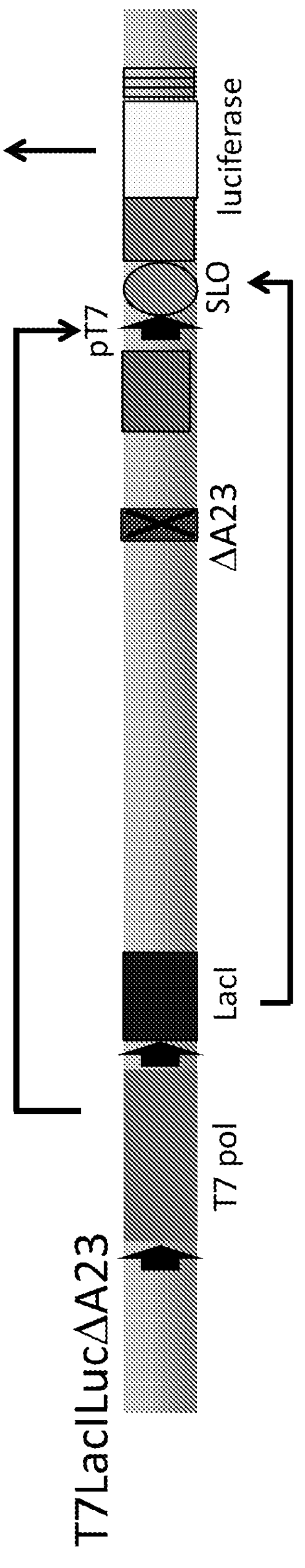
FIGS. 2A and 2B show the expected expression results of complementing and non-complementing vectors, respectively, according to this disclosure.
Figure 2B:
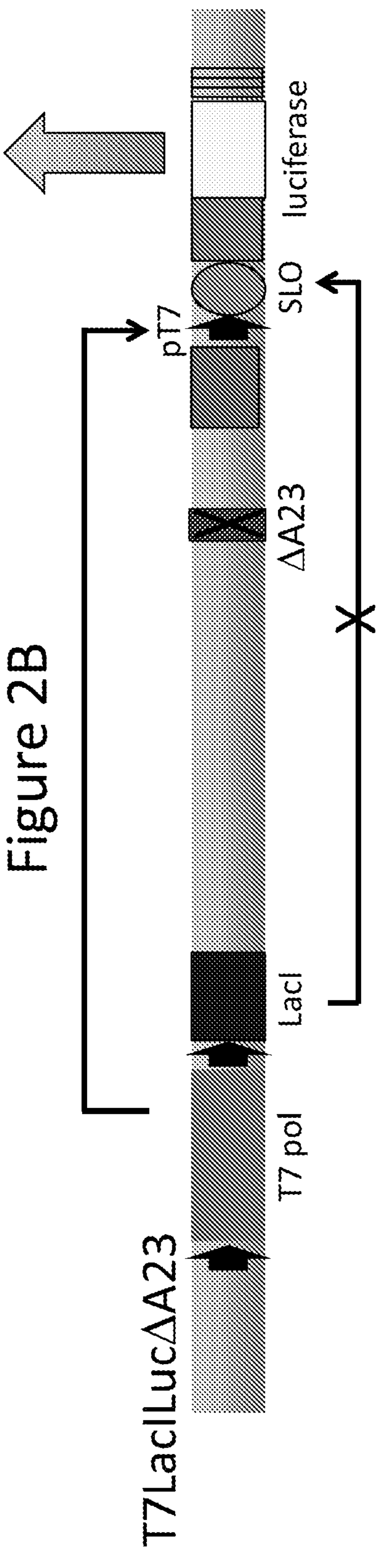

It should be appreciated that the scenario illustrated in FIG. 2A represents growth of the recombinant vaccinia virus vector in cell culture, while the scenario illustrated in FIG. 2B represents infection of a non-recombinant cell, such as when recombinant vaccinia virus vector is administered to an individual. Thus, such use of complementing cells represents a system for producing a vaccine. One aspect of this disclosure is a system for producing high titers of recombinant virus vectors of this disclosure, the system comprising:

1) a recombinant virus vector comprising:
   a) a first nucleic acid sequence encoding a heterologous DNA-dependent RNA polymerase, wherein the first nucleic acid sequence is functionally linked to a pre-replicative promoter;
   b) a second nucleic acid sequence encoding heterologous repressor protein, wherein the second nucleic acid sequence is functionally linked to a post-replicative promoter; and,
   c) at least one inactivating mutation in a virus gene required for the expression of post-replicative genes; wherein the recombinant viral vector is capable of replicating the viral genome when introduced into a cell; and,
   d) a third nucleic acid sequence comprising at least one polynucleotide sequence encoding at least one heterologous polypeptide functionally linked to a promoter recognized by the heterologous DNA-dependent RNA polymerase and an operator recognized by the heterologous repressor.
2) a recombinant complementing cell, wherein the recombinant complementing cell comprises a heterologous nucleic acid molecule encoding the virus gene required for expression of post-replicative genes functionally linked to a promoter such that the recombinant complementing cell is capable of expressing the viral protein required for expression of post-replicative genes.

Any cell can be used in a system of this disclosure, as long as the cell is capable of being infected by, and is capable of supporting replication of, the recombinant virus vector. Exemplary cells from which to construct complementing cells include, but are not limited to, RK13 cells, Vero cells and HeLa cells.

The inventors have discovered that one benefit of the constructs and systems disclosed herein is that they allow production of high titer, recombinant virus vector stocks in which the heterologous insert is stably maintained. According to the present disclosure, stably maintained, stably inserted, stable insertions, and the like, refer to maintenance of the presence or expression of the inserted heterologous DNA in a recombinant virus vector population. Without intending to be bound by theory, it is believed that such maintenance can be enhanced by strong repression of expression of the heterologous DNA, when the recombinant virus vector is grown in a complementing cell. It is well understood by those skilled in the art that during replication of a viral population, any alteration (e.g., mutation) that provides a particular virus with a growth advantage results in that particular virus overgrowing other viruses in the population and becoming the dominant virus in the final population. An example of one such alteration is a mutation in the viral genome that results in failure to express the inserted heterologous DNA or causes expression of an inactive protein. Without intending to be bound by bound by theory, it is believed that such an alteration (e.g., mutation) may confer a growth advantage by freeing up resources (e.g., proteins, amino acids, nucleotides, etc.) that can be used to produce more virus, or by inactivating a protein deleterious to the infected cell (e.g., a toxin). In such an example, the mutated virus, having a growth advantage, will outgrow viruses expressing active protein encoded by the heterologous insert, and will eventually become the dominant virus in the population. However, in a system of this disclosure, a recombinant virus vector having a mutation in the inserted heterologous DNA, or sequences necessary for the expression thereof, will lack any advantage. This is because, as described herein, systems of this disclosure comprise complementing cells that provide the function lost by the virus due to the inactivating mutation (e.g., the vaccinia A23 protein or A8 protein). When a recombinant viral vector of this disclosure is introduced into such a cell, the viral vector is able to replicate and consequently, post-replicative genes, including post-replicative transcription factors, are produced. Because the heterologous repressor protein is driven by a post-replicative promoter, repressor protein is produced and binds to the operator, thereby repressing expression of the inserted heterologous DNA. If the heterologous DNA is not highly expressed by the recombinant virus vector, there is no growth advantage to be had by viruses that develop mutations in the heterologous DNA, or sequences necessary for expression thereof. Lacking any growth advantage, viruses developing such mutations will be unable to overgrow recombinant viral vectors maintaining the inserted heterologous DNA, or any activity encoded thereby, and the vast majority of the population will be recombinant viral vectors maintaining the inserted heterologous DNA, or any activity encoded thereby. Thus, expression of the inserted heterologous DNA will be stably maintained within the population.

With further regard to the stability of inserted, heterologous DNA, the inventors have previously discovered that such stability can be enhanced by the use of specific sites within the viral genome. For example, it is well appreciated by those skilled in the art the loss of exogenous DNA from a viral genome is frequently due to recombinogenic events occurring between the genomic nucleic acid sequences flanking the insertion site of the exogenous nucleic acid sequences during replication, a process referred to as recombining out the exogenous nucleic acid sequences. Such a loss is particularly likely if, for example, the exogenous nucleic acid sequence confers on the recombinant virus some growth disadvantage. For example, it may encode a protein deleterious to growth, or the exogenous nucleic acid sequences may simply increase the demand for resources needed for the virus to replicate. The end result is that viruses lacking the exogenous nucleic acid sequences will have a growth advantage and will therefore become more prominent in the population.

The present inventors have discovered that by applying the principles outlined above, it is possible to ensure that recombinant viruses comprising exogenous nucleic acid sequences remain the prominent viruses in a population. Specifically, the process of recombining out described above often results in deletion, or rearrangement, of the genomic nucleic acid sequences flanking the inserted exogenous nucleic acid sequences. It will be appreciated by those skilled in the art that if such flanking sequences have an effect on viral replication (e.g., encode proteins necessary for viral replication), such deletion or rearrangement will negatively impact the ability of the virus to replicate. Consequently, progeny viruses containing such deletions or rearrangements will have an impaired ability to replicate relative to viruses in the population that have not undergone such deletion or rearrangement. The result will be that, over time, the impaired virus will become less prominent in the overall population. Theoretically, given enough rounds of replication, the impaired virus will disappear from the population and the vast majority of viruses in the population will be those that did not recombine out the inserted exogenous nucleic acid sequences. Thus, the inserted nucleic acid sequences will be maintained within the population. Detailed methods for producing such viruses are disclosed herein and can also be found in U.S. Pat. Nos. 9,133,478, and 9,133,480, the entire disclosures of which are incorporated herein by reference. From the discussion above, it should be apparent to those skilled in the art that the phrase stable insertion does not indicate that no recombinant virus vector will lose the inserted nucleic acid sequences upon replication. It refers instead to the fact that recombinant virus vectors that do lose their inserted nucleic acid sequences during replication will be at a growth disadvantage and, over time, those viruses will produce less progeny resulting in that genotype being reduced in, or absent from, the resulting virus population altogether. Thus, it will be appreciated that the genomic locations into which the exogenous nucleic acid sequences are inserted have a significant impact on the stability of the exogenous nucleic acid sequences.

Thus, recombinant virus vector of this disclosure can be designed such that when the recombinant virus vectors are replicated in culture, the inserted nucleic acid sequences are not lost from the majority of population. As used herein, the majority of the population refers to a population in which at least 50%, at least 60%, at least 70%, at least 75%, at least 80%, at least 85%, at least 90% or at least 95% of the progeny resulting from replication of a recombinant virus vector retain the inserted nucleic acid sequences.

The recombinant viral vector may include a third nucleic acid sequence comprising a polynucleotide sequence encoding a heterologous polypeptide, wherein the polynucleotide sequence is functionally linked to a promoter recognized by the heterologous DNA-dependent RNA polymerase encoded by the recombinant virus vector. The third nucleic acid sequence may further comprise an operator for the heterologous repressor protein encoded by the recombinant virus vector, functionally linked to the polynucleotide sequence encoding the heterologous polypeptide. The binding site is positioned such that binding of the repressor protein to the binding site impedes the heterologous DNA-dependent RNA polymerase from initiating transcription of the polynucleotide sequence encoding the heterologous polypeptide. A further option is to provide an untranslated leader sequence before the ORF to enhance translation.

One aspect of this disclosure is a method for producing a composition comprising a high titer of recombinant virus vectors of this disclosure, the method comprising contacting a recombinant virus vector of this disclosure with recombinant cell comprising a heterologous nucleic acid molecule comprising the virus ORF required for expression of post-replicative genes functionally linked to a promoter such that the recombinant cell is capable of expressing the viral ORF required for expression of post-replicative genes; and isolating recombinant virus vector particles from the mixture of the recombinant virus vector and the recombinant cell. The composition may include at least $1\times10^5$, at least $1\times10^6$, at least $1\times10^7$, at least $1\times10^8$ or at least $1\times10^9$ recombinant virus vector particles per milliliter.

One aspect of this disclosure is a method for treating an individual for an illness, the method comprising administering to the individual a recombinant virus vector of this disclosure, wherein the heterologous polypeptide encoded by the recombinant virus vector is a therapeutic polypeptide capable of treating the illness. The terms individual, subject, and patient are well-recognized in the art, and are herein used interchangeably to refer to any human, or other animal, susceptible to infection by a recombinant virus vector of this disclosure. Examples include, but are not limited to, humans and other primates, including non-human primates such as chimpanzees and other apes and monkey species; farm animals such as cattle, sheep, pigs, seals, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The terms individual, subject, and patient by themselves, do not denote a particular age, sex, race, and the like. Thus, individuals of any age, whether male or female, are intended to be covered by the present disclosure and include, but are not limited to the elderly, adults, children, babies, infants, and toddlers. Likewise, the methods of this disclosure can be applied to any race, including, for example, Caucasian (white), African-American (black), Native American, Native Hawaiian, Hispanic, Latino, Asian, and European.

One aspect of this disclosure is a method for treating an individual for an illness, the method comprising administering to the individual a recombinant virus vector of this disclosure, wherein the third nucleic acid sequence comprises a polynucleotide sequence encoding a therapeutic RNA that is capable of treating the illness.

One aspect of this disclosure is a method for eliciting an immune response in an individual, the method comprising administering to the individual a recombinant viral vector of this disclosure, wherein a heterologous polypeptide encoded by the recombinant viral vector is an immunogenic polypeptides. The recombinant viral vector may encode more than one heterologous polypeptide. The immunogenic polypeptide may be from a virus selected from the group consisting of adenoviruses, herpesviruses, papilloma viruses, polyomaviruses, hepadnaviruses, parvoviruses, astroviruses, calciviruses, picornaviruses, coronaviruses, flaviviruses, togaviruses, hepeviruses, retroviruses, orthomyxoviruses, arenaviruses, bunyaviruses, filoviruses, paramyxoviruses, rhabdoviruses, reoviruses, and poxviruses.

One aspect of this disclosure is a method for vaccinating an individual, the method comprising administering to the individual a recombinant virus vector of this disclosure, wherein the heterologous polypeptide encoded by the recombinant virus vector is an immunogenic polypeptide. The immunogenic polypeptide may be from a virus selected from the group consisting of adenoviruses, herpesviruses, papilloma viruses, polyomaviruses, hepadnaviruses, parvoviruses, astroviruses, calciviruses, picornaviruses, coronaviruses, flaviviruses, togaviruses, hepeviruses, retroviruses, orthomyxoviruses, arenaviruses, bunyaviruses, filoviruses, paramyxoviruses, rhabdoviruses, reoviruses, and poxviruses.

The present disclosure also provides tools useful for producing recombinant viral vectors of this disclosure. Thus, a nucleic acid molecule may include a pre-replicative promoter of this disclosure functionally linked to a gene encoding a DNA-dependent RNA polymerase of this disclosure. The nucleic acid molecule can be a linear molecule (e.g., one produced by recombinant PCR techniques), or it can be a circular molecule such as, a plasmid. The pre-replicative promoter may be selected from the promoters listed in Table 1. The pre-replicative promoter may be a functional variant of a promoter sequence listed in Table 1. The pre-replicative promoter may include a sequence at least 90%, at least 95%, at least 97% or at least 97% identical to a promoter sequence from Table 1, wherein the variations in sequence do not significantly affect the promoter function. The pre-replicative promoter may include a sequence at least 90%, at least 95%, at least 97% or at least 97% identical to a sequence selected from the group consisting of SEQ ID NO:1-SEQ ID NO:83, wherein the variations in sequence do not significantly affect the promoter function. The pre-replicative promoter may include a sequence selected from the group consisting of SEQ ID NO:1-SEQ ID NO:83. The DNA-dependent RNA polymerase may be a bacteriophage-induced DNA-dependent RNA polymerase. The DNA-dependent RNA polymerase may be a single subunit phage DNA-dependent RNA polymerase. The DNA-dependent RNA polymerase may be from a bacteriophage selected from the group consisting of bacteriophage T3, bacteriophage T4, bacteriophage T7 and bacteriophage SP6. The DNA-dependent RNA polymerase may be encoded by a nucleic acid molecule comprising a nucleic acid sequence at least 90%, at least 95%, at least 97% or at least 99% identical to a sequence selected from the group consisting of SEQ ID NO:177, SEQ ID NO:179 and SEQ ID NO:181. The DNA-dependent RNA polymerase may be encoded by a nucleic acid molecule comprising a nucleic acid sequence selected from the group consisting of SEQ ID NO:177, SEQ ID NO:179 and SEQ ID NO:181. The heterologous DNA-dependent RNA polymerase may include an amino acid sequence at least 90%, at least 95%, at least 97% or at least 99% identical to a sequence selected from the group consisting of SEQ ID NO:178, SEQ ID NO:180 and SEQ ID NO:182. The heterologous DNA-dependent RNA polymerase may include an amino acid sequence selected from the group consisting of SEQ ID NO:178, SEQ ID NO:180 and SEQ ID NO:182. The heterologous DNA-dependent RNA polymerase may be a bacteriophage T7 DNA-dependent RNA polymerase. The pre-replicative promoter and the functionally linked gene encoding the DNA-dependent RNA polymerase are physically linked and the linked molecule flanked by sequences from a virus. The flanking sequences may be from a poxvirus.

One embodiment of this disclosure provides a nucleic acid molecule comprising a post-replicative promoter of this disclosure functionally linked to a gene encoding a repressor protein of this disclosure. The nucleic acid molecule can be a linear molecule (e.g., one produced by recombinant PCR techniques), or it can be a circular molecule such as, for example, a plasmid. The post-replicative promoter may be selected from the promoters listed in Table 2. The post-replicative promoter may be a functional variant of a promoter sequence listed in Table 2. The post-replicative promoter may include a sequence at least 90%, at least 95%, at least 97% or at least 97% identical to a promoter sequence from Table 2, wherein the variations in sequence do not significantly affect the promoter function. The post-replicative promoter may include a sequence at least 90%, at least 95%, at least 97% or at least 97% identical to a sequence selected from the group consisting of SEQ ID NO:84-SEQ ID NO:176, wherein the variations in sequence do not significantly affect the promoter function. The post-replicative promoter may include a sequence selected from the group consisting of SEQ ID NO:84-SEQ ID NO:176. The repressor protein may be prokaryotic repressor protein. The repressor protein may be selected from the group consisting of lactose repressor (Lad), tetracycline repressor (TetR), tryptophan repressor (TrypR), Arabinose repressor (AraR), histidine utilization repressor (HutC). The repressor protein may be a LacI protein. The repressor protein may be encoded by a nucleic acid sequence at least 90%, at least 95%, at least 97% or at least 99% identical to a sequence selected from the group consisting of SEQ ID NO:183, SEQ ID NO:185, SEQ ID NO:187 and SEQ ID NO:189. The repressor protein may be encoded by a nucleic acid sequence selected from the group consisting of SEQ ID NO:183, SEQ ID NO:185, SEQ ID NO:187 and SEQ ID NO:189. The repressor protein may include an amino acid sequence at least 85%, at least 90%, at least 95%, at least 97% or at least 99% identical to a sequence selected from the group consisting of SEQ ID NO:184, SEQ ID NO:186, SEQ ID NO:188 and SEQ ID NO:190. The repressor protein may include an amino acid sequence selected from the group consisting of SEQ ID NO:180, SEQ ID NO:181, SEQ ID N0182 and SEQ ID NO:183. The post-replicative promoter and the functionally linked gene encoding the repressor protein may be physically linked and the linked molecule flanked by sequences from a virus. The flanking sequences may be from a poxvirus.

One embodiment of this disclosure is a nucleic acid molecule comprising SEQ ID NO:200, and variants thereof, that are capable of functioning to construct a recombinant viral vector of this disclosure.

One embodiment of this disclosure is a nucleic acid sequence that is heterologous to a virus recited herein, functionally linked to a promoter sequence recognized by a DNA-dependent RNA polymerase of this disclosure, wherein the heterologous nucleic acid sequence is flanked by polynucleotide sequences from a virus recited herein, wherein the flanking polynucleotide sequences are both from the same virus. The heterologous nuclei acid sequence may encode a therapeutic protein, an immunogenic protein or a therapeutic RNA molecule. The flanking polynucleotide sequences may be from a poxvirus. One embodiment of this disclosure is a nucleic acid molecule comprising a sequence selected from the group consisting of SEQ ID NO:203, SEQ ID NO:205, and variants thereof that are capable of functioning to construct a recombinant viral vector of this disclosure.

One embodiment of this disclosure is a nucleic acid molecule comprising a sequence selected from the group consisting of SEQ ID NO:201, SEQ ID NO:204, and variants thereof that are capable of functioning to construct a recombinant viral vector of this disclosure.

This disclosure also includes kits suitable for producing compositions comprising recombinant virus vectors of this disclosure. Kits can include, for example, recombinant virus vectors of this disclosure, nucleic acid molecules for constructing recombinant virus vectors of this disclosure, and/or complementing cells for growing recombinant virus vectors of this disclosure. Kits may also comprise associated components, such as, but not limited to, proteins, enzymes, cell culture media, buffers, labels, containers, vials, syringes, instructions for using the kit and the like.

EXAMPLES

The following examples are put forth to provide those of ordinary skill in the art with a complete disclosure and description of how to make and use the embodiments, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, and temperature is in degrees Celsius. Standard abbreviations are used.

Example 1

This example demonstrates the construction of vectors of this disclosure used for further expression testing. FIG. 1A shows the scheme for inserting a bacteriophage T7 RNA polymerase gene, under the control of the vaccinia virus thymidine kinase (TK) promoter, and the *E. coli* lac repressor gene, under the control of the vaccinia I1L promoter, between the F12-F13 genes in WR strain of vaccinia by homologous recombination. Briefly, DNA comprising the bacteriophage T7 RNA polymerase gene linked to the vaccinia virus TK promoter, and the lac repressor gene linked to the vaccinia virus promoter vaccinia virus I1L promoter, was cloned between the XhoI and XmaI sites of plasmid vector pRB21 (Blasco and Moss, 1995). The resulting transfer plasmid named WX52 was transfected into cells infected with the virus vRB12 (Blasco and Moss, 1995) and the new recombinant virus vT7LacI was isolated (See FIG. 1A).

FIG. 1B shows the scheme for inserting the luciferase gene into the A56 gene of the vT7LacI virus. Briefly, DNA encoding the firefly luciferase was inserted following the T7 promoter, lac operator and untranslated EMC leader (UTR) in a modified pVote.1 plasmid (Ward et al. 1995) containing DNA encoding the GFP gene instead of the *E. coli* gpt gene, to form the transfer plasmid pVotegfpluc. The pVotegfpluc plasmid was transfected into cells infected with vT7LacI virus and the new recombinant virus, named vT7LacILuc, was isolated.

FIG. 1C shows the scheme for producing the final virus, named T7LacILucΔA23. Briefly, DNA containing the DsRED ORF controlled by the p11 promoter and flanked by sequences from the A22R and A24R gene, which retained only a small segment of the A23 open reading frame (Warren et al. 2012), was transfected into cells infected with the vT7LacILuc virus and the new recombinant virus, vT7LacILucΔA23, was isolated. In the vT7LacILucΔA23 virus, most of the A23 gene is missing and the region between the A22 and A24 genes has been interrupted by the DsRED ORF. The result is that the vT7LacILucΔA23 virus does not produce the A23 intermediate transcription factor.

Example 2

This example shows the expected effect on Luciferase expression from the T7LacILucΔA23 virus produced in Example 1, in complementing cells and noncomplementing cells. FIG. 2A indicates that in the complementing cell line, RK/A8A23, T7 RNA polymerase expression is regulated by the weak early TK promoter and transcribes the target gene. However, the *E. coli* lac repressor gene, lad, under the control of a strong intermediate promoter, I1L, is transcribed abundantly and the repressor protein binds the lac operator (SLO) to minimize transcription of the target gene. FIG. 2B shows that in the non-complementing cell lines, RK13 and HeLa, T7 RNA polymerase will selectively transcribe the target gene with T7 promoter in replicated viral DNA in the absence of vaccinia virus intermediate and late transcription. Therefore, only the target protein is abundantly synthesized in these cells.

Example 3

Figure 3:
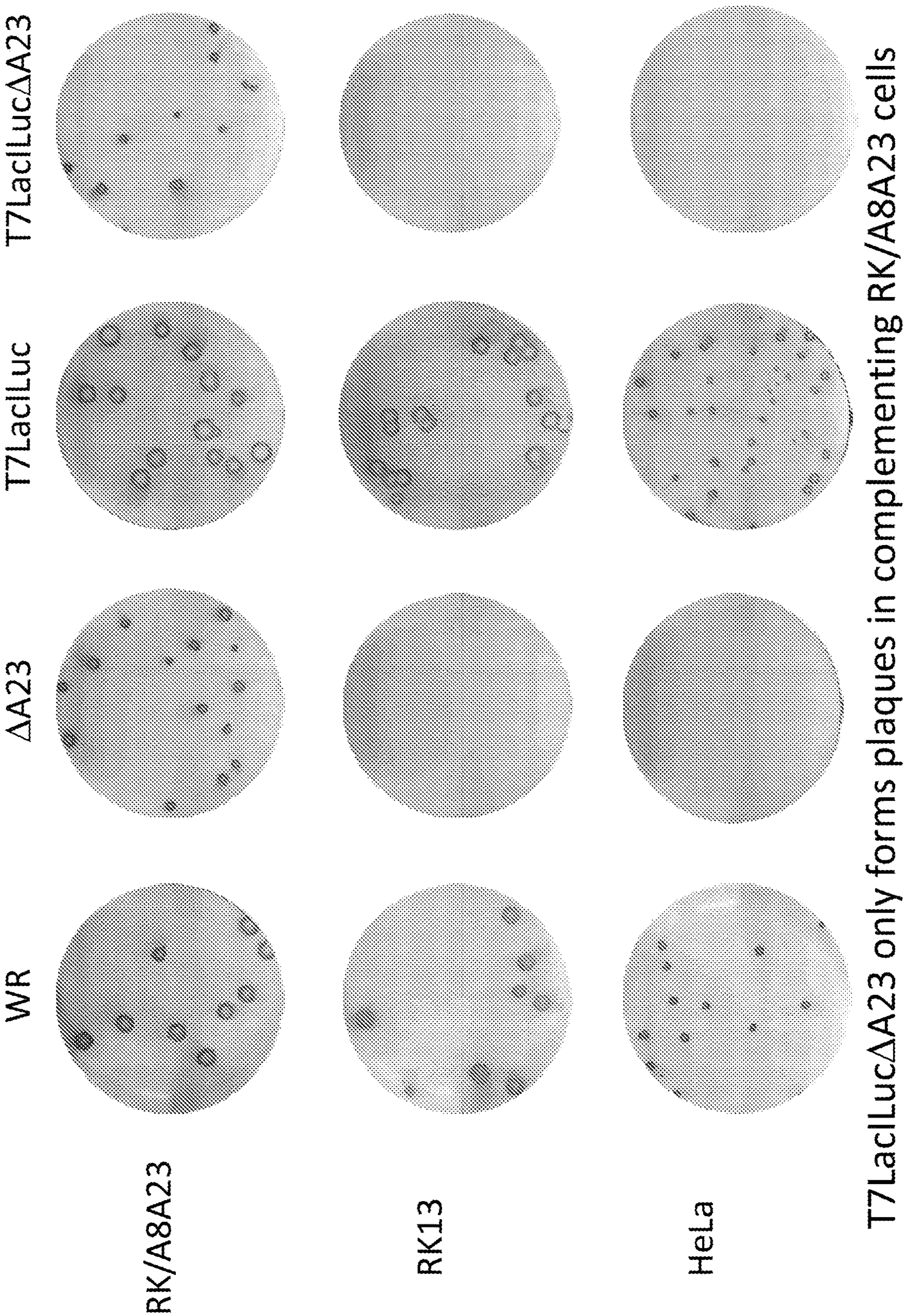
FIG. 3 shows the plaque size of four viruses in three cell lines.

This example demonstrates the selective replication of the vectors of this disclosure. Infected cells were fixed at three days and immunostained with anti-vaccinia serum. FIG. 3 shows the resulting plaque size of four viruses in three cell lines. The viruses, WR and T7LacILuc, formed similar plaques in the 3 cell lines, RK/A8A23, RK13 and HeLa. The new prototype vector, T7LacILucΔA23, in which the intermediate transcription factor, gene A23, has been knocked out, only formed plaques in the complementing RK/A8A23 cell line.

Example 4

Figure 4:
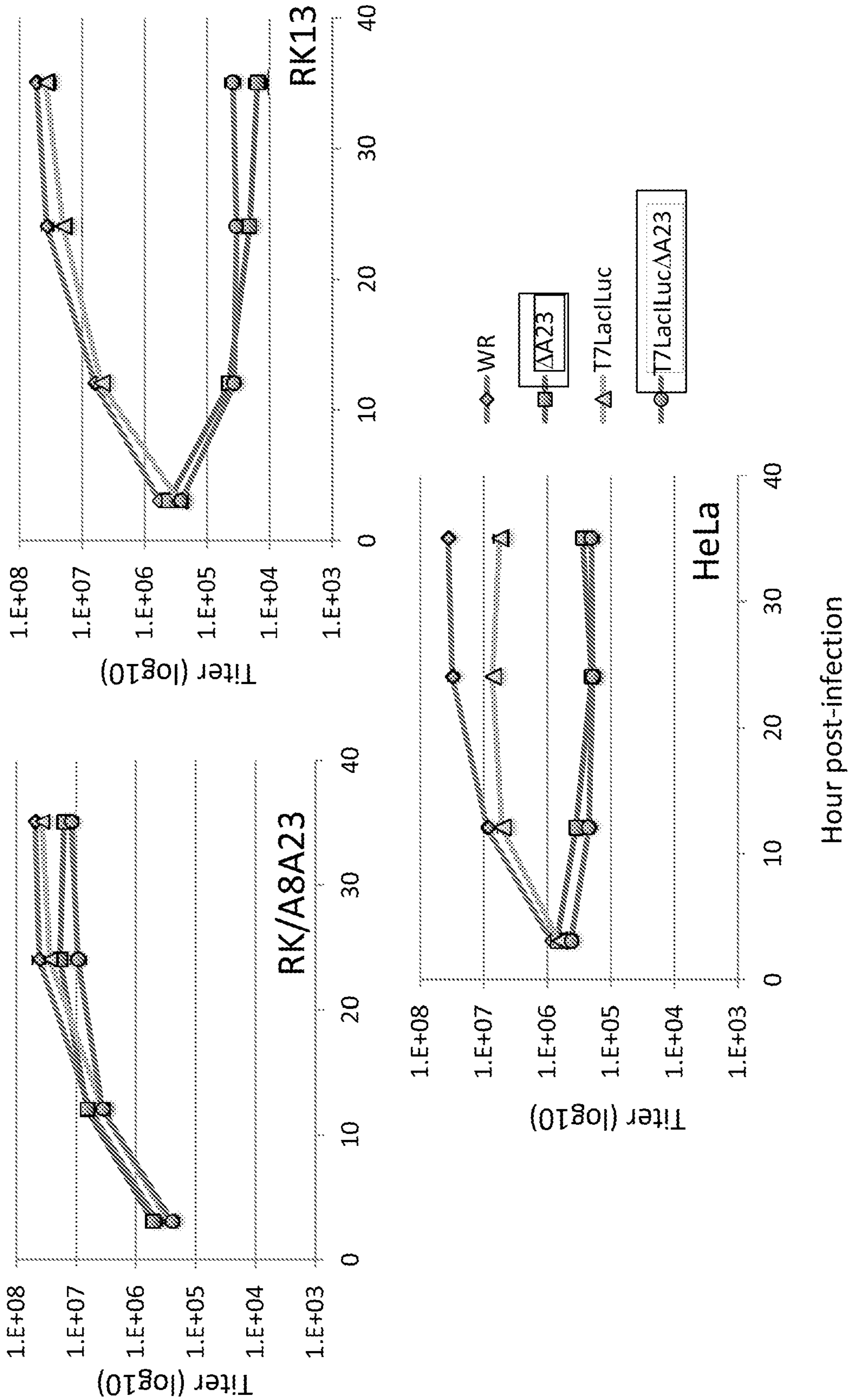
FIG. 4 shows one step growth curves for viruses in RK/A8A23, RK13 and HeLa cells, showing that T7LacILucDA23 only replicates in RK/A8A23 cells.
Figure 5:
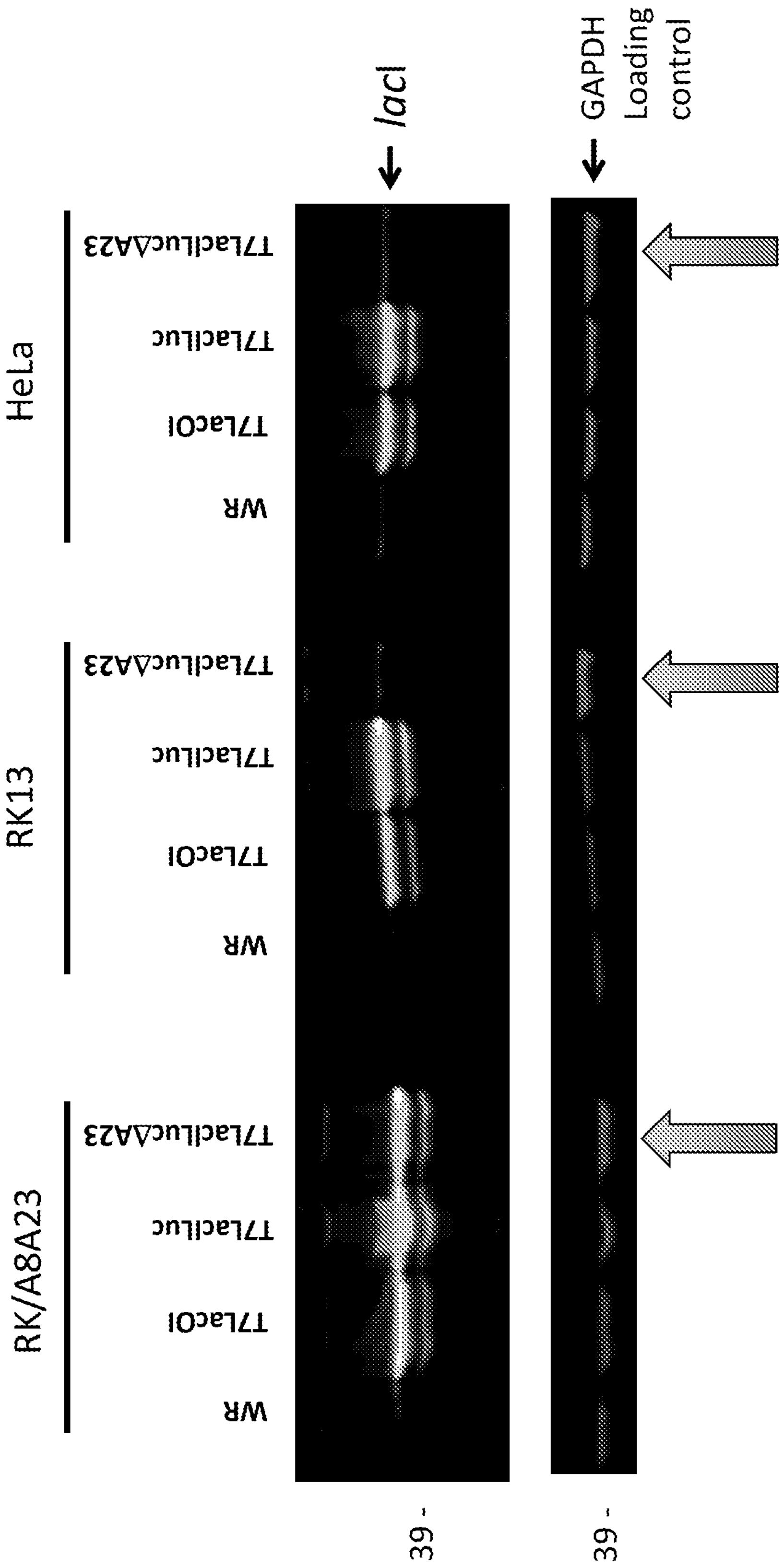
FIG. 5 shows a Western blot comparison of lac repressor expression by viruses in complementing and non-complementing cells. The arrows indicate that T7LacILucDA23 only expresses lad in RK/A8A23 cells.

This example further demonstrates selective replication of the vectors of this disclosure. FIG. 4 shows the one-step growth curve of WR, ΔA23, T7LacILuc, and T7LacILucΔA23 (MOI=3) performed in the three cell lines. At specified times, samples in triplicate were taken and titered in RK/A8A23 cell line. The prototype T7LacILucΔA23 virus replicated only in the complementing cell line, RK/A8A23.

Example 5

This example demonstrates the selective expression of the repressor in complementing cells. RK/A8A23, RK13 and HeLa cells were infected at an MOI of 5 by WR, T7LacOI (positive control), T7LacLuc, and T7LacILucΔA23 viruses. The samples were harvested and lysed at 24 hours and the proteins resolved on 4-12% NuPAGE gel, blotted, and incubated with rabbit polyclonal LacI Ab, followed by donkey anti-rabbit 800CW secondary antibody and analyzed by LI-COR. As predicted, Lac repressor is only expressed in complementing RK/A8A23 cells by T7LacILuc A23, (blue arrows indicate T7LacILucΔA23 samples).

Example 6

Figure 6:
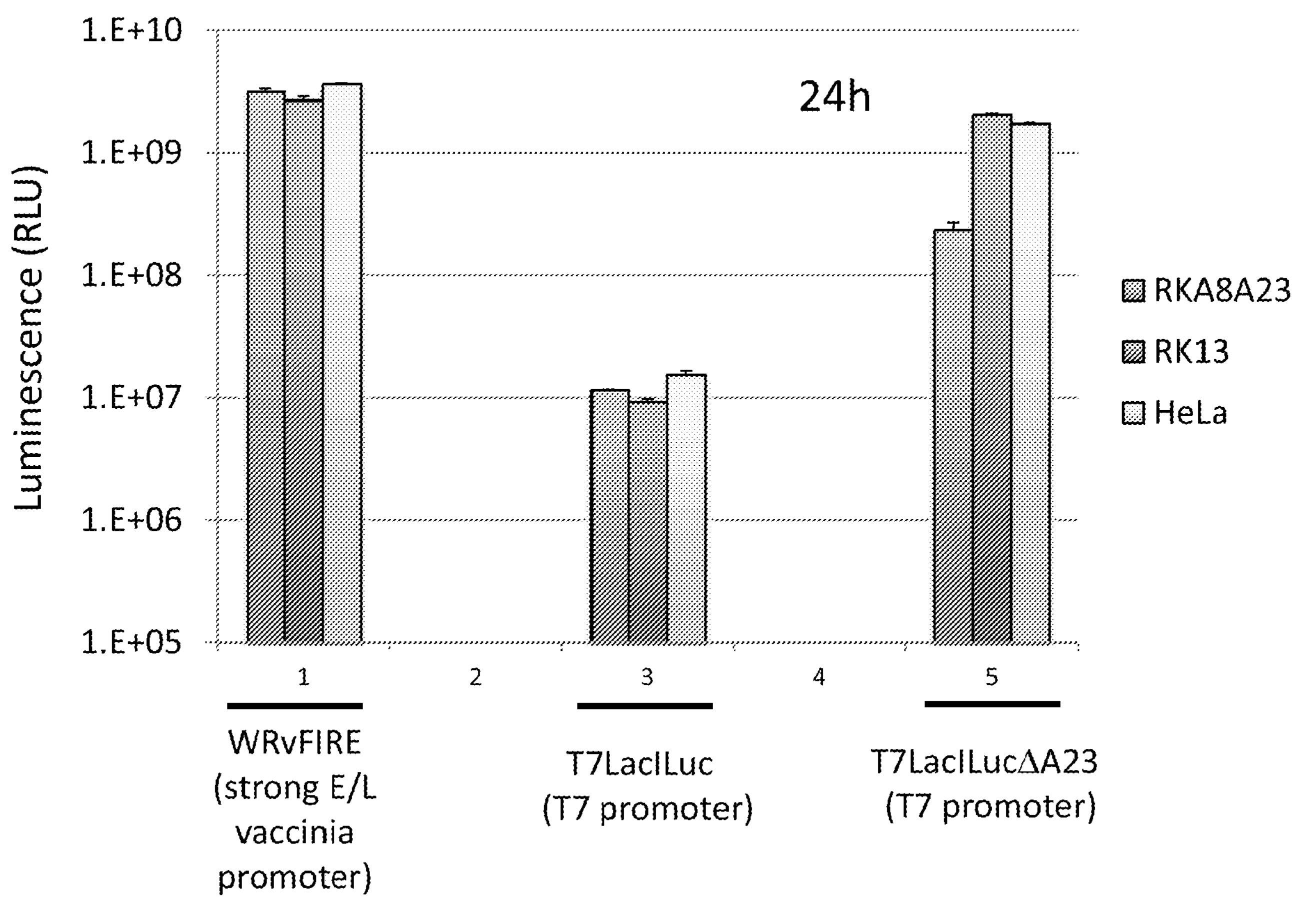
FIG. 6 shows a comparison of replication competent (WRvFIRE and T7LacILuc) and defective (T7LacILucDA23) vaccinia on luciferase expression in complementing and non-complementing cells.

This example demonstrates a comparison of replication competent and defective vaccinia on firefly luciferase expression in complementing and non-complementing cells. Triplicate samples of virus-infected (MOI=5) RK/A8A23, RK13, and HeLa cells, were harvested at 24 hours and analyzed using the Luciferase Assay System (PROMEGA™). FIG. 6 shows that replication competent WRvFire expressed luciferase at high levels in all cells; T7LacILuc expressed at low levels in all cells because of continuous synthesis of Lac repressor. T7LacILucΔA23 expressed luciferase at 10-fold lower level in RK/A8A23 cells than RK13 and HeLa cells, because the Lac repressor, regulated by an intermediate promoter, was made only in RK/A8A23 cells. T7LacILucΔA23 expressed luciferase at high levels in the non-complementing cells.

Example 7

Figure 7A:
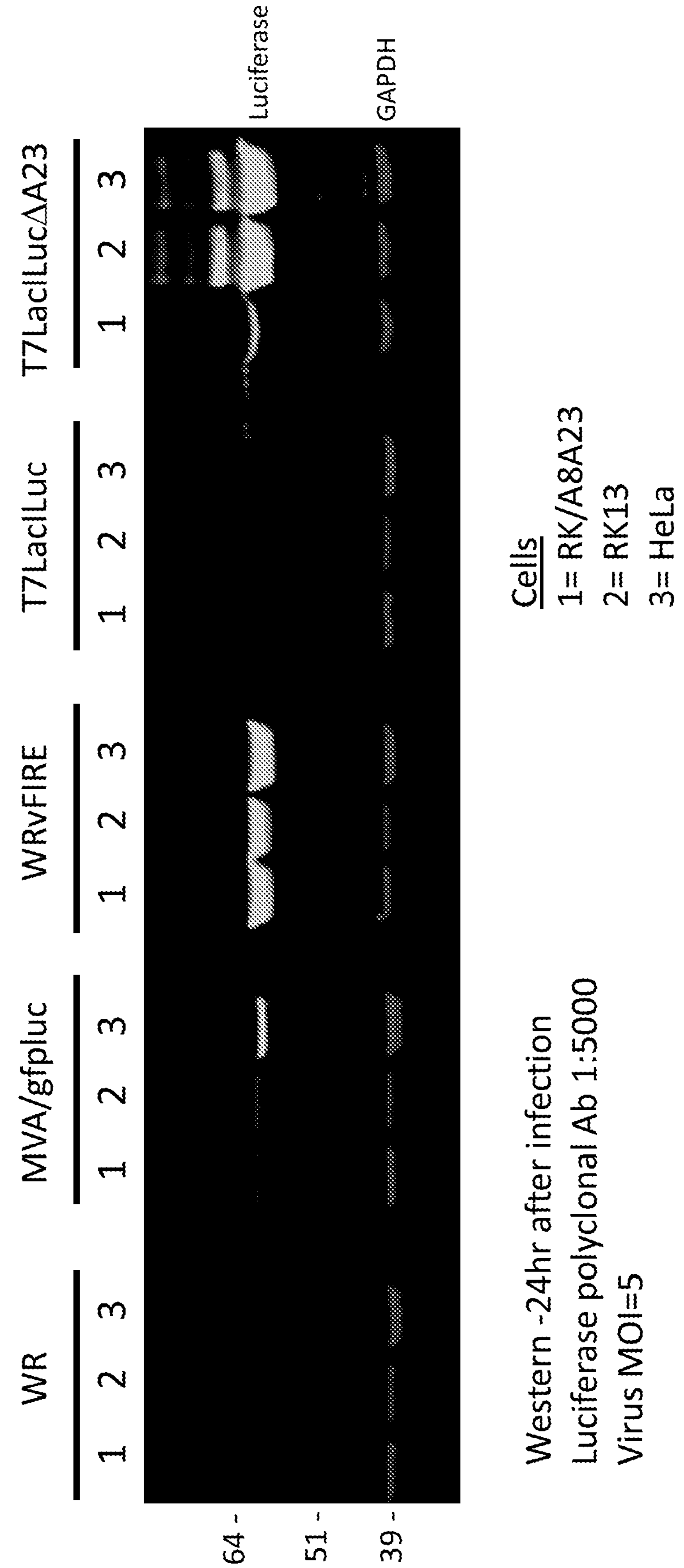
FIG. 7A shows a Western blot comparison of replication competent (WRvFire and T7LacILuc) and defective (T7LacILucDA23 and MVAgfpluc) vaccinia viruses on luciferase expression in RK/A8A23, RK13 and HeLa cells.

For further comparison of replication competent and defective vaccinia on luciferase expression in complementing and non-complementing cells, three cell lines were infected with five different viruses (MOI=5) and luciferase protein was detected with polyclonal luciferase Ab by Western blotting at 24 hours. As shown in FIG. 7A, the new vector, T7LacILucΔA23, expressed luciferase at low levels in RK/A8A23 cells and at high levels in non-complementing RK13 and HeLa cells.

Figure 7B:
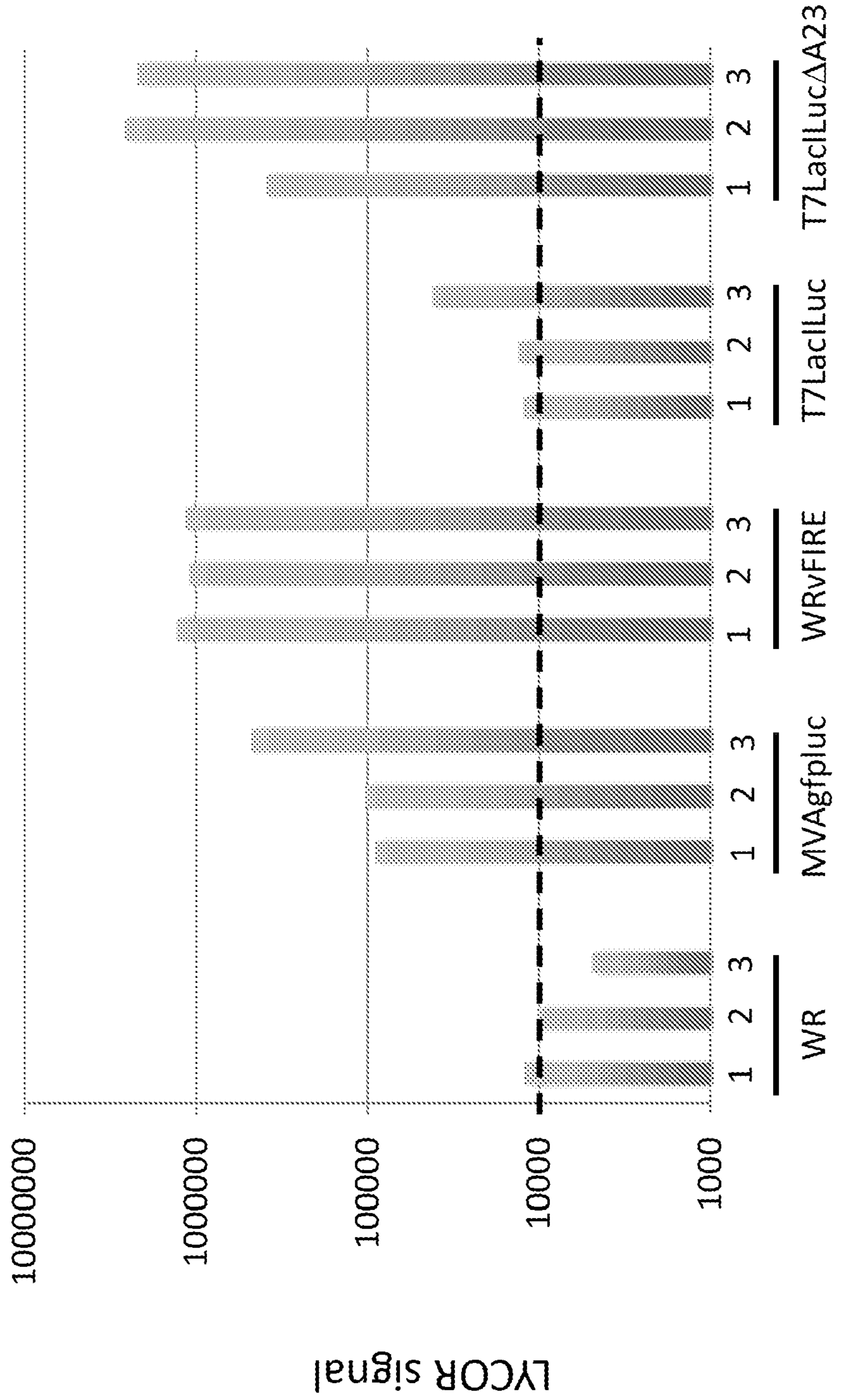
FIG. 7B shows a LICOR quantitation of the luciferase bands from the Western blot shown in FIG. 7A. For each vaccinia virus, 1 indicates luciferase expression in RK/A8A23 cells, 2 indicates luciferase expression in RK13 cells, and 3 luciferase expression in HeLa cells. Values above the dotted line are above background.

As shown in FIG. 7B, LI-COR quantitation of the Western luciferase bands shown in FIG. 7B demonstrated 1.8-2.3 fold more luciferase protein detected in cells infected with the new vector than in replication competent WRvFIRE. T7LacILucΔA23 has much higher expression than the replication defective MVA vector, which is even lower than replication competent WRvFIRE. The Western blot results fully confirm the luciferase assay data and demonstrate the advantage of this viral expression system.

Example 8

Figure 8:
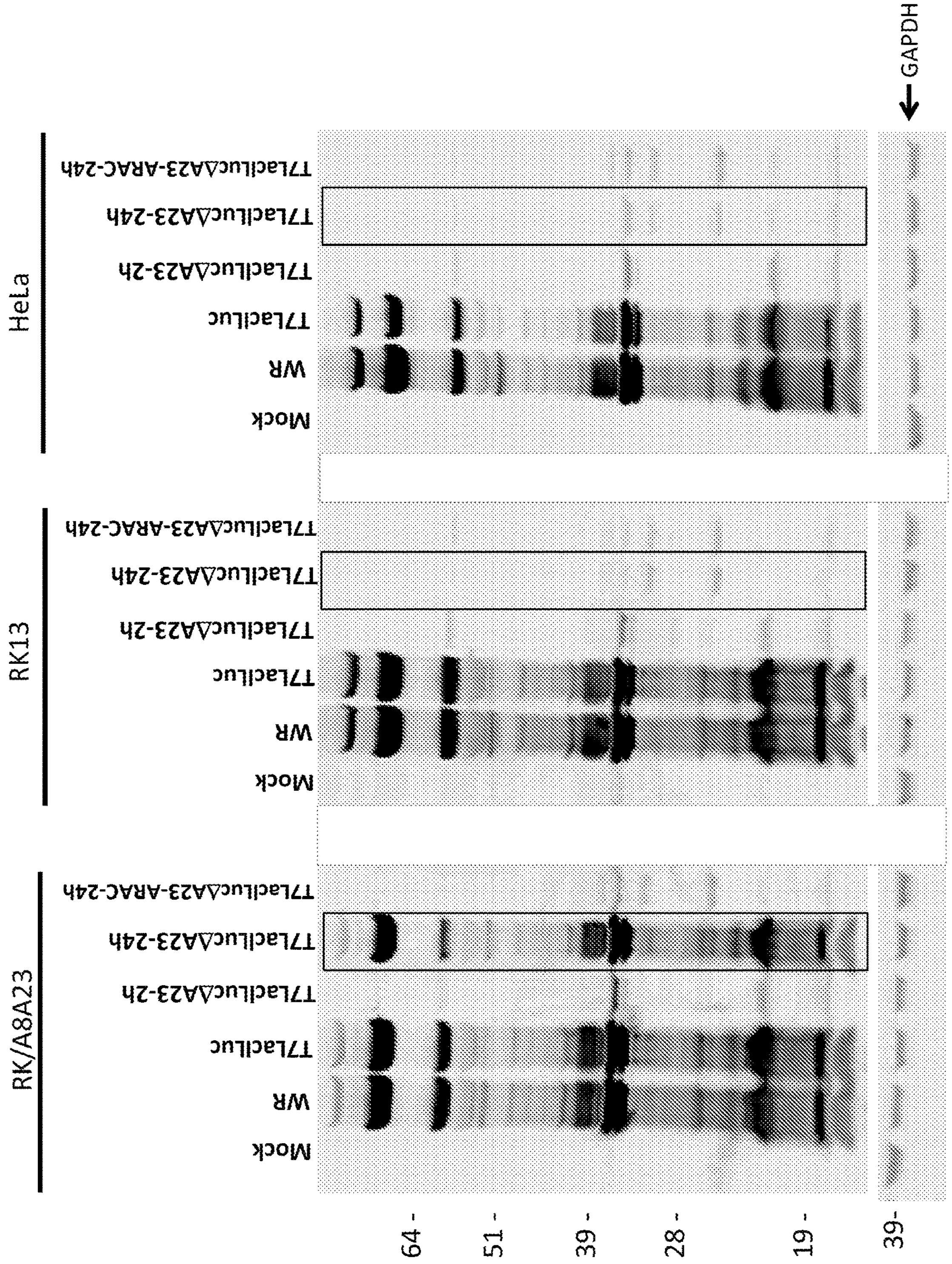
FIG. 8 shows a Western blot analysis indicating vaccinia gene expression from the prototype T7LacILucΔA23 and control viruses in RK/A8A23, RK13, and HeLa cells. Protein was detected by rabbit polyclonal anti-vaccinia antibodies.

This example demonstrates the vaccinia gene expression measured in the prototype T7LacILucΔA23 and control viruses in RK/A8A23, RK13, and HeLa cells. Three cell lines were infected at an MOI of 5 with T7LacILacΔA23 and the control viruses and lysed at 24 hr. The proteins were resolved on 4-12% NuPAGE gel, blotted, and incubated with anti-vaccinia rabbit serum. As shown in FIG. 8, T7LacILucΔA23 had diminished viral protein synthesis (only early gene expression pattern in 24 hour samples) in non-complementing RK13 and HeLa cells (note blue boxes) because of absence of the A23 intermediate transcription factor.

Cumulatively, these data demonstrate that the vector system of the present disclosure replicates only in complementing cell lines, expresses the target gene (luciferase) at high levels in non-complementing cell lines, expresses the target gene (luciferase) at low levels in complementing cell lines, and has diminished vaccinia protein synthesis in non-complementing cell lines.

Example 9

Figure 9:
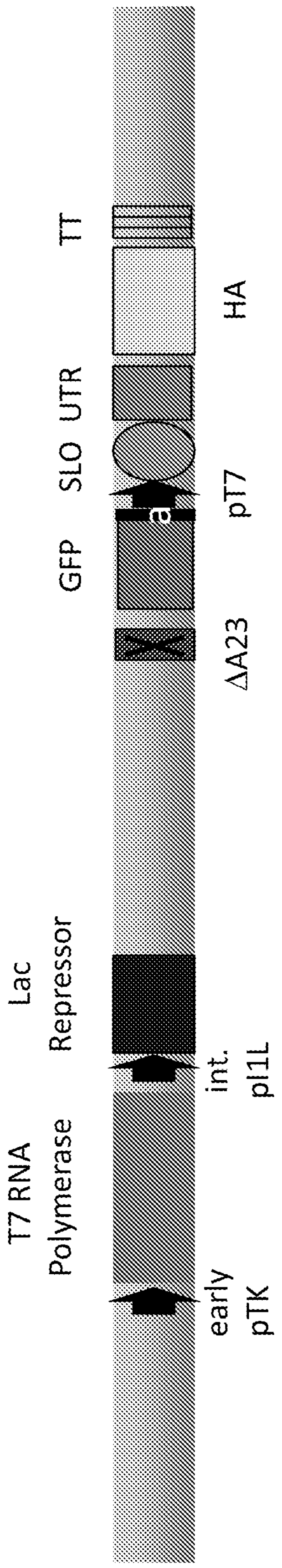
FIG. 9 depicts the T7 recombinant virus construct that expresses influenza hemagglutinin, used for immunization and protection studies in mice. In this construct (T7/HA) hemagglutinin in the A56 gene of WR is controlled by the T7 promotor.
Figure 18:
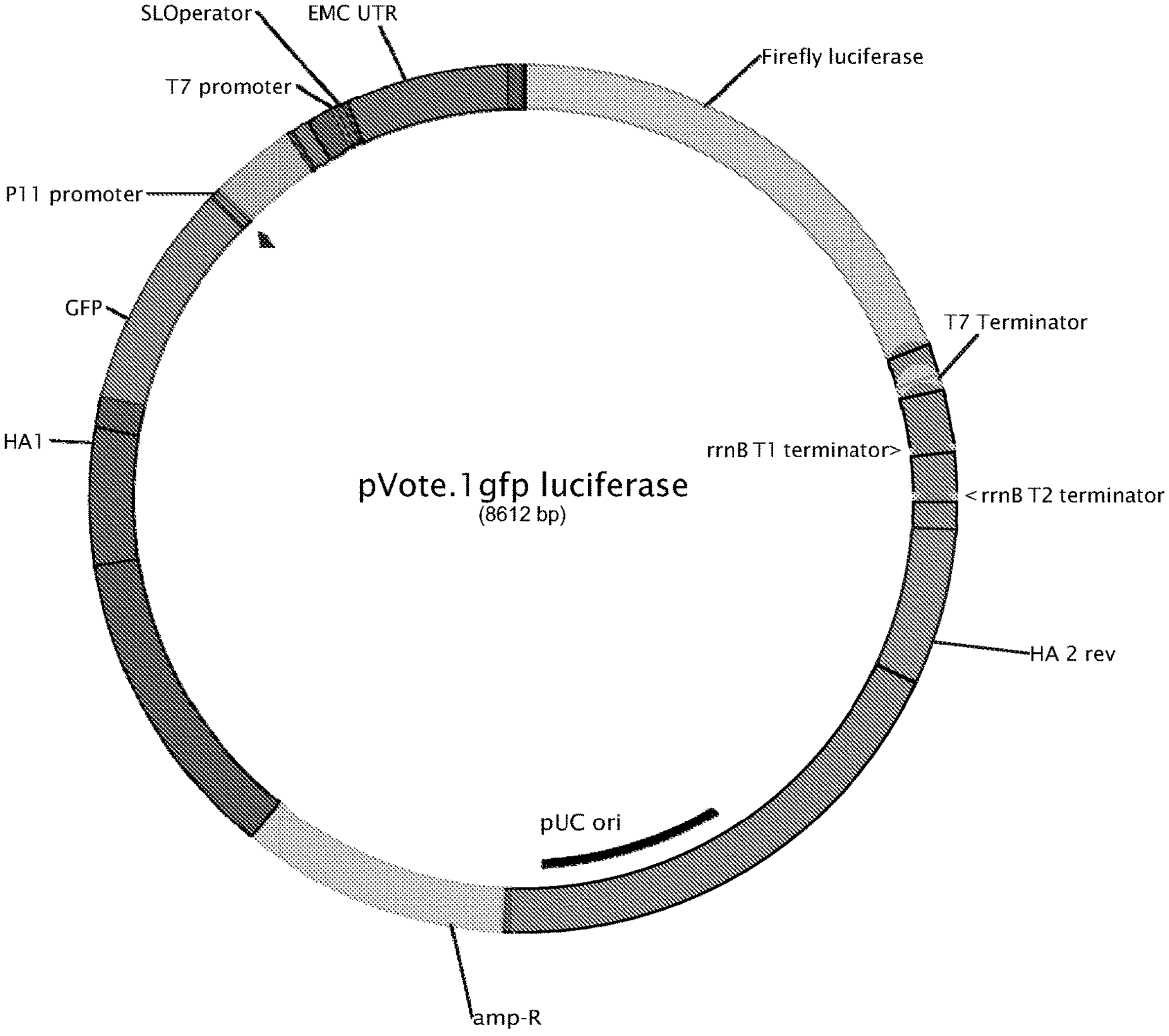
FIG. 18 depicts a viral vector construct map of a viral vector (pVote.1gfp luciferase) of this disclosure.
Figure 19:
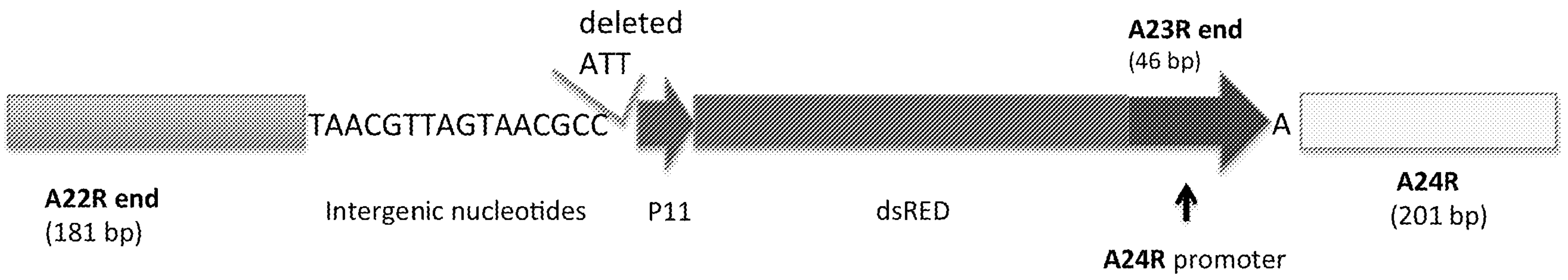
FIG. 19 depicts the PCR product construct used to insert the P11 promoter and knoch out the A23 gene in creating viral vector constructs of this disclosure.
Figure 20:
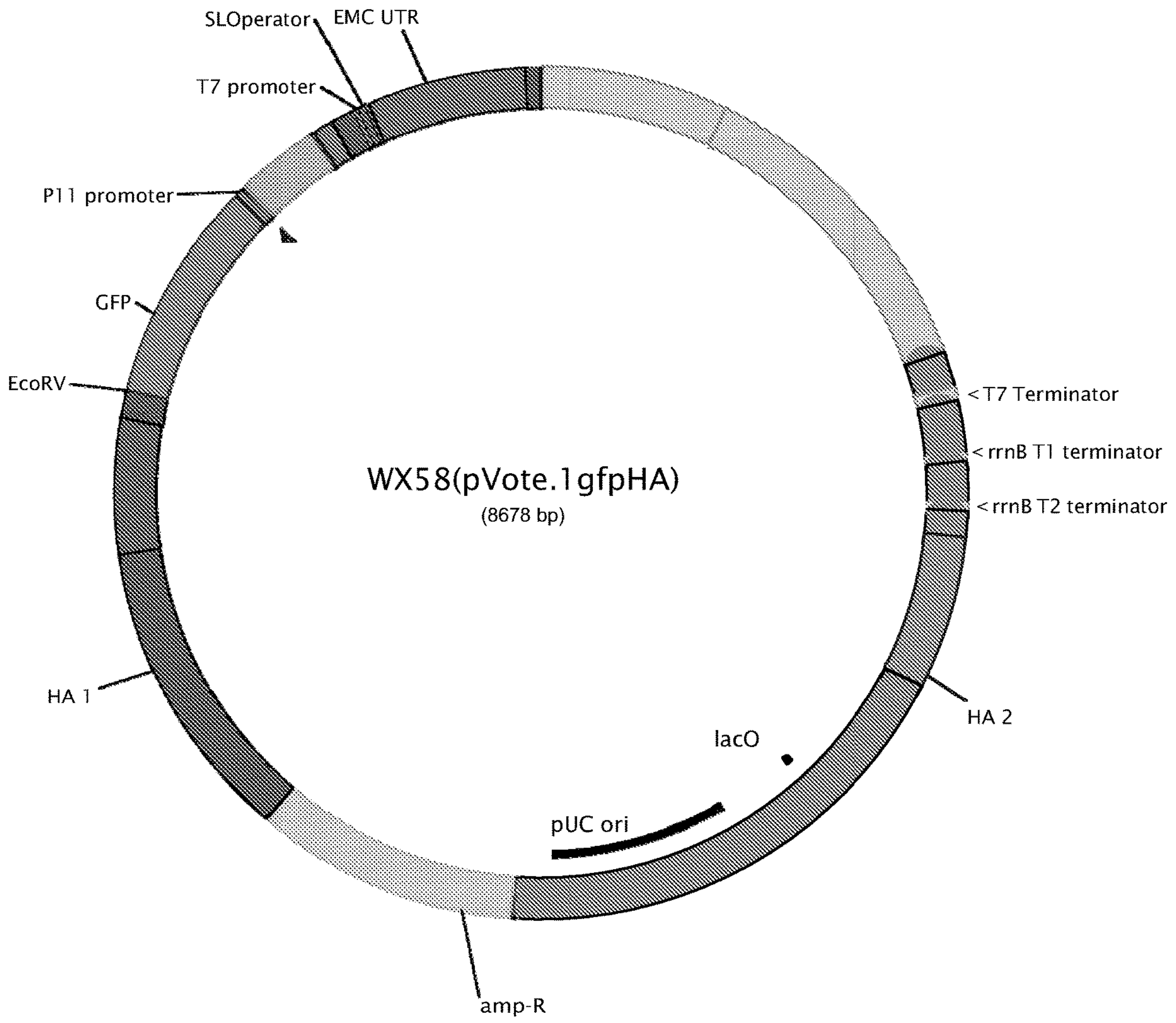
FIG. 20 depicts a viral vector construct map of a viral vector (WX58(pVote.1gfpHA)) of this disclosure.
Figure 21:
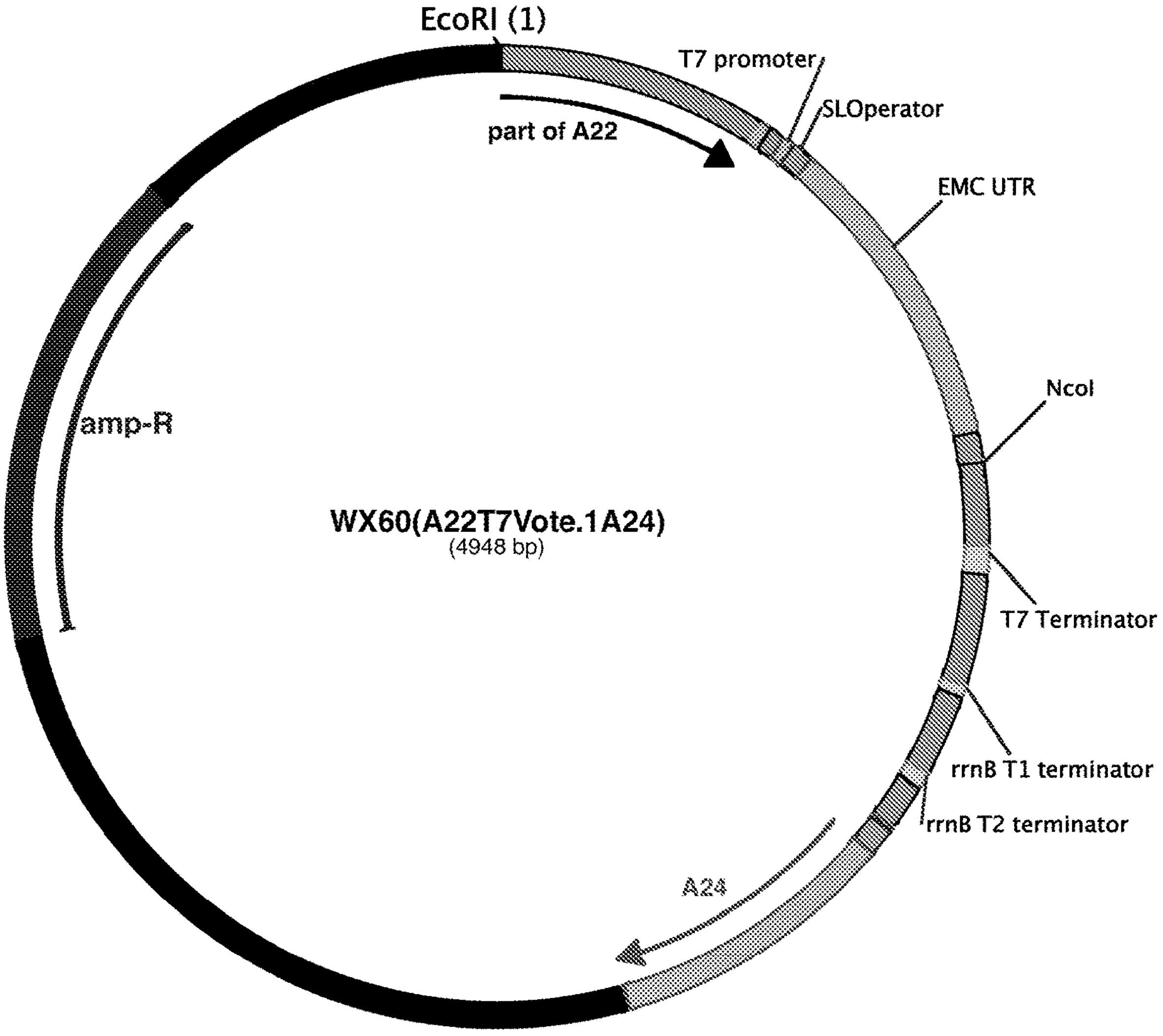
FIG. 21 depicts a viral vector construct map of a viral vector (WX60(A22T7Vote.1A24)) of this disclosure.
Figure 22:
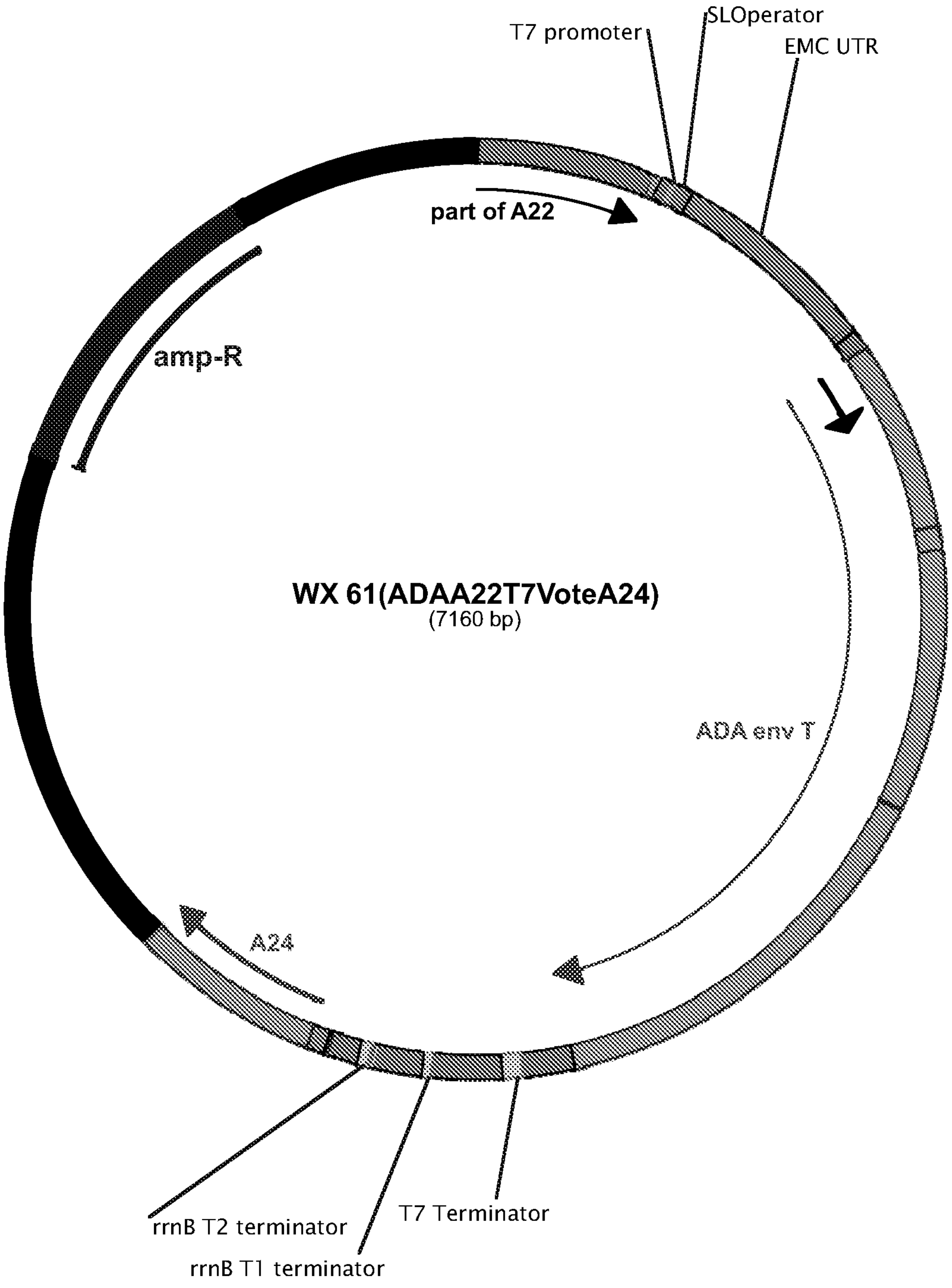
FIG. 22 depicts a viral vector construct map of a viral vector (WX 61(ADAA22T7VoteA24)) of this disclosure.

FIG. 9 depicts the construction of T7/HA (also called T7LacIDA23/HA) construct of this disclosure. The hemagglutinin (HA) gene of influenza A PR8 was inserted into the plasmid T7/cassette (pVote1gfp; for map see FIG. 18). This was inserted into A56 region of T7LacIDA23 (WR virus containing the T7 RNA polymerase and Lac repressor under the control of early and intermediate promoters, respectively with the vaccinia A23 intermediate transcription factor gene knocked out). The recombinant virus was purified by successive plaque purification using GFP screening. The recombinant viral construct produced was T7LacIDA23/HA (FIG. 9), but for simplicity sake, called "T7/HA." In the mouse experiments, the T7/HA and recombinant MVA/HA, made with the same HA gene and called "MVA/HA," were used.

To demonstrate the expression specificity, three cell lines (RK/A8A23 helper, RK13, and HeLa cells) were infected at an MOI=3 pfu/well with each virus. Infected cells were harvested and lysed at 24 hours, and the proteins were resolved by electrophoresis on 4-12% NuPAGE Bis-Tris gel (FIG. 10). Proteins were transferred to nitrocellulose membrane with an iBlot system, blocked in 5% nonfat milk in PBS with 0.05% Tween 20, and incubated with HA mouse MAb H28E23 antibodies, followed by anti-mouse secondary antibodies conjugated to IRDye 800CW green and visualized using a LI-COR Odyssey infrared imager. Loading control actin was visualized in the same way using anti-actin rabbit antibodies followed by secondary anti-mouse IRDye 680 red.

Stability testing of the T7/HA viral construct was tested at the last plaque purification of T7/HA, six plaques and passaged independently in complementing RK/A8A23 for 10 passages. At passage 1, 5, and 10, stability of the HA gene in the recombinant virus was assessed by immunostaining with influenza HA (H28E23) MAb, followed by peroxidase-conjugated anti-mouse IgG, and peroxidase substrate. Both titer and percentage of non-staining plaques of each passaged plaque were assessed. The stability data confirmed that T7/HA has very little hemagglutinin instability through 10 passages.

Example 10

Figure 11:
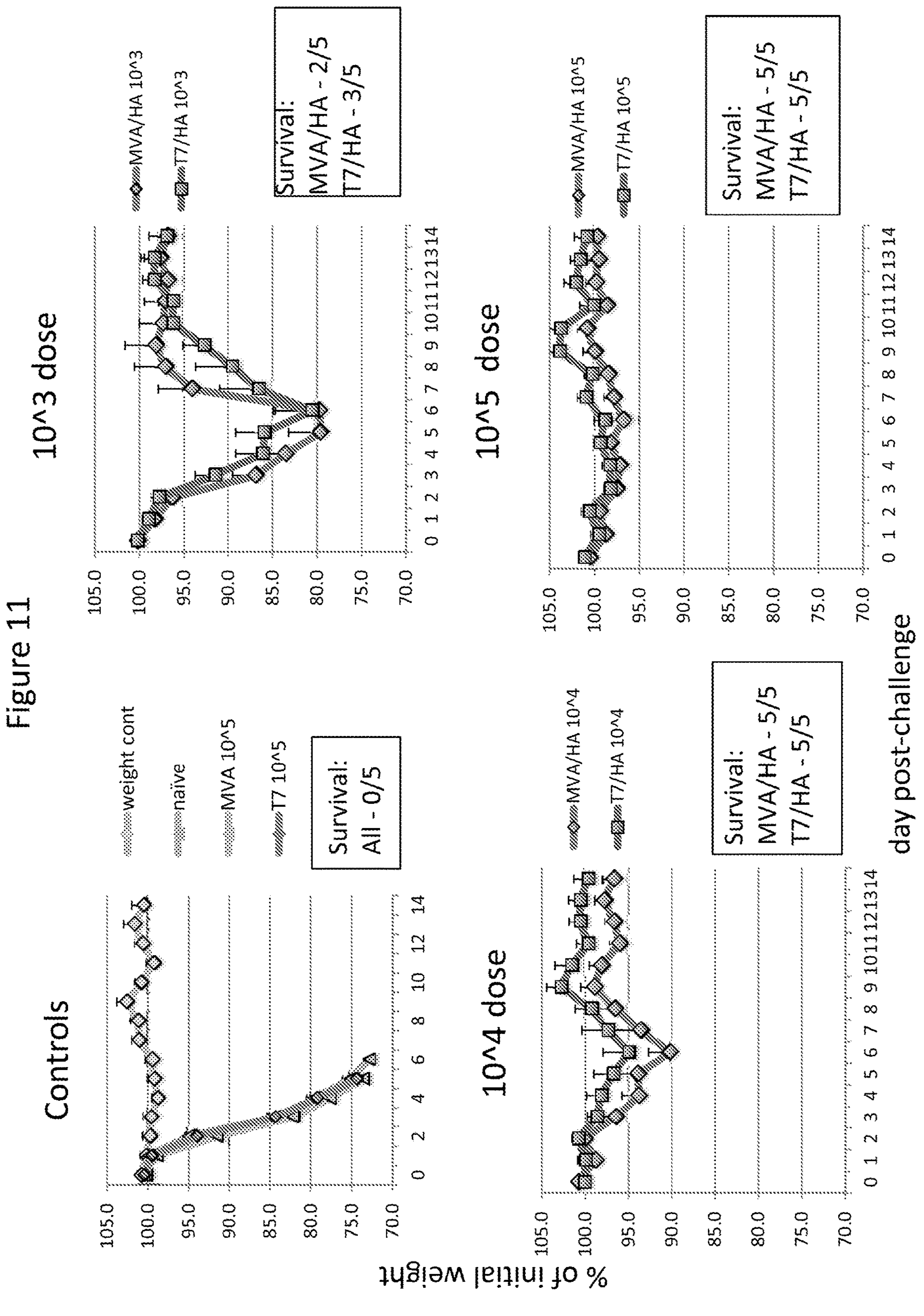
FIG. 11 shows the weight loss and survival after influenza A challenge following a one-time immunization of mice (n=5 animals, each group) with the T7/HA construct of this disclosure.

This example demonstrates animal studies with the T7/HA construct of this disclosure to assess weight loss and survival after Influenza A challenge following a single immunization with the T7/HA construct. Seven week old BALB/c mice (5 in each group) were immunized with $10^5$, $10^4$, or $10^3$ pfu of T7/HA recombinant virus intramuscularly. At 3 weeks post-infection, serum samples were obtained for antibody studies. At 4 weeks post-infection mice were challenged with $100_{LD50}$ of influenza A PR8 (dose previously determined). Animals were weighed daily to determine weight loss. Survival of mice in each group included those found dead or humanely euthanized if weight fell below 70% of initial weight. Weight loss and survival data are shown in FIG. 11.

Figure 12:
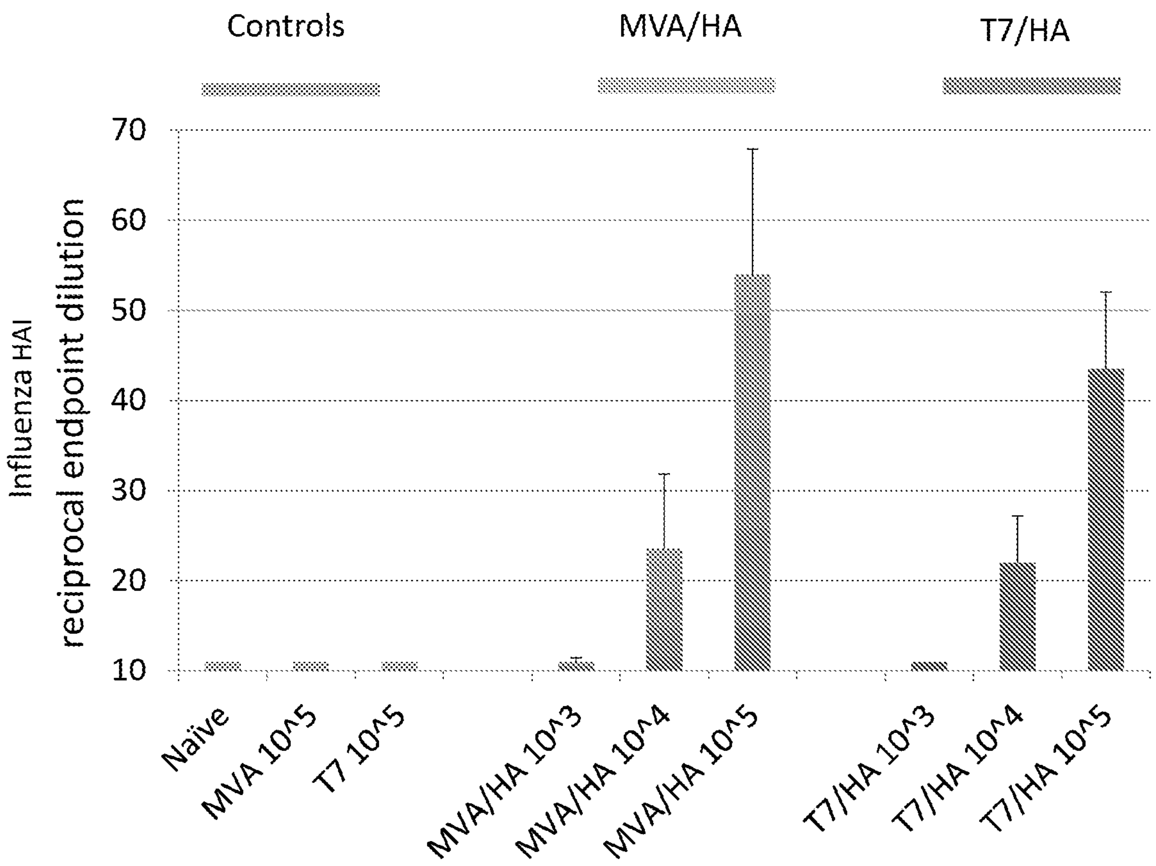
FIG. 12 shows the titers of influenza hemagglutinin-inhibiting antibodies produced in the mice administered the one-time immunization of the T7/HA construct.

Titers of Influenza hemagglutination-inhibiting antibodies were tested in these immunized animals. Nonspecific inhibitors of hemagglutination-inhibition were first removed by preincubation of serum from the test animals with Chlorea filtrate for 20 hours at 37° C., and inactivation of serum at 56° C. Using 96 V well plates, two-fold dilutions of individual serum samples were made in PBS. Eight HA units of influenza A PR8 were added in equal volume to serum dilutions and allowed to incubate for 30-45 minutes, followed by addition of 1% turkey red blood cells in PBS. At 30 minutes post-addition of RBCs, agglutination of RBCs were read. Titers were plotted as reciprocal serum dilution of complete hemagglutination-inhibition endpoint (FIG. 12). These data demonstrate that T7/HA makes HA antibodies as measured by the HAI test.

Example 11

Figure 13:
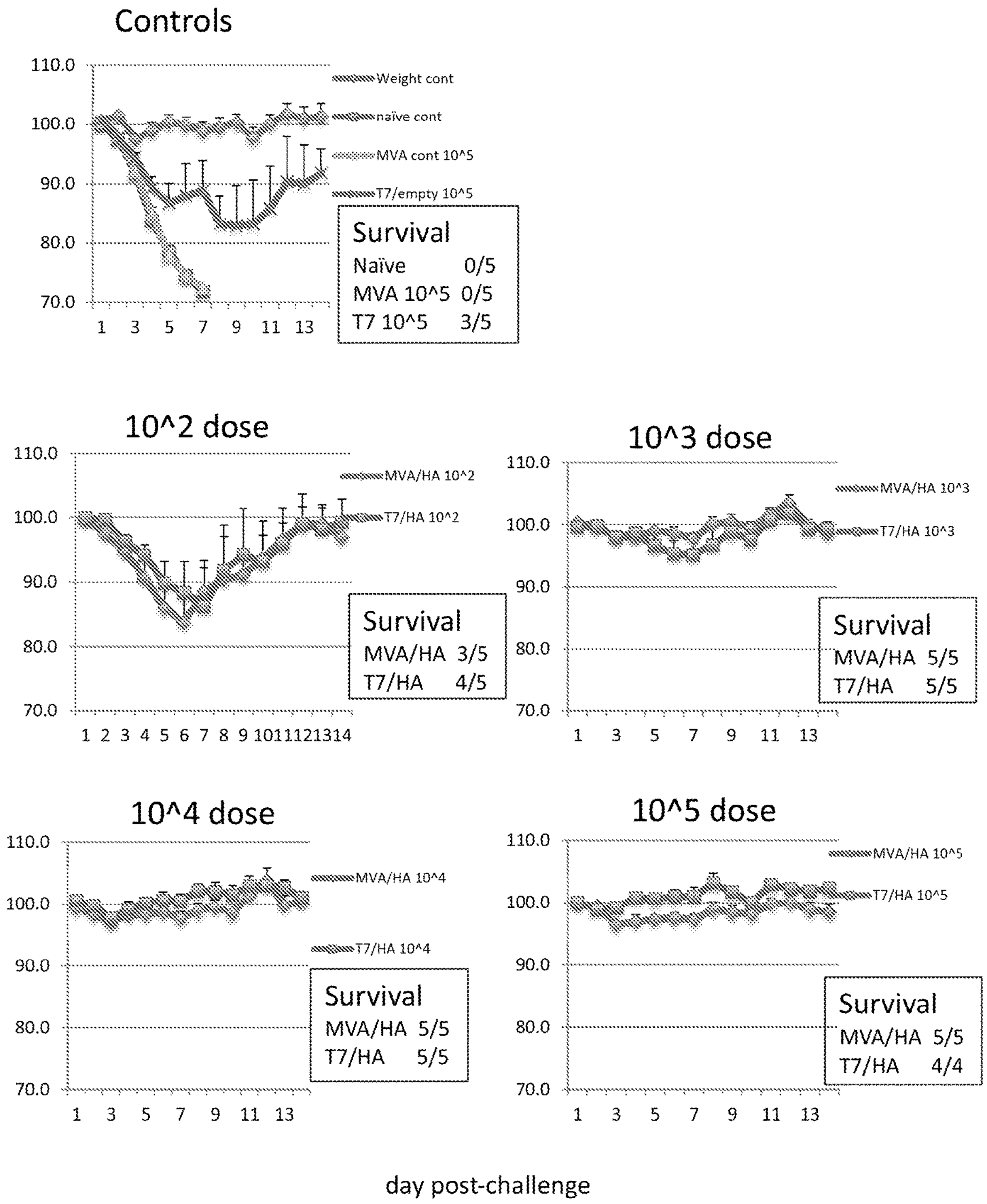
FIG. 13 shows the weight loss and survival after influenza A challenge following a two-time immunization of mice (n=5 animals, each group) with the T7/HA construct of this disclosure at four doses.

This Example demonstrates animal testing following twice-immunization with the T7/HA construct. For weight loss and survival after influenza A challenge, seven week old BALB/c mice (5 in each group) were immunized with $10^5$, $10^4$, $10^3$ or $10^2$ pfu of T7/HA viral construct. At 3 weeks, the mice were bled for antibody studies. At 4 weeks, the mice were given a second immunization of virus, and 3 weeks later, the mice were challenged with $100_{LD50}$ of influenza A PR8 (dose previously determined). Animals were weighed daily to determine weight loss. Mice in each group that did not survive included those found dead or humanely euthanized if weight fell below 70% of initial weight. Weight loss and survival data are shown in FIG. 13.

Figure 14A:
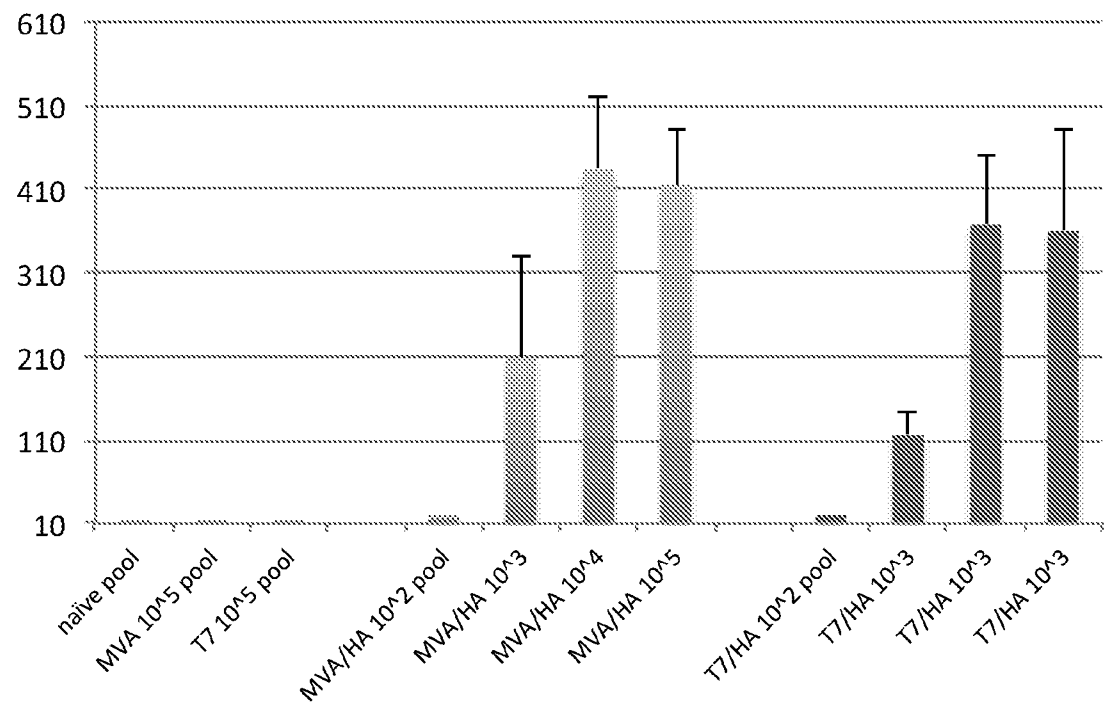
FIG. 14A Influenza HAI response of 2× immunization with T7/HA in mice

Influenza HAI and ELISA response testing was conducted on the serum of the mice twice-immunized with the T7/HA construct. For the Influenza Hemagglutination-Inhibition antibody testing (Influenza HAI), nonspecific inhibitors of hemagglutination-inhibition were removed by preincubation of sera with Chlorea filtrate for 20 hours at 37° C., and inactivation of serum at 56° C. Using 96 V well plates, two-fold dilutions of individual serum samples (except where noted in legend) were made in PBS. Eight HA units of influenza A PR8 were added in equal volume to serum dilutions and allowed to incubate for 30-45 minutes, followed by addition of 1% turkey red blood cells in PBS. At 30 minutes post-addition of RBCs, agglutination of RBCs were read. FIG. 14A shows the titers plotted as the reciprocal serum dilution of complete hemagglutination-inhibition endpoint.

Figure 14B:
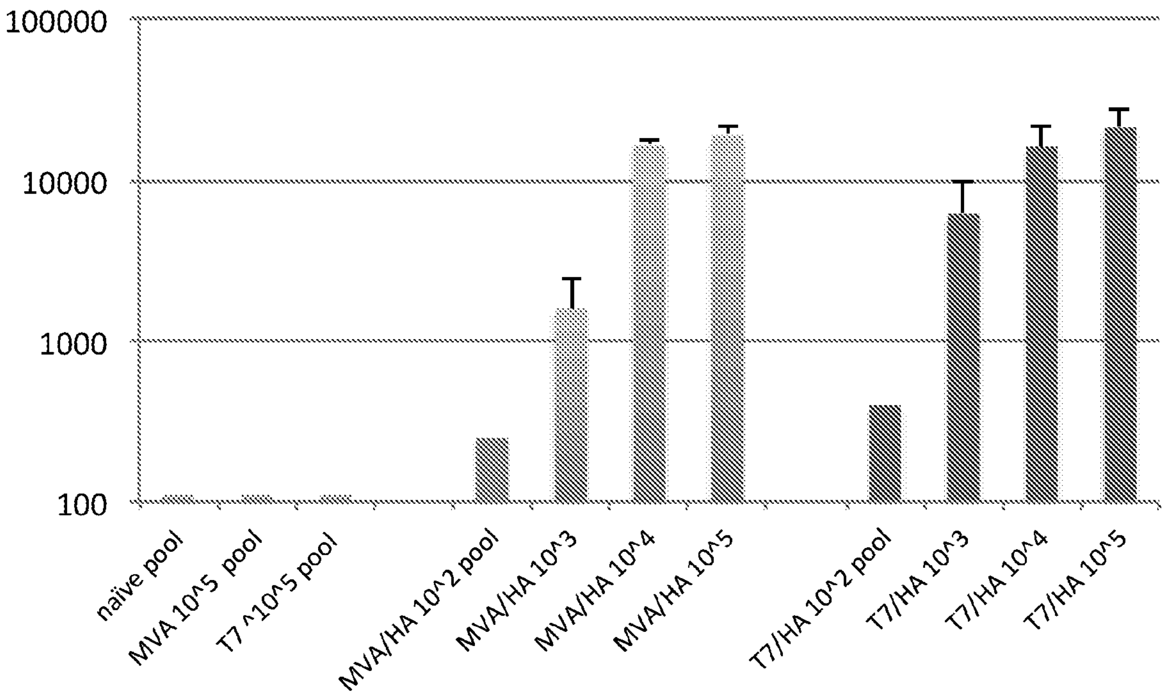
FIG. 14B ELISA response of 2× immunization with T7/HA in mice

For the Influenza HA ELISA, 96-well plates were coated with Influenza A PR8, incubated at 4° C. overnight, and inactivated with 2% formaldehyde. Two fold serum dilutions were made on the antigen coated plates, incubated for 1 hour, followed by addition of peroxidase-conjugated anti-mouse IgG. Substrate was added and samples were read at wavelengths 370 and 492 nm with background subtracted from each well. Readings greater than 0.1 were considered endpoint, and graphed as reciprocal endpoint dilutions (FIG. 14B).

Example 12

Figure 15:
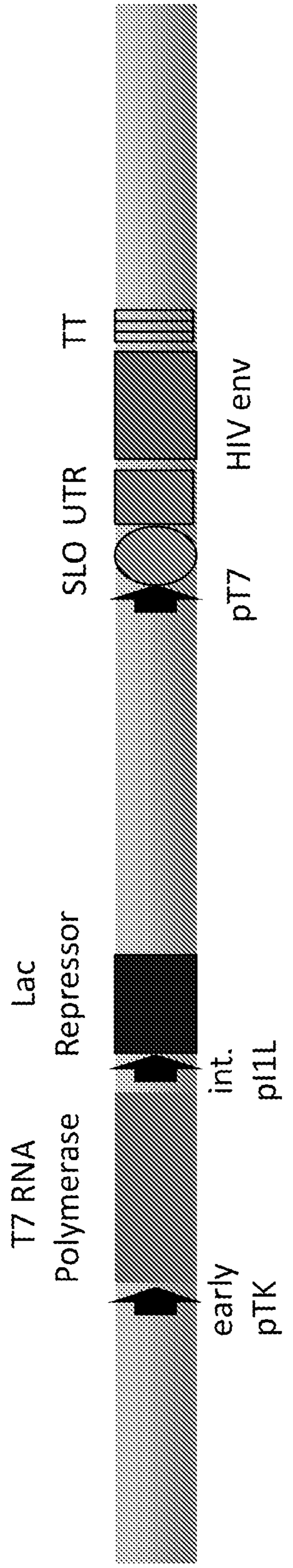
FIG. 15 depicts the T7 recombinant virus construct of this disclosure that expresses HIV Clade B envelope.

The Example demonstrates the construction of the new T7 Recombinant Virus expressing HIV Clade B envelope. To build the T7/HIVenv construct (depicted in FIG. 15), HIV Clade B ADA truncated envelope was cloned into a new T7 cassette vector (pWX60) containing the T7 promoter (pT7), operator (SLO), untranslated region (UTR) of EMC virus, as well as the triple terminator (TT) called pWX61. Plasmid WX61 containing HIV env gene controlled by T7 promoter was cloned into recombinant T7LacIDA23 virus between the A22 gene and A24 gene using live immunostaining of HIV env protein (T-43MAb) (for selection of recombinant expressing HIV env). This viral construct was called "T7LacIDA23/HIVenv(WX61)," or for simplicity, "T7/HIVenv."

Figure 16:
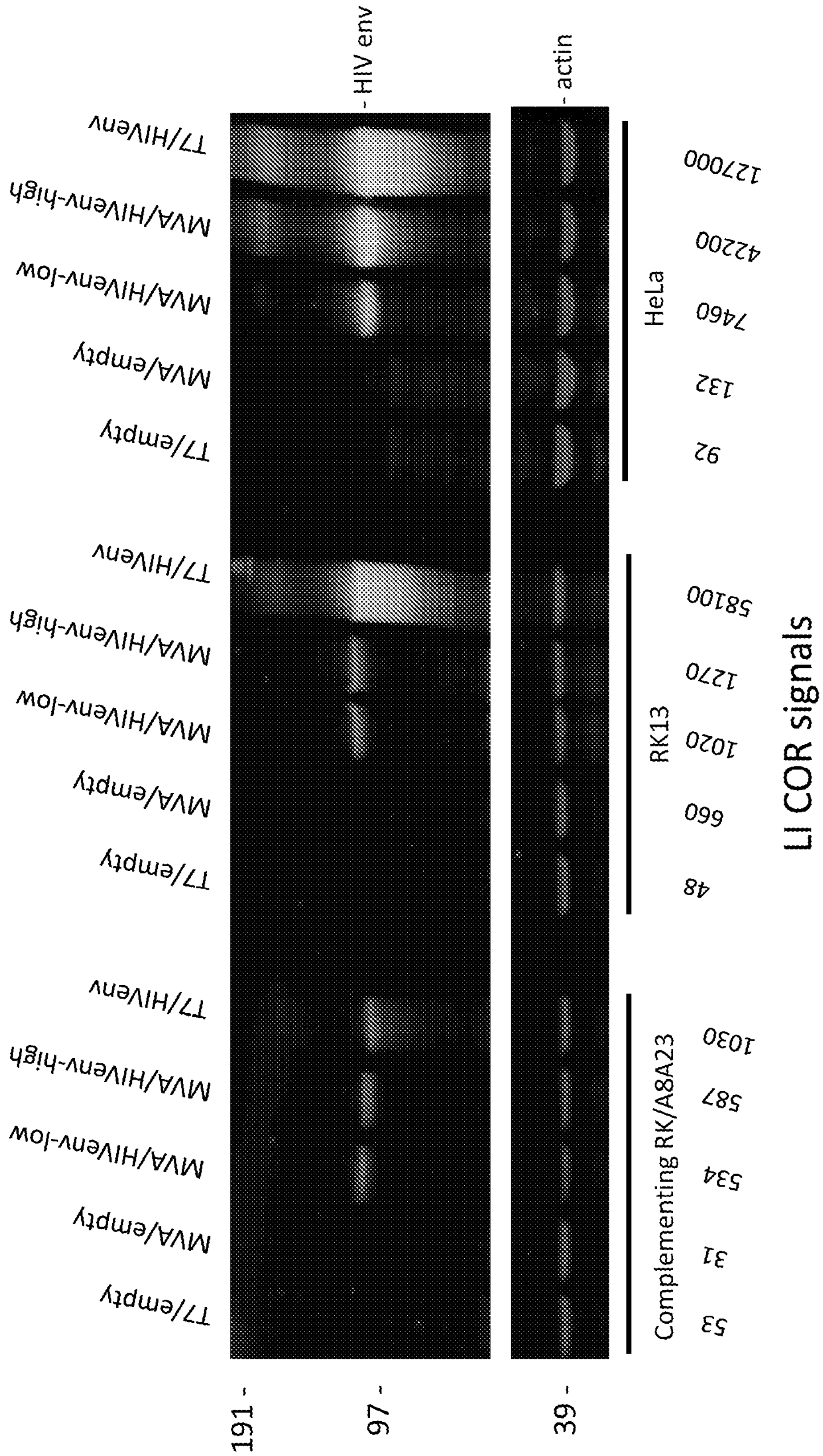
FIG. 16 is a Western blot, and LICOR quantitation of protein bands, of T7/HIVenv expression from the construct depicted in FIG. 16 in three cell lines.

HIV envelope expression from the T7/HIVenv construct was tested by Western blotting. Three cell lines (RK/A8A23 helper, RK13, and HeLa cells) were infected at an MOI=3 pfu/well with each virus. Infected cells were harvested and lysed at 24 hours, and the proteins were resolved by electrophoresis on 4-12% NuPAGE Bis-Tris gel. Proteins were transferred to nitrocellulose membrane with an iBlot system, blocked in 5% nonfat milk in PBS with 0.05% Tween 20, and incubated with T32 mouse MAb, followed by anti-mouse secondary antibodies conjugated to IRDye 800CW green and visualized using a LI-COR Odyssey infrared imager (FIG. 16). Loading control actin was visualized in same way as above with anti-actin rabbit antibodies followed by secondary anti-mouse IRDye 680 red.

The foregoing examples of this disclosure have been presented for purposes of illustration and description. These examples are not intended to limit this disclosure to the form disclosed herein. Consequently, variations and modifications commensurate with the teachings of the description of this disclosure, and the skill or knowledge of the relevant art, are within the scope of this disclosure. The specific embodiments described in the examples provided herein are intended to further explain the best mode known for practicing these embodiments and to enable others skilled in the art to utilize these embodiments in such, or other, embodiments and with various modifications required by the particular applications or uses of this disclosure. It is intended that the appended claims be construed to include alternative embodiments to the extent permitted by the prior art.

What is claimed is:

1. A recombinant chordopoxvirus comprising:

a) a first nucleic acid sequence encoding a heterologous DNA-dependent RNA polymerase, wherein the first nucleic acid sequence is functionally linked to a chordopoxvirus pre-replicative promoter;

b) a second nucleic acid sequence encoding a heterologous repressor protein, wherein the second nucleic acid sequence is functionally linked to a chordopoxvirus post-replicative promoter; and, c) at least one inactivating mutation in an open reading frame (ORF) required for the expression of post-replicative genes;

wherein the recombinant chordopoxvirus is capable of replicating its genome.

2. The recombinant chordopoxvirus of claim 1, wherein the pre-replicative promoter is a chordopoxvirus early promoter.

3. The recombinant chordopoxvirus of claim 2, wherein the pre-replicative promoter is from a chordopoxvirus ORF that corresponds to a vaccinia virus ORF selected from the group consisting of vaccinia Western Reserve (VACWR) 001/218, VACWR002/217, VACWR002/217, VACWR009/210, VACWR010/209, VACWR011/208, VACWR012/207, VACWR013, VACWR018, VACWR019, VACWR021, VACWR022, VACWR023, VACWR024, VACWR029, VACWR031, VACWR032, VACWR034, VACWR037, VACWR038, VACWR039, VACWR046, VACWR047, VACWR050, VACWR051, VACWR053, VACWR054, VACWR055, VACWR057, VACWR059, VACWR060, VACWR061, VACWR065, VACWR068, VACWR072, VACWR073, VACWR080, VACWR082, VACWR083, VACWR089, VACWR094, VACWR098, VACWR101, VACWR103, VACWR106, VACWR109, VACWR112, VACWR114, VACWR117, VACWR123, VACWR124, VACWR127, VACWR138, VACWR141, VACWR143, VACWR152, VACWR154, VACWR156, VACWR158, VACWR160, VACWR165, VACWR166, VACWR169, VACWR170, VACWR172, VACWR173, VACWR174, VACWR176, VACWR178, VACWR180, VACWR181, VACWR181.5, VACWR183, VACWR184, VACWR187, VACWR188, VACWR190, VACWR193, VACWR194, VACWR195, VACWR198, VACWR200, VACWR201, VACWR205, Vaccinia Copenhagen (VC) C23L, VC VACWR002/217 pseudogene, VC C11R, VC C10L, VC C9l, VC C8L, VC C7L, VC C6L, VC C5L, VC C4L, VC N2L, VC M2L, VC K1l, VC K3L, VC K5L, VC K6L, VC K7R, VC F7L, VC F8L, VC F11L, VC F12L, VC F14L, VC F15L, VC F16L, VC E1L, VC E3L, VC E4L, VC E5R, VC E9L, VC O1L, VC I3L, VC I4L, VC G2R, VC G5R, VC G5.5R, VC L2R, VC J2R, VC J6R, VC H3L, VC H5R, VC D1R, VC D4R, VC D7R, VC D9R, VC D12L, VC A4L, VC A5R, VC A8R, VC A18R, VC A20R, VC A23R, VC A29L, VC A31R, VC A33R, VC A35R, VC A37R, VC A40R, VC A41L, VC 268, VC A44L, VC A46R, VC A47L, VC A48R, VC A50R, VC A52R, VC A55R, VC A56R, VC B1R, VC B2R, VC B5R, VC B6R, VC B8R, VC B11R, VC B12R, VC B13R, VC B17L, VC B19, VC VACWR201 Pseudogene, and VC C12L.

4. The recombinant chordopoxvirus of claim 2, wherein the pre-replicative promoter is from a chordopoxvirus ORF that correspondents to the vaccinia virus thymidine kinase ORF (VACVWR094).

5. The recombinant chordopoxvirus of claim 1, wherein the post-replicative promoter is a chordopoxvirus intermediate or late promoter.

6. The recombinant chordopoxvirus of claim 5, wherein the post-replicative promoter is from a chordopoxvirus ORF that corresponds to a vaccinia virus ORF selected from the group consisting of vaccinia Western Reserve (VACWR) 033, VACWR035, VACWR052, VACWR067, VACWR069, VACWR069.5, VACWR070, VACWR074, VACWR075, VACWR081, VACWR099, VACWR101, VACWR113, VACWR116, VACWR118, VACWR119, VACWR120, VACWR122, VACWR125, VACWR131, VACWR135, VACWR136, VACWR139, VACWR146, VACWR147, VACWR148, VACWR150, VACWR15, VACWR153.5, VACWR155, VACWR162, VACWR204.5, VACWR062, VACWR063, VACWR064, VACWR077, VACWR086, VACWR091, VACWR093, VACWR105, VACWR111, VACWR115, VACWR142, VACWR157, VACWR164, VACWR167, VACWR168, VACWR179, VACWR186, VACWR191, VACWR192, VACWR197, VACWR206, VACWR008, VACWR020, VACWR025, VACWR048, VACWR049, VACWR071, VACWR076, VACWR078, VACWR079, VACWR085, VACWR090, VACWR097, VACWR102, VACWR107, VACWR121, VACWR126, VACWR128, VACWR129, VACWR132, VACWR133, VACWR134, VACWR137, VACWR140, VACWR149, VACWR151, VACWR056, VACWR066, VACWR084, VACWR087, VACWR088, VACWR09, VACWR100, VACWR104, VACWR108, VACWR130, VACWR163, VACWR171, VACWR189, VACWR145, VACWR207, Vaccinia Copenhagen (VC) K2L, VC K4L, VC F13L, VC E11L, VC O2L, VC O3L, VC I1L, VC I5L, VC I6L, VC G4L, VC H1L, VC H3L, VC D8L, VC D11L, VC D13L, VC A1L, VC A2L, VC A3L, VC A6L, VC A12L, VC A15L, VC A16L, VC A19L, VC A25L, VC A27L, VC A30L, VC A30.5L, VC A32L, VC A38L, VC E6R, VC E7R, VC E8R, VC I8R, VC G8R, VC L4R, VC J1R, VC H7R, VC D6R, VC D10R, VC A22, VC A34R, VC A42R, VC A43R, VC A53R, VC B4R, VC B9R, VC C13L, VC C19L, VC C8L, VC C3L, VC F9L, VC F10L, VC I2L, VC I7L, VC G1L, VC G3L, VC G7L, VC L3L, VC J5L, VC H4L, VC D2L, VC A2.5L, VC A7L, VC A9L, VC A10L, VC A13L, VC A14L, VC A14.5L, VC A17L, VC A21L, VC A26L, VC A28L, VC F17R, VC E10, VC G6R, VC G9R, VC L1R, VC L5R, VC H2R, VC H6R, VC D3R, VC A11L, VC A39R, VC A45R, and VC B7R.

7. The recombinant chordopoxvirus of claim 1, wherein the post-replicative promoter is from a chordopoxvirus ORF that corresponds to the vaccinia virus I1L (VACWR070) ORF.

8. The recombinant viral vector of claim 1, wherein the post-replicative promoter comprises SEQ ID NO: 90.

9. The recombinant viral vector of claim 1, wherein the at least one inactivating mutation is in an ORF encoding a chordopoxvirus transcription factor.

10. The recombinant chordopoxvirus of claim 9, wherein the transcription factor is encoded by an ORF corresponding to vaccinia virus A8R (VACWR127) or A23R (VACWR143).

11. The recombinant chordopoxvirus of claim 1, wherein the heterologous polymerase is a bacteriophage-induced DNA-dependent RNA polymerase.

12. The recombinant chordopoxvirus of claim 1, wherein the heterologous polymerase is a single subunit phage DNA-dependent RNA polymerase.

13. The recombinant chordopoxvirus of claim 1, wherein the heterologous polymerase is the T7 bacteriophage DNA-dependent RNA polymerase.

14. The recombinant chordopoxvirus of claim 1, wherein the heterologous repressor protein is a prokaryotic protein that binds to an operator sequence.

15. The recombinant chordopoxvirus of claim 1, wherein the heterologous repressor protein is Lad protein.

16. The recombinant chordopoxvirus of claim 1, wherein the first nucleic acid sequence is located between two chordopoxvirus ORFs corresponding to vaccinia virus ORFs F12 and F13.

17. The recombinant chordopoxvirus of claim 1, wherein the second nucleic acid sequence is located between two chordopoxvirus ORFs corresponding to vaccinia virus ORFs F12 and F13.

18. The recombinant chordopoxvirus of claim 1, wherein the first and second nucleic acid sequences are located at the same site.

19. The recombinant chordopoxvirus of claim 1, comprising a third nucleic acid sequence that comprises:

i) at least one polynucleotide sequence functionally linked to a promoter recognized by the heterologous DNA-dependent RNA polymerase; and, ii) a binding site for the heterologous repressor protein, positioned such that binding of the heterologous repressor protein to the binding site impedes the heterologous polymerase from transcribing the at least one polynucleotide sequence.

20. The recombinant chordopoxvirus of claim 19, wherein the promoter recognized by the heterologous polymerase is a T7 promoter.

21. The recombinant chordopoxvirus of claim 19, wherein the binding site is a lac operator sequence.

22. The recombinant chordopoxvirus of claim 19, wherein the polynucleotide sequence encodes a therapeutic protein, an immunogenic protein, or a therapeutic RNA.

23. The recombinant chordopoxvirus of claim 22, wherein the immunogenic protein is from a virus selected from the group consisting of adenoviruses, herpesviruses, papilloma viruses, polyomaviruses, hepadnaviruses, parvoviruses, astroviruses, caliciviruses, picornaviruses, coronaviruses, flaviviruses, togaviruses, herpesviruses, retroviruses, orthomyxoviruses, arenaviruses, bunyaviruses, filoviruses, paramyxoviruses, rhabdoviruses, reoviruses, and poxviruses.

24. The recombinant chordopoxvirus of claim 1, wherein the recombinant chordopoxvirus is a recombinant vaccinia virus.

25. The recombinant vaccinia virus of claim 24, wherein the pre-replicative promoter is from a poxvirus ORF selected from the group consisting of vaccinia Western Reserve (VACWR) 001/218, VACWR002/217, VACWR002/217, VACWR009/210, VACWR010/209, VACWR011/208, VACWR012/207, VACWR013, VACWR018, VACWR019, VACWR021, VACWR022, VACWR023, VACWR024, VACWR029, VACWR031, VACWR032, VACWR034, VACWR037, VACWR038, VACWR039, VACWR046, VACWR047, VACWR050, VACWR051, VACWR053, VACWR054, VACWR055, VACWR057, VACWR059, VACWR060, VACWR061, VACWR065, VACWR068, VACWR072, VACWR073, VACWR080, VACWR082, VACWR083, VACWR089, VACWR094, VACWR098, VACWR101, VACWR103, VACWR106, VACWR109, VACWR112, VACWR114, VACWR117, VACWR123, VACWR124, VACWR127, VACWR138, VACWR141, VACWR143, VACWR152, VACWR154, VACWR156, VACWR158, VACWR160, VACWR165, VACWR166, VACWR169, VACWR170, VACWR172, VACWR173, VACWR174, VACWR176, VACWR178, VACWR180, VACWR181, VACWR181.5, VACWR183, VACWR184, VACWR187, VACWR188, VACWR190, VACWR193, VACWR194, VACWR195, VACWR198, VACWR200, VACWR201, VACWR205, Vaccinia Copenhagen (VC) C23L, VC VACWR002/217 pseudogene, VC C11R, VC C10L, VC C9l, VC C8L, VC C7L, VC C6L, VC C5L, VC C4L, VC N2L, VC M2L, VC K1l, VC K3L, VC K5L, VC K6L, VC K7R, VC F7L, VC F8L, VC F11L, VC F12L, VC F14L, VC F15L, VC F16L, VC E1L, VC E3L, VC E4L, VC E5R, VC E9L, VC O1L, VC I3L, VC I4L, VC G2R, VC G5R, VC G5.5R, VC L2R, VC J2R, VC J6R, VC H3L, VC H5R, VC D1R, VC D4R, VC D7R, VC D9R, VC D12L, VC A4L, VC A5R, VC A8R, VC A18R, VC A20R, VC A23R, VC A29L, VC A31R, VC A33R, VC A35R, VC A37R, VC A40R, VC A41L, VC 268, VC A44L, VC A46R, VC A47L, VC A48R, VC A50R, VC A52R, VC A55R, VC A56R, VC B1R, VC B2R, VC B5R, VC B6R, VC B8R, VC B11R, VC B12R, VC B13R, VC B17L, VC B19, VC VACWR201 Pseudogene, and VC C12L.

26. The recombinant vaccinia virus of claim 24, wherein the pre-replicative promoter is from a vaccinia virus thymidine kinase ORF (VACVWR094).

27. The recombinant vaccinia virus of claim 24, wherein the post-replicative promoter is a vaccinia virus intermediate or late promoter.

28. The recombinant vaccinia virus of claim 24, wherein the post-replicative promoter is from a vaccinia virus ORF selected from the group consisting of vaccinia Western Reserve (VACWR)033, VACWR035, VACWR052, VACWR067, VACWR069, VACWR069.5, VACWR070, VACWR074, VACWR075, VACWR081, VACWR099, VACWR101, VACWR113, VACWR116, VACWR118, VACWR119, VACWR120, VACWR122, VACWR125, VACWR131, VACWR135, VACWR136, VACWR139, VACWR146, VACWR147, VACWR148, VACWR150, VACWR15, VACWR153.5, VACWR155, VACWR162, VACWR204.5, VACWR062, VACWR063, VACWR064, VACWR077, VACWR086, VACWR091, VACWR093, VACWR105, VACWR111, VACWR115, VACWR142, VACWR157, VACWR164, VACWR167, VACWR168, VACWR179, VACWR186, VACWR191, VACWR192, VACWR197, VACWR206, VACWR008, VACWR020, VACWR025, VACWR048, VACWR049, VACWR071, VACWR076, VACWR078, VACWR079, VACWR085, VACWR090, VACWR097, VACWR102, VACWR107, VACWR121, VACWR126, VACWR128, VACWR129, VACWR132, VACWR133, VACWR134, VACWR137, VACWR140, VACWR149, VACWR151, VACWR056, VACWR066, VACWR084, VACWR087, VACWR088, VACWR09, VACWR100, VACWR104, VACWR108, VACWR130, VACWR163, VACWR171, VACWR189, VACWR145, VACWR207, Vaccinia Copenhagen (VC) K2L, VC K4L, VC F13L, VC E11L, VC O2L, VC O3L, VC I1L, VC I5L, VC I6L, VC G4L, VC H1L, VC H3L, VC D8L, VC D11L, VC D13L, VC A1L, VC A2L, VC A3L, VC A6L, VC A12L, VC A15L, VC A16L, VC A19L, VC A25L, VC A27L, VC A30L, VC A30.5L, VC A32L, VC A38L, VC E6R, VC E7R, VC E8R, VC I8R, VC G8R, VC L4R, VC J1R, VC H7R, VC D6R, VC D10R, VC A22, VC A34R, VC A42R, VC A43R, VC A53R, VC B4R, VC B9R, VC C13L, VC C19L, VC C8L, VC C3L, VC F9L, VC F10L, VC I2L, VC I7L, VC G1L, VC G3L, VC G7L, VC L3L, VC J5L, VC H4L, VC D2L, VC A2.5L, VC A7L, VC A9L, VC A10L, VC A13L, VC A14L, VC A14.5L, VC A17L, VC A21L, VC A26L, VC A28L, VC F17R, VC E10, VC G6R, VC G9R, VC L1R, VC L5R, VC H2R, VC H6R, VC D3R, VC A11L, VC A39R, VC A45R, and VC B7R.

29. The recombinant vaccinia virus of claim 24, wherein the post-replicative promoter is from a vaccinia virus I1L (VACWR070) ORF.

30. The recombinant vaccinia virus of claim 24, wherein the at least one inactivating mutation is in an ORF encoding a vaccinia virus late transcription factor.

31. The recombinant vaccinia virus of claim 30, wherein the transcription factor is encoded by the vaccinia virus A8R (VACWR127) ORF, or the vaccinia virus A23R (VACWR143) ORF.

32. A kit comprising the recombinant chordopoxvirus of claim 1.

33. A method of producing a therapeutic composition comprising recombinant chordopoxvirus particles for administration into an individual in need of such therapy, the method comprising:

a) culturing a recombinant cell comprising the recombinant chordopoxvirus of claim 29 in vitro to produce progeny recombinant chordopoxvirus particles, wherein the recombinant cell expresses an active form of the protein encoded by the ORF required for the expression of post-replicative genes; and, b) isolating the progeny recombinant chordopoxvirus particles from the cultured cell, and preparing a therapeutic composition comprising the progeny recombinant chordopoxvirus particles.

* * * * *